(12) United States Patent
Patterson et al.

(10) Patent No.: US 7,662,849 B2
(45) Date of Patent: Feb. 16, 2010

(54) AMIDINO COMPOUNDS AS CYSTEINE PROTEASE INHIBITORS

(75) Inventors: John W. Patterson, Mountain View, CA (US); Soon H. Woo, Palo Alto, CA (US)

(73) Assignee: ViroBay, Inc., Menlo Park, CA (US)

( * ) Notice: Subject to any disclaimer, the term of this patent is extended or adjusted under 35 U.S.C. 154(b) by 505 days.

(21) Appl. No.: 10/559,405

(22) PCT Filed: Jun. 4, 2004

(86) PCT No.: PCT/US2004/017654

§ 371 (c)(1),
(2), (4) Date: Jun. 26, 2006

(87) PCT Pub. No.: WO2004/108661

PCT Pub. Date: Dec. 16, 2004

(65) Prior Publication Data

US 2006/0264464 A1    Nov. 23, 2006

(51) Int. Cl.
*A61K 31/382* (2006.01)
*A61K 31/445* (2006.01)
*C07D 335/02* (2006.01)
*C07D 211/54* (2006.01)

(52) U.S. Cl. .......... 514/432; 514/238.5; 514/311; 514/331; 514/394; 514/416; 514/451; 514/520; 544/59; 544/163; 546/134; 546/230; 546/286; 548/304.4; 548/505; 548/585; 549/13; 549/426; 558/392

(58) Field of Classification Search .......... 514/238.5, 514/311, 331, 394, 416, 432, 451, 520; 544/59, 544/163; 546/134, 230, 286; 548/304.4, 548/505, 585; 549/13, 426; 558/392
See application file for complete search history.

(56) References Cited

U.S. PATENT DOCUMENTS

| 4,959,365 | A  | * | 9/1990  | Francoeur et al. | 514/18    |
|-----------|----|---|---------|------------------|-----------|
| 6,492,362 | B1 | * | 12/2002 | Graupe et al.    | 514/237.5 |
| 6,525,052 | B2 | * | 2/2003  | Bekkali et al.   | 514/237.2 |
| 6,720,319 | B2 | * | 4/2004  | Liu et al.       | 514/232.2 |
| 6,787,540 | B2 | * | 9/2004  | Bekkali et al.   | 514/230.5 |
| 6,841,571 | B2 | * | 1/2005  | Bekkali et al.   | 514/473   |
| 6,936,606 | B2 | * | 8/2005  | Bekkali et al.   | 514/226.8 |
| 6,982,272 | B2 | * | 1/2006  | Emmanuel et al.  | 514/318   |
| 7,056,915 | B2 | * | 6/2006  | Emmanuel et al.  | 514/230.5 |
| 7,101,880 | B2 | * | 9/2006  | Graupe et al.    | 514/232.5 |

FOREIGN PATENT DOCUMENTS

| EP | 0 623 627     | 11/1994 |
|----|---------------|---------|
| WO | WO/00/51998   | 9/2000  |
| WO | WO/01/19796   | 3/2001  |
| WO | WO/01/19816   | 3/2001  |
| WO | WO/02/069901  | 9/2002  |
| WO | WO/03/029200  | 4/2003  |

OTHER PUBLICATIONS

Bekkali et al. "Preparation of spiroheterocycli . . . " CA 137:247932 (2002).*

* cited by examiner

*Primary Examiner*—Celia Chang
(74) *Attorney, Agent, or Firm*—Townsend and Townsend and Crew LLP

(57) ABSTRACT

The present invention is directed to compounds that are inhibitors of cysteine proteases, in particular, cathepsins B, K, L, F, and S and are therefore useful in treating diseases mediated by these proteases. The present invention is directed to pharmaceutical compositions comprising these compounds and processes for preparing them.

14 Claims, No Drawings

US 7,662,849 B2

AMIDINO COMPOUNDS AS CYSTEINE PROTEASE INHIBITORS

FIELD OF THE INVENTION

The present invention is directed to compounds that are inhibitors of cysteine proteases, in particular, cathepsins B, K, L, F, and S and are therefore useful in treating diseases mediated by these proteases. The present invention is directed to pharmaceutical compositions comprising these compounds and processes for preparing them.

STATE OF THE ART

Cysteine proteases represent a class of peptidases characterized by the presence of a cysteine residue in the catalytic site of the enzyme. Cysteine proteases are associated with the normal degradation and processing of proteins. The aberrant activity of cysteine proteases, e.g., as a result of increased expression or enhanced activation, however, may have pathological consequences. In this regard, certain cysteine proteases are associated with a number of disease states, including arthritis, muscular dystrophy, inflammation, tumor invasion, glomerulonephritis, malaria, periodontal disease, metachromatic leukodystrophy and others. For example, increased cathepsin B levels and redistribution of the enzyme are found in tumors; thus, suggesting a role for the enzyme in tumor invasion and metastasis. In addition, aberrant cathepsin B activity is implicated in such disease states as rheumatoid arthritis, osteoarthritis, *pneumocystis carinii*, acute pancreatitis, inflammatory airway disease and bone and joint disorders.

The prominent expression of cathepsin K in osteoclasts and osteoclast-related multinucleated cells and its high collagenolytic activity suggest that the enzyme is involved in ososteoclast-mediated bone resorption and, hence, in bone abnormalities such as occurs in osteoporosis. In addition, cathepsin K expression in the lung and its elastinolytic activity suggest that the enzyme plays a role in pulmonary disorders as well.

Cathepsin L is implicated in normal lysosomal proteolysis as well as several disease states, including, but not limited to, metastasis of melanomas. Cathepsin S is implicated in Alzheimer's disease and certain autoimmune disorders, including, but not limited to juvenile onset diabetes, multiple sclerosis, pemphigus vulgaris, Graves' disease, myasthenia gravis, systemic lupus erythemotasus, rheumatoid arthritis and Hashimoto's thyroiditis. In addition, cathepsin S is implicated in: allergic disorders, including, but not limited to asthma; and allogeneic immune reponses, including, but not limited to, rejection of organ transplants or tissue grafts.

Another cysteine protease, Cathepsin F, has been found in macrophages and is involved in antigen processing. It is believed that Cathepsin F in stimulated lung macrophages and possibly other antigen presenting cells could play a role in airway inflammation (see G. P. Shi et al, J. Exp. Med. 191, 1177, 2000)

In view of the number of diseases wherein it is recognized that an increase in cysteine protease activity contributes to the pathology and/or symptomatology of the disease, molecules which inhibit the activity of this class of enzymes, in particular molecules which inhibitor cathepsins B, K, L, F, and/or S, will therefore be useful as therapeutic agents.

SUMMARY OF THE INVENTION

In one aspect, this invention is directed to a compound of Formula (Ia) or (Ib):

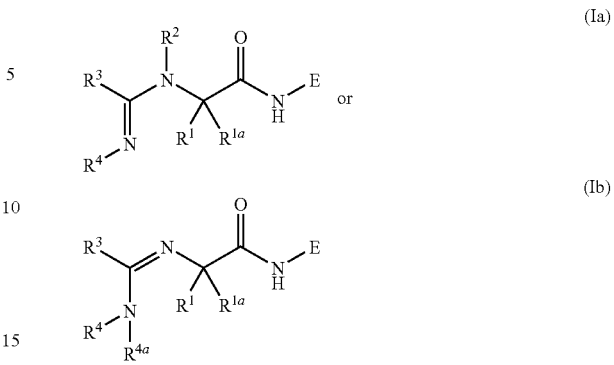

wherein:
E is:
(i) —$C(R^5)(R^6)X^1$ where $X^1$ is —CHO, —$C(R^7)(R^8)CF_3$, —$C(R^7)(R^8)CF_2CF_2R^9$, —$C(R^7)(R^8)R^{10}$, —CH=$CHS(O)_2R^{10}$, —$CO(R^7)(R^8)C(R^7)(R^8)OR^{10}$, —$C(R^7)(R^8)CH_2OR^{10}$, —$C(R^7)(R^8)C(R^7)(R^8)R^{10}$, —$C(R^7)(R^8)CH_2N(R^{11})SO_2R^{10}$, —$C(R^7)(R^8)CF_2C(O)NR^{10}R^{11}$, —$C(R^7)(R^8)C(O)NR^{10}R^{11}$, —$C(R^7)(R^8)C(O)N(R^{11})(CH_2)_2OR^{11}$, or —$C(R^7)(R^8)C(O)N(R^{11})(CH_2)_2NR^{10}R^{11}$;
(ii) $C(R^{5a})(R^{6a})CN$;
where:
$R^5$ and $R^{5a}$ are independently hydrogen or alkyl; and
$R^6$ and $R^{6a}$ are independently selected from the group consisting of hydrogen, alkyl, haloalkyl, carboxyalkyl, alkoxycarbonylalkyl, cycloalkyl, cycloalkylalkyl, aryl, aralkyl, heteroaryl, heteroaralkyl, heterocyclyl, heterocyclylalkyl, cyano, -alkylene-X—$R^{12}$ (where X is —O—, —$NR^{13}$—, —$CONR^{13}$—, —$S(O)_{n1}$—, —NHCO—, —CO—, or —C(O)O— where n1 is 0-2, and $R^{12}$ and $R^{13}$ are independently hydrogen, alkyl, haloalkyl, cycloalkyl, cycloalkylalkyl, aryl, aralkyl, heteroaryl, or heteroaralkyl) wherein the aromatic or alicyclic ring in $R^6$ and $R^{6a}$ is optionally substituted with one, two, or three $R^a$ independently selected from alkyl, haloalkyl, alkoxy, hydroxy, haloalkoxy, halo, carboxy, alkoxycarbonyl, amino, monosubstituted amino, disubstituted amino, nitro, aryloxy, benzyloxy, acyl, or arylsulfonyl where the aromatic or alicyclic ring in $R^a$ is optionally substituted with one or two substituents independently selected from alkyl, halo, alkoxy, haloalkyl, haloalkoxy, hydroxy, amino, alkylamino, dialkylamino, carboxy, or alkoxycarbonyl; or
$R^5$ and $R^6$ and $R^{5a}$ and $R^{6a}$ taken together with the carbon atom to which both $R^5$ and $R^6$ and $R^{5a}$ and $R^{6a}$ are attached form (i) cycloalkylene optionally substituted with one or two $R^b$ independently selected from alkyl, halo, alkylamino, dialkylamino, aryl, aralkyl, cycloalkyl, cycloalkylalkyl, heteroaryl, heteroaralkyl, alkoxycarbonyl, or aryloxycarbonyl, or (ii) heterocycloalkylene optionally substituted with one to four $R^c$ which are independently selected from alkyl, haloalkyl, hydroxy, hydroxyalkyl, alkoxyalkyl, alkoxyalkyloxyalkyl, aryloxyalkyl, heteroaryloxyalkyl, aminoalkyl, acyl, aryl, aralkyl, heteroaryl, heteroaralkyl, heterocyclyl, heterocyclylalkyl, cycloalkyl, cycloalkylalkyl, —$S(O)_{n2}R^{14}$, -alkylene-$S(O)_{n2}$—$R^{15}$, —$COOR^{16}$, alkylene-$COOR^{17}$, —$CONHR^{18}R^{19}$, or -alkylene-$CONHR^{20}R^{21}$ (where n2 is 0-2 and $R^{14}$-$R^{17}$, $R^{18}$ and $R^{20}$ are independently hydrogen, alkyl, haloalkyl, aryl, aralkyl, heteroaryl, heteroaralkyl, cycloalkyl, cycloalkylalkyl, or heterocyclyl and $R^{19}$ and $R^{21}$ are independently hydrogen or alkyl) wherein the aromatic or alicyclic ring in the groups attached to cycloalkylene or heterocycloalkylene is optionally substituted with one, two, or three substituents independently selected from alkyl, haloalkyl, alkoxy, hydroxy, haloalkoxy, halo, carboxy, alkoxycarbonyl, amino, monsubstituted amino, disubstituted amino, or acyl;

$R^7$ is hydrogen or alkyl;

$R^8$ is hydroxy; or $R^7$ and $R^8$ together form oxo;

$R^9$ is hydrogen, halo, alkyl, aralkyl or heteroaralkyl;

$R^{10}$ is alkyl, aryl, aralkyl, heteroaryl, heteroaralkyl, cycloalkyl, cycloalkylalkyl, heterocyclyl, or heterocyclylalkyl wherein the aromatic or alicyclic ring in $R^{10}$ is optionally substituted with one, two, or three $R^d$ independently selected from alkyl, haloalkyl, alkoxy, cycloalkyl, hydroxy, haloalkoxy, halo, carboxy, alkoxycarbonyl, aryl, heteroaryl, amino, monsubstituted amino, disubstituted amino, or acyl wherein the aromatic or alicyclic ring in $R^d$ is optionally substituted with one, two, or three substitutents independently selected from alkyl, haloalkyl, alkoxy, haloalkoxy, halo, hydroxy, carboxy, alkoxycarbonyl, amino, alkylamino, or dialkylamino; and $R^{11}$ is hydrogen or alkyl; or (iii) a group of formula (a):

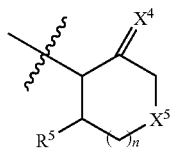

(a)

where:

n is 0, 1, or 2;

$X^4$ is selected from —$NR^{22}$—, —S—, or —O— where $R^{22}$ is hydrogen, alkyl, or alkoxy; and $X^5$ is —O—, —S—, —$SO_2$—, or —$NR^{23}$ where $R^{23}$ is selected from hydrogen, alkyl, haloalkyl, hydroxyalkyl, alkoxyalkyl, aryloxyalkyl, heteroaryloxyalkyl, aminoalkyl, acyl, aryl, aralkyl, heteroaryl, heteroaralkyl, cycloalkyl, cycloalkylalkyl, —$S(O)_2R^{24}$, -alkylene-S(O), —$R^{25}$, —$COOR^{26}$, -alkylene-$COOR^{27}$, —$CONR^{28}R^{29}$, or -alkylene-$CONR^{3}OR^{31}$ (where n3 is 0-2 and $R^{24}$-$R^{27}$, $R^{28}$ and $R^{30}$ are independently hydrogen, alkyl, haloalkyl, aryl, aralkyl, heteroaryl, heteroaralkyl, cycloalkyl, cycloalkylalkyl, heterocyclyl, or heterocyclylalkyl and $R^{29}$ and $R^{31}$ are independently hydrogen or alkyl) where the aromatic or alicyclic ring in Xs is optionally substituted with one, two, or three substituents independently selected from alkyl, haloalkyl, alkoxy, haloalkoxy, halo, hydroxy, amino, alkylamino, dialkylamino, carboxy, or alkoxycarbonyl;

$R^5$ is as defined above;

$R^1$ is hydrogen or alkyl;

$R^{1a}$ is hydrogen, alkyl, haloalkyl, cycloalkyl, cycloalkylalkyl, aryl, aralkyl, heteroaryl, heteroaralkyl, heterocyclylalkyl, or -alkylene-$X^2$—$R^{32}$ [wherein $X^2$ is —$NR^{33}$—, —O—, —$S(O)_{n4}$—, —CO—, —COO—, —OCO—, —$NR^{33}CO$—, —$CONR^{33}$—, —$NR^{33}SO_2$—, —$SO_2NR^{33}$—, —$NR^{33}COO$—, —$OCONR^{33}$—$NR^{33}CONR^{34}$, or —$NR^{33}SO_2NR^{33}$— (where $R^{33}$ and $R^{34}$ are independently hydrogen, alkyl, or acyl and n4 is 0-2) and $R^{32}$ is hydrogen, alkyl, haloalkyl, cycloalkyl, cycloalkylalkyl, heterocyclyl, aryl, aralkyl, heteroaryl, heteroaralkyl, or heterocyclylalkyl] wherein said alkylene chain in -alkylene-$X^2$—$R^{32}$ is optionally substituted with one to six halo and wherein the aromatic or alicyclic ring in $R^{1a}$ is optionally substituted with one, two, or three $R^{1a}$ independently selected from alkyl, haloalkyl, alkoxy, hydroxy, haloalkoxy, halo, nitro, cyano, carboxy, alkoxycarbonyl, aryl, heteroaryl, cycloalkyl, cycloalkylalkyl, aralkyl, heteroaralkyl, amino, monsubstituted amino, disubstituted amino, or acyl; or $R^1$ and $R^{1a}$ together with the carbon atoms to which they are attached form cycloalkylene or heterocycloalkylene ring wherein said cycloalkylene or heterocycloalkylene is optionally substituted with one or two $R^f$ independently selected from alkyl, halo, hydroxyalkyl, keto, or —$SO_2R^{39}$ where $R^{39}$ is alkyl, cycloalkyl, cycloalkylalkyl, aryl, aralkyl, heteroaryl or heteroaralkyl where the aromatic or alicylic ring in $R^f$ is optionally substituted with one, two, or three substitutents independently selected from alkyl, alkoxy, haloalkyl, haloalkoxy, hydroxy, halo, carboxy, or alkoxycarbonyl;

$R^2$ is hydrogen or alkyl;

$R^3$ is hydrogen, alkyl, haloalkyl, cycloalkyl, aryl, aralkyl, heteroaryl, heteroaralkyl, heterocyclyl, heterocyclylalkyl, amino, mono or disubstituted amino, or -alkylene-$X^3$—$R^{35}$ [wherein X is —$NR^{36}$—, —O, —$S(O)_{n5}$—, —CO—, —COO—, —OCO—, —$NR^{36}CO$—, —$CONR^{36}$—, —$NR^{36}SO_2$—, —$SO_2NR^{36}$—, —$NR^{36}COO$—, —$OCONR^{36}$, —$NR^{36}CONR^{37}$—, or —$NR^{36}SO_2NR^{37}$— (where $R^{36}$ and $R^{37}$ are independently hydrogen, alkyl, or acyl and n5 is 0-2) and $R^{35}$ is hydrogen, alkyl, haloalkyl, cycloalkyl, cycloalkylalkyl, aryl, aralkyl, heteroaryl, or heteroaralkyl] wherein the aromatic or alicyclic rings in $R^3$ are optionally substituted by one, two, or three $R^g$ independently selected from alkyl, halo, hydroxy, alkoxy, haloalkyl, haloalkoxy, oxo, cyano, nitro, acyl, acyloxy, aryl, heteroaryl, cycloalkyl, heterocyclyl, aryloxy, benzyloxy, carboxy, alkoxycarbonyl, aryloxycarbonyl, carbamoyl, alkylthio, alkylsulfinyl, alkylsulfonyl, arylthio, arylsulfonyl, arylsulfinyl, alkoxycarbonylamino, aryloxycarbonylamino, alkylcarbamoyloxy, arylcarbamoyloxy, alkylsulfonylamino, arylsulfonylamino, aminosulfonyl, alkylaminosulfonyl, dialkylaminosulfonyl, arylaminosulfonyl, amino, monosubsituted or disubstituted amino, and further wherein the aromatic and alicyclic rings in $R^g$ are optionally substituted with one, two, or three $R^h$ wherein $R^h$ is independently selected from alkyl, halo, haloalkyl, haloalkoxy, hydroxy, nitro, cyano, hydroxyalkyl, alkoxy, alkoxyalkyl, aminoalkyl, alkylthio, alkylsulfonyl, amino, alkylamino, dialkylamino, aryl, heteroaryl, cycloalkyl, carboxy, carboxamido, or alkoxycarbonyl;

$R^4$ is —$S(O)_2R^{38}$ where $R^{38}$ is phenyl or naphthyl optionally substituted with one, two, or three $R^i$ independently selected from alkyl, alkoxy, halo, haloalkyl, haloalkoxy, hydroxy, alkylthio, alkylsulfonyl, arylsulfonyl, aminosulfonyl, acyl, amino, monosubstituted amino, disubstituted amino, carboxy, alkoxycarbonyl, hydroxyalkyl, alkoxyalkyl, aminoalkyl, aryl, heteroaryl, heterocyclyl, aryloxycarbonyl, heteroaryloxycarbonyl, aryloxy, heteroaryloxy, —$NHSO_2R^j$ where $R^j$ is alkyl, aryl, or heteroaryl, —$SO_2NR^kR^l$ where $R^k$ is hydrogen or alkyl and $R^l$ is alkyl, aryl, heteroaryl, hydroxyalkyl, alkoxyalkyl, or aminoalkyl, —$NHCOOR^m$ where $R^m$ is alkyl, aryl, or heteroaryl, or —$NHCONR''R^o$ where $R''$ and $R^o$ are independently hydrogen, alkyl, aryl, aralkyl, heteroaryl, or heteroaralkyl; where the aromatic or alicyclic ring in the groups contained in $R^i$ is optionally substituted with one or two substituents independently selected from alkyl, halo, alkoxy, haloalkyl, haloalkoxy, hydroxy, amino, alkylamino, dialkylamino, carboxy, or alkoxycarbonyl;

$R^{4a}$ is hydrogen, alkyl, halo, haloalkyl, haloalkyl, hydroxyalkyl, alkoxyalkyl, alkoxy, hydroxy, aryl, aralkyl, aroyl, heteroaryl, heteraralkyl, heteroaroyl, —C(O)OR$^{40}$ where (R$^{40}$ is hydrogen, alkyl, haloalkyl, cycloalkyl, cycloalkylalkyl, heteroaryl, heteroarylalkyl, aryl, or aralkyl), alkylsulfonyl, arylsulfonyl, heteroarylsulfonyl, alkylaminosulfonyl, arylaminosulfonyl, or cycloalkyl wherein the aromatic rings in R$^{4a}$ are optionally substituted with one, two or three halogen, hydroxy, alkyl, alkoxy, haloalkyl, haloalkoxy, carboxy, nitrile, nitro or —CONH$_2$;

or a pharmaceutically acceptable salts thereof.

Within the above group of compounds, a more preferred group of compounds is that wherein R$^{38}$ is phenyl or naphthyl optionally substituted with one, two, or three R$^i$ independently selected from alkyl, alkoxy, halo, haloalkyl, haloalkoxy, hydroxy, alkylthio, alkylsulfonyl, arylsulfonyl, aminosulfonyl, acyl, amino, monosubstituted amino, disubstituted amino, carboxy, alkoxycarbonyl, hydroxyalkyl, alkoxyalkyl, aminoalkyl, aryl, heteroaryl, or heterocyclyl where the aromatic or alicyclic ring in the groups contained in R$^i$ is optionally substituted with one or two substituents independently selected from alkyl, halo, alkoxy, haloalkyl, haloalkoxy, hydroxy, amino, alkylamino, dialkylamino, carboxy, or alkoxycarbonyl.

A second aspect of the invention is a pharmaceutical composition comprising a compound of Formula (Ia) or (Ib), individual isomer or mixture of isomers thereof, or a pharmaceutically acceptable salt thereof, in admixture with one or more suitable excipients.

A third aspect of the invention is a method for treating a disease in an animal mediated by cysteine proteases, in particular cathepsin K or S which method comprises administering to the animal a therapeutically effective amount of compound of Formula (Ia) or (Ib), individual isomer or mixture of isomers thereof; or a pharmaceutically acceptable salt thereof.

In a fourth aspect, this invention is directed to the use of a compound of Formula (Ia) or (Ib), individual isomer or mixture of isomers thereof; or a pharmaceutically acceptable salt thereof in the preparation of a medicament. Preferably, the medicament is for used in the treatment of a disease mediated by Cathepsin S. Preferably, the disease is psoriasis or myasthesnia gravis.

DETAILED DESCRIPTION OF THE INVENTION

Definitions:

Unless otherwise stated, the following terms used in the specification and claims are defined for the purposes of this Application and have the following meanings.

"Alicyclic" means a moiety characterized by arrangement of the carbon atoms in closed non-aromatic ring structures having properties resembling those of aliphatics e.g., cycloalkyl and heterocyclyl rings as defined herein.

"Alkyl" represented by itself means a straight or branched, saturated aliphatic radical containing one to six carbon atoms, unless otherwise indicated (e.g., alkyl includes methyl, ethyl, propyl, isopropyl, butyl, sec-butyl, isobutyl, tert-butyl, and the like). Alkyl represented along with another radical (e.g., as in arylalkyl) means a straight or branched, saturated aliphatic divalent radical having the number of atoms indicated (e.g., aralkyl includes benzyl, phenethyl, 1-phenylethyl 3-phenylpropyl, and the like). It should be understood that any combination term using an "alk" or "alkyl" prefix refers to analogs according to the above definition of "alkyl". For example, terms such as "alkoxy" "alkythio" refer to alkyl groups linked to a second group via an oxygen or sulfur atom.

"Alkylene", unless indicated otherwise, means a straight or branched, saturated aliphatic, divalent radical having the number of one to six carbon atoms, e.g., methylene (—CH$_2$—), ethylene (—CH$_2$CH$_2$—), trimethylene (—CH$_2$CH$_2$CH$_2$—), tetramethylene (—CH$_2$CH$_2$CH$_2$CH$_2$—) 2-methyltetramethylene (—CH$_2$CH(CH$_3$)CH$_2$CH$_2$—), pentamethylene (—CH$_2$CH$_2$CH$_2$CH$_2$CH$_2$—), and the like.

"Alkylidene" means a straight or branched saturated or unsaturated, aliphatic, divalent radical having the number of carbon atoms indicated (e.g. (C$_{1-6}$)alkylidene includes methylene (=CH$_2$), ethylidene (=CHCH$_3$), isopropylidene (=C(CH$_3$)$_2$), propylidene (=CHCH$_2$CH$_3$), allylidene (=CH—CH=CH$_2$), and the like).

"Alkylcarbamoyloxy" refers to a radical —OCONHR where R is an alkyl group as defined above e.g., methylcarbamoyloxy, ethylcarbamoyloxy, and the like.

"Alkylsulfonylamino" refers to a radical —NHSO$_2$R where R is an alkyl group as defined above e.g., methylsulfonylamino, ethylsulfonylamino, and the like.

"Amino" means the radical —NH$_2$. Unless indicated otherwise, the compounds of the invention containing amino moieties include protected derivatives thereof. Suitable protecting groups for amino moieties include acetyl, tert-butoxycarbonyl, benzyloxycarbonyl, and the like.

"Aminosulfonyl" refers to a radical —SO$_2$NH$_2$.

"Alkylaminosulfonyl" or "dialkylaminosulfonyl" refers to a radical —SO$_2$NHR and —SO$_2$NRR' respectively, where R and R' are independently alkyl group as defined above e.g., methylaminosulfonyl, and the like.

"Alkylamino" or "dialkylamino" refers to a radical —NHR and —NRR' respectively, where R and R' are independently alkyl group as defined above e.g., methylamino, dimethylamino, and the like.

"Alkoxy" refers to a radical —OR where R is an alkyl group as defined above e.g., methoxy, ethoxy, and the like.

"Alkoxycarbonyl" refers to a radical —C(O)OR where R is an alkyl group as defined above e.g., methoxycarbonyl, ethoxycarbonyl, and the like.

"Alkoxycarbonylalkyl" means the radical -(alkylene)-C(O)OR where R is alkyl as defined above e.g., methoxycarbonylalkyl, 2-, or 3-ethoxycarbonylmethyl, and the like.

"Alkoxycarbonylamino" refers to a radical —NHC(O)OR where R is an alkyl group as defined above e.g., methoxycarbonyl, ethoxycarbonyl, and the like.

"Alkoxyalkyl" means a linear monovalent hydrocarbon radical of one to six carbon atoms or a branched monovalent hydrocarbon radical of three to six carbons substituted with at least one alkoxy group, preferably one or two alkoxy groups, as defined above, e.g., 2-methoxyethyl, 1-, 2-, or 3-methoxypropyl, 2-ethoxyethyl, and the like.

"Alkoxyalkyloxyalkyl" refers to a radical -(alkylene)-O-(alkylene)-OR where R is an alkyl group as defined above, e.g., 2-methoxyethyloxymethyl, 3-methoxypropyloxyethyl, and the like.

"Aminoalkyl" means a linear monovalent hydrocarbon radical of one to six carbon atoms or a branched monovalent hydrocarbon radical of three to six carbons substituted with at least one, preferably one or two, —NRR' where R is hydrogen, alkyl, or —COR$^a$ where R$^a$ is alkyl, and R' is hydrogen or alkyl as defined above e.g., aminomethyl, methylaminoethyl, dimethylaminoethyl, 1,3-diaminopropyl, acetylaminopropyl, and the like.

"Alkylthio" refers to a radical —SR where R is an alkyl group as defined above e.g., methylthio, ethylthio, and the like.

"Alkylsulfinyl" refers to a radical —S(O)R where R is an alkyl group as defined above e.g., methylsylfinyl, ethylsulfinyl, and the like.

"Alkylsulfonyl" refers to a radical —SO$_2$R where R is an alkyl group as defined above e.g., methylsulfonyl, ethylsulfonyl, and the like.

"Acyl" means a radical —COR where R is hydrogen, alkyl, haloalkyl, aryl, aralkyl, heteroaryl, heteroaralkyl, or heterocyclyl as defined herein, e.g., formyl, acetyl, trifluoroacetyl, benzoyl, piperazin-1-ylcarbonyl, and the like.

"Acyloxy" means a radical —OCOR where R is alkyl, haloalkyl, aryl, aralkyl, heteroaryl, heteroaralkyl, or heterocyclyl as defined herein, e.g., acetyloxy, trifluoroacetyloxy, benzoyloxy, piperazin-1-ylcarbonyloxy, and the like.

"Animal" includes humans, non-human mammals (e.g., dogs, cats, rabbits, cattle, horses, sheep, goats, swine, deer, and the like) and non-mammals (e.g., birds, and the like).

"Aromatic" means a moiety wherein the constituent atoms make up an unsaturated ring system, all atoms in the ring system are sp$^2$ hybridized and the total number of pi electrons is equal to 4n+2.

"Aryl" means a monocyclic or fused bicyclic ring assembly containing 6 to 10 ring carbon atoms unless otherwise indicated, wherein each ring is aromatic e.g., phenyl or anthryl.

"Aralkyl" means a radical -(alkylene)-R where R is aryl as defined above e.g., benzyl, phenethyl, and the like.

"Aryloxy" means a radical —OR where R is aryl as defined above.

"Aryloxyalkyl" means the radical -(alkylene)-OR where R is aryl as defined above e.g., phenoxymethyl, 2-, or 3-phenoxymethyl, and the like "Aryloxycarbonyl" means the radical —C(O)OR where R is aryl as defined above e.g., phenyloxycarbonyl, and the like.

"Arylcarbamoyloxy" means the radical —OC(O)NHR where R is aryl as defined above e.g., phenylcarbamoyloxy, and the like.

"Aroyl" means the radical —COR where R is aryl as defined above e.g., benzoyl.

"Arylthio" refers to a radical —SR where R is an aryl group e.g., phenylthio, and the like. "Arylsulfinyl" refers to a radical —SOR where R is an aryl group e.g., phenylsulfinyl, and the like.

"Arylsulfonyl" refers to a radical —SO$_2$R where R is an aryl group e.g., phenylsulfonyl, and the like.

"Aryloxycarbonylamino" refers to a radical —NHC(O)OR where R is an aryl group as defined above e.g., phenoxycarbonylamino, and the like.

"Arylsulfonylamino" refers to a radical —NHSO$_2$R where R is an aryl group as defined above, e.g., phenylsulfonylamino, and the like.

"Arylaminosulfonyl" means the radical —SO$_2$NHR where R is aryl as defined above e.g., phenylaminosulfonyl, and the like.

"Carboxamide" means the radical —C(O)NH$_2$.

"Carbamoyl" means the radical —C(O)NRR' where R and R' are independently selected from hydrogen, alkyl, aryl, aralkyl, heteroaryl, heteroaralkyl, heterocyclyl or heterocyclylalkyl as defined herein provided one of R and R' is not hydrogen.

"Carbocyclic ketone derivative" means a derivative containing the moiety —C(O)—.

"Carboxy" means the radical —C(O)OH.

"Carboxyalkyl" means the radical -(alkylene)-C(O)OH e.g., carboxymethyl, carboxyethyl, and the like.

"Cycloalkyl" means a monovalent saturated or partially unsaturated, monocyclic, fused bicyclic or bridged polycyclic ring assembly containing three to eight ring carbon atoms and any alkylidene or carbocyclic ketone (one or two oxo groups) derivative thereof e.g., cyclopropyl, cyclobutyl, cyclopentyl, cyclohexyl, cyclohexenyl, 2,5-cyclohexadienyl, bicyclo[2.2.2]octyl, adamantan-1-yl, oxocyclohexyl, dioxocyclohexyl, and the like.

"Cycloalkylalkyl" means the radical -(alkylene)-R where R is cycloalkyl as defined above e.g., cyclopropylmethyl, cyclobutylethyl, cyclobutylmethyl, and the like "Cycloalkylene" means a divalent saturated or partially unsaturated monocyclic ring or bridged polycyclic ring assembly containing three to eight ring carbon atoms, and any carbocyclic ketone (one or two keto groups), derivative thereof. For example, the instance wherein "R$^1$ and R$^{1a}$ together with the carbon atom to which both R$^1$ and R$^{1a}$ are attached form cycloalkylene" includes, but is not limited to, the following:

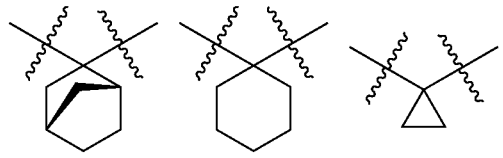

"Disubstituted amino" means a radical —NRR' where R is alkyl, aryl, aralkyl, heteroaryl, heteraralkyl, or heterocyclyl, and R' is alkyl, aryl, aralkyl, heteroaryl, heteroaralkyl, cycloalkyl, heterocyclyl, cycloalkylalkyl, hydroxyalkyl, alkoxyalkyl, or acyl as defined herein. Representative examples include, but are not limited to, dimethylamino, methylphenylamino, benzylmethylamino, acetylmethylamino, and the like.

"Disease" specifically includes any unhealthy condition of an animal or part thereof and includes an unhealthy condition that may be caused by, or incident to, medical or veterinary therapy applied to that animal, i.e., the "side effects" of such therapy.

"Halo" means fluoro, chloro, bromo or iodo.

"Haloalkyl" means alkyl substituted by one or more, preferably one to five, "halo" atoms, as such terms are defined in this Application. Haloalkyl includes monohaloalkyl, dihaloalkyl, trihaloalkyl, perhaloalkyl and the like e.g. chloromethyl, dichloromethyl, difluoromethyl, trifluoromethyl, 2,2,2-trifluoroethyl, perfluoroethyl, 2,2,2-trifluoro-1,1-dichloroethyl, and the like).

"Haloalkoxy" refers to a radical —OR where R is haloalkyl group as defined above e.g., trifluoromethoxy, 2,2,2-trifluoroethoxy, difluoromethoxy, and the like.

"Heterocyclyl" means cycloalkyl, as defined in this Application, provided that one or more, preferably one, two, or three of the ring carbon atoms indicated are replaced by a heteroatom moiety selected from —N=, —N—, —O—, —CO—, —S—, —SO—, or —S(O)$_2$—. Representative examples include, but are not limited to, imidazolidinyl, morpholinyl, thiomorpholinyl, thiomorpholino-1-oxide, thiomorpholino-1,1-dioxide, tetrahydropyranyl, tetrahydrothiopyranyl, 1-oxo-tetrahydrothiopyranyl, 1,1-dioxotetrathiopyranyl, indolinyl, piperazinyl, piperidyl, pyrrolidinyl, pyrrolinyl, quinuclidinyl, and the like.

"Heterocyclylalkyl" means -(alkylene)-heterocyclyl as defined in this Application. Representative examples include, but are not limited to, imidazolidin-1-ylmethyl, morpholin-4-ylmethyl, thiomorpholin-4-ylmethy, thiomorpholin-4-yl-methyl-1-oxide, indolinylethyl, piperazinylmethyl or ethyl, piperidylmethyl or ethyl, pyrrolidinylmethyl or ethyl, and the like.

"Heterocycloalkylene" means cycloalkylene, as defined in this Application, provided that one or more, preferably one or two, of the ring member carbon atoms indicated, is replaced by heteroatom moiety selected from —N═, —N—, —O—, —S— or —S(O)$_2$—. For example, the instance wherein $R^1$ and $R^2$ together with the carbon atom to which both $R^1$ and $R^{1a}$ are attached form heterocycloalkylene" includes, but is not limited to, the following:

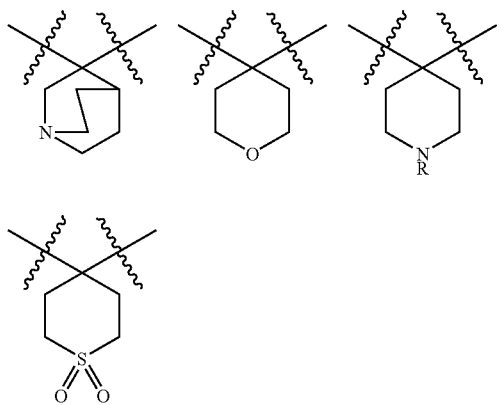

in which R is a substituent defined in the Summary of the Invention

"Heteroaryl" as a group or part of a group denotes an aromatic monocyclic or multicyclic moiety of about 5 to about 10 ring members in which one or more, preferably one, two, or three, of the ring members is/are element(s) other than carbon, for example nitrogen, oxygen or sulfur. Representative heteroaryl rings include, but are not limited to, pyrrolyl, furanyl, thienyl, oxazolyl, isoxazolyl, thiazolyl, imidazolyl, triazolyl, tetrazolyl, pyridinyl, pyrimidinyl, pyrazinyl, pyridazinyl, indolyl, benzofuranyl, benzothienyl, benzimidazolyl, quinolinyl, isoquinolinyl, quinazolinyl, quinoxalinyl, pyrazolyl, and the like.

"Heteroaryloxy" means a radical —O—R where R is heteroaryl as defined above.

"Heteroaryloxycarbonyl" means a radical —C(O)O—R where R is heteroaryl as defined above.

"Heteroaroyl" means a radical —C(O)—R where R is heteroaryl as defined above.

"Heteroaralkyl" means a radical -(alkylene)-R where R is heteroaryl as defined above e.g., pyridinylmethyl, 1- or 2-furanylethyl, imidazolylmethyl, and the like.

"Heteroaryloxyalkyl" means the radical -(alkylene)-OR where R is heteroaryl as defined above e.g., furanyloxymethyl, 2-, or 3-indolyloxyethyl, and the like.

"Heteroarylsulfonyl" refers to a radical —SO$_2$R where R is an heteroaryl group as defined above e.g., pyridinylsulfonyl, and the like.

"Hydroxy" means the radical —OH. Unless indicated otherwise, the compounds of the invention containing hydroxy radicals include protected derivatives thereof. Suitable protecting groups for hydroxy moieties include benzyl and the like.

"Hydroxyalkyl" means a linear monovalent hydrocarbon radical of one to six carbon atoms or a branched monovalent hydrocarbon radical of three to six carbons substituted with one or two hydroxy groups, provided that if two hydroxy groups are present they are not both on the same carbon atom. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Isomers" mean compounds of Formula (Ia) or (Ib) having identical molecular formulae but differ in the nature or sequence of bonding of their atoms or in the arrangement of their atoms in space. Isomers that differ in the arrangement of their atoms in space are termed "stereoisomers". Stereoisomers that are not mirror images of one another are termed "diastereomers" and stereoisomers that are nonsuperimposable mirror images are termed "enantiomers" or sometimes "optical isomers". A carbon atom bonded to four nonidentical substituents is termed a "chiral center". A compound with one chiral center has two enantiomeric forms of opposite chirality is termed a "racemic mixture". A compound that has more than one chiral center has $2^{m-1}$ enantiomeric pairs, where n is the number of chiral centers. Compounds with more than one chiral center may exist as ether an individual diastereomers or as a mixture of diastereomers, termed a "diastereomeric mixture". When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992). It is understood that the names and illustration used in this Application to describe compounds of Formula (Ia) or (Ib) are meant to be encompassed all possible stereoisomers.

Additionally, compounds of Formula (Ia) and (Ib) may exist as tautomers. Such tautomeric forms (individual tautomers or mixtures thereof) are within the scope of this invention. For example, a compound of Formula (Ia) where $R^2$ is hydrogen can tautomerize to give a compound of Formula (Ib) where $R^{4a}$ is hydrogen and vice versa as shown below.

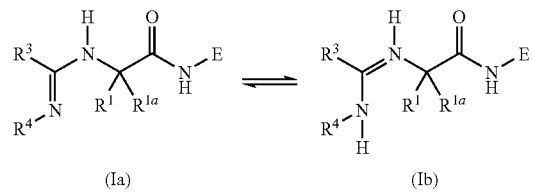

It will be recognized by a person skilled in the art that the amount of tautomers will vary based on certain conditions such as steric interactions, electronic effects of substituents, solvent polarity, hydrogen bonding capabability, temperature, pH, and the like.

"Keto or oxo" means the radical (=O).

"Monosubstituted amino" means a radical —NHR where R is alkyl, aryl, aralkyl, heteroaryl, heteroaralkyl, cycloalkyl, cycloalkylalkyl, hydroxyalkyl, alkoxyalkyl, or acyl as defined herein. Representative examples include, but are not limited to, methylamino, phenylamino, benzylamino, cycloalkylmethylamino, acetylamino, trifluoroacetyl, and the like.

"Nitro" means the radical —$NO_2$.

"Optional" or "optionally" or "may be" means that the subsequently described event or circumstance may or may not occur, and that the description includes instances where the event or circumstance occurs and instances in which it does not. For example, the phrase "wherein the aromatic ring $R^1$ is optionally substituted with one or two substituents independently selected from alkyl." means that the aromatic ring may or may not be substituted with alkyl in order to fall within the scope of the invention.

The present invention also includes N-oxide derivatives of a compound of Formula (Ia) or (Ib). N-oxide derivatives means derivatives of compounds of Formula (Ia) or (Ib) in which nitrogens are in an oxidized state (i.e., N→O) e.g., pyridine N-oxide, and which possess the desired pharmacological activity.

"Pathology" of a disease means the essential nature, causes and development of the disease as well as the structural and functional changes that result from the disease processes.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of Formula (Ia) or (Ib)which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl) benzoic acid, cinnamic acid, mandelic acid, methylsulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

The present invention also includes prodrugs of a compound of Formula (Ia) or (Ib). Prodrug means a compound that is convertible in vivo by metabolic means (e.g. by hydrolysis) to a compound of Formula (Ia) or (Ib). For example an ester of a compound of Formula (Ia) or (Ib) containing a hydroxy group may be convertible by hydrolysis in vivo to the parent molecule. Alternatively an ester of a compound of Formula (Ia) or (Ib) containing a carboxy group may be convertible by hydrolysis in vivo to the parent molecule. Suitable esters of compounds of Formula (Ia) or (Ib) containing a hydroxy group, are for example acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methylsulphonates, ethanesulphonates, benzenesulphonates, p-toluenesulphonates, cyclohexylsulphamates and quinates. Suitable esters of compounds of Formula (Ia) or (Ib) containing a carboxy group, are for example those described by F. J. Leinweber, Drug Metab. Res., 1987, 18, page 379. An especially useful class of esters of compounds of Formula (Ia) or (lb) containing a hydroxy group, may be formed from acid moieties selected from those described by Bundgaard et al., J. Med. Chem., 1989, 32, page 2503-2507, and include substituted (aminomethyl)-benzoates, for example, dialkylamino-methylbenzoates in which the two alkyl groups may be joined together and/or interrupted by an oxygen atom or by an optionally substituted nitrogen atom, e.g. an alkylated nitrogen atom, more especially (morpholino-methyl)benzoates, e.g. 3- or 4-(morpholinomethyl)-benzoates, and (4-alkylpiperazin-1-yl)benzoates, e.g. 3- or 4-(4-alkylpiperazin-1-yl)benzoates.

"Protected derivatives" means derivatives of compounds of Formula (Ia) or (Ib) in which a reactive site or sites are blocked with protecting groups. Protected derivatives of compounds of Formula (Ia) or (Ib) are useful in the preparation of compounds of Formula (Ia) or (Ib) or in themselves may be active cathepsin S inhibitors. A comprehensive list of suitable protecting groups can be found in T. W. Greene, *Protecting Groups in Organic Synthesis,* 3rd edition, John Wiley & Sons, Inc. 1999.

"Therapeutically effective amount" means that amount which, when administered to an animal for treating a disease, is sufficient to effect such treatment for the disease.

"Treatment" or "treating" means any administration of a compound of the present invention and includes:

(1) preventing the disease from occurring in an animal which may be predisposed to the disease but does not yet experience or display the pathology or symptomatology of the disease, (2) inhibiting the disease in an animal that is experiencing or displaying the pathology or symptomatology of the diseased (i.e., arresting further development of the pathology and/or symptomatology), or (3) ameliorating the disease in an animal that is experiencing or displaying the pathology or symptomatology of the diseased (i.e., reversing the pathology and/or symptomatology).

Representative compounds of the Invention where $R^1$, $R^2$, and $R^5$ are hydrogen, $R^4$ is phenylsulfonyl and other groups are as shown in Table 1 below are.

TABLE 1

| Cpd # | Stereochem. at (*C, **C) | R³ | R¹ᵃ | R⁶ | R¹⁰ |
|---|---|---|---|---|---|
| 1 | (S, S) | H | cyclohexylmethyl | $C_2H_5$ | benzoxazol-2-yl |
| 2 | (S, RS) | $CH_3$ | cyclohexylmethyl | $C_2H_5$ | benzoxazol-2-yl |
| 3 | (S, S) | $CH_3$ | cyclohexylmethyl | $C_2H_5$ | benzoxazol-2-yl |
| 4 | (R, S) | H | 2-$OCHF_2$phenyl-methanesulfonylmethyl | $C_2H_5$ | benzoxazol-2-yl |
| 5 | (R, S) | $CH_3$ | 2-$OCHF_2$phenyl-methanesulfonylmethyl | $C_2H_5$ | benzoxazol-2-yl |
| 6 | (S, S) | $CH_3$ | thiazol-2-ylmethyl | $C_2H_5$ | benzoxazol-2-yl |
| 7 | (S, S) | $CH_3$ | 1-methylcyclopentyl-methyl | $C_2H_5$ | benzoxazol-2-yl |
| 8 | (S, S) | morpholino-4-yl | cyclohexylmethyl | $C_2H_5$ | benzoxazol-2-yl |
| 9 | (R, S) | $CH_3$ | 2-$OCHF_2$phenyl-methanesulfonylmethyl | $C_2H_5$ | 5-$C_2H_5$-[1.3.4]oxadiazol-2-yl |
| 10 | (RS, RS) | $CH_3$ | 2-$OCHF_2$phenyl-methanesulfonylmethyl | $C_2H_5$ | 3-phenyl-[1.2.4]oxadiazol-5-yl |

Representative compounds of the Invention where $R^1$ and $R^2$ are hydrogen, $R^4$ is phenylsulfonyl and other groups are as shown in Table 2 below are.

TABLE 2

| Cpd. # | Stereochem. at (*C) | R³ | R¹ᵃ | R⁵ᵃ, R⁶ᵃ | R⁵ᵃ + R⁶ᵃ |
|---|---|---|---|---|---|
| 1 | (S) | H | cyclohexylmethyl | H, H | |
| 2 | (S) | $CH_3$ | cyclohexylmethyl | H, H | |
| 3 | (S) | $CH_3$ | cyclohexylmethyl | | cyclopropyl |
| 4 | (S) | H | cyclohexylmethyl | | cyclopropyl |
| 5 | (RS) | $SCH_3$ | cyclohexylmethyl | H, H | |
| 6 | (R) | H | 2-$OCHF_2$phenyl-methanesulfanylmethyl | H, H | |
| 7 | (R) | H | 2-$OCHF_2$phenyl-methanesulfonylmethyl | H, H | |
| 8 | (S) | $CH_3$ | cyclohexylmethyl | | tetrahydrothiopyran-4-yl |
| 9 | (S) | $CH_3$ | cyclohexylmethyl | | 1,1-dioxotetrahydro-thiopyran-4-yl |
| 10 | (R) | $CH_3$ | 2-$OCHF_2$phenyl-methanesulfanylmethyl | H, H | |
| 11 | (R) | $CH_3$ | 2-$OCHF_2$phenyl-methanesulfonylmethyl | H, H | |
| 12 | (R) | H | phenylmethanesulfonylmethyl | H, H | |
| 13 | (R) | $CH_3$ | 2-$OCHF_2$phenyl-methanesulfonylmethyl | | 1,1-dioxotetrahydro-thiopyran-4-yl |
| 14 | (S) | $CH_3$ | 1-methylcyclopentylmethyl | H, H | |
| 15 | (R) | $CH_3$ | phenylmethanesulfanylmethyl | H, H | |
| 16 | (R) | $CH_3$ | phenylmethanesulfonylmethyl | H, H | |
| 17 | (S) | $CH_3$ | 1-methylcyclopentylmethyl | | tetrahydrothiopyran-4-yl |
| 18 | (S) | $CH_3$ | 1-methylcyclopentylmethyl | | 1,1dioxotetrahydro-thiopyran-4-yl |
| 19 | (S) | $CH_3$ | 1-methylcyclohexylmethyl | | cyclopropyl |

PREFERRED EMBODIMENTS (I) While the broadest scope of this invention is set forth in the Summary of the Invention, certain compounds of Formula (Ia) and (Ib) contained therein and within the preferred embodiment set forth in the Summary of the Invention (i.e., regarding scope of $R^{38}$) are preferred. For example:

A. One preferred group of compounds is that wherein E is —$C(R^5)(R^6)X^1$ in which:
  $R^5$ is hydrogen or alkyl; and
  $R^6$ is hydrogen, alkyl, -(alkylene)-$OR^{12}$ (where $R^{12}$ is hydrogen, alkyl, or haloalkyl), cycloalkyl, cycloalkylalkyl, aryl, aralkyl, heteroaryl, heteroaralkyl, heterocyclyl, heterocyclylalkyl wherein the aromatic or alicyclic ring in aryl, aralkyl, heteroaryl, heteroaralkyl, heterocyclyl or heterocyclylalkyl is optionally substituted with one, two, or three $R^a$ independently selected from alkyl, haloalkyl, alkoxy, hydroxy, haloalkoxy, halo, carboxy, alkoxycarbonyl, amino, monsubstituted amino, disubstituted amino, or acyl.

Preferably, $R^5$ is hydrogen;
$R^6$ is alkyl, preferably ethyl; and
$X^1$ is —CHO, —C(O)$R^{10}$, —C(O)CF$_3$, —C(O)CF$_2$CF$_2$R$^9$, —CH=CHS(O)$_2$R$^{10}$, —C(O)CF$_2$C(O)NR$^{10}$R$^{11}$, —C(O)C(O)NR$^{10}$R$^{11}$, —C(O)CH$_2$OR$^{10}$, —C(O)CH$_2$N(R$^{17}$)SO$_2$R$^{10}$, —C(O)C(O)N(R$^{11}$)(CH$_2$)$_2$OR$^{11}$, —C(O)C(O)N(R$^{11}$)(CH$_2$)$_2$NHR$^{11}$ or —C(O)C(O)R$^{10}$; wherein $R^{10}$ is alkyl, aryl, aralkyl, heteroaryl, heteroaralkyl, cycloalkylalkyl or heterocyclylalkyl wherein the aromatic ring in $R^{10}$ is optionally substituted with $R^d$ selected from heteroaryl, aryl, or alkyl, $R^{11}$ is hydrogen or alkyl and $R^9$ is halo.

Preferably, E is —CHR$^6$C(O)R$^{10}$ where $R^6$ is alkyl, preferably ethyl, propyl, butyl, more preferably ethyl, and $R^{10}$ is heteroaryl optionally substituted with one or two $R^d$ independently selected from alkyl, haloalkyl, alkoxy, cycloalkyl, hydroxy, haloalkoxy, halo, carboxy, alkoxycarbonyl, aryl, heteroaryl, amino, monsubstituted amino, disubstituted amino, or acyl wherein the aromatic or alicyclic ring in $R^d$ is optionally substituted with one, two, or three substitutents independently selected from alkyl, haloalkyl, alkoxy, haloalkoxy, halo, hydroxy, carboxy, alkoxycarbonyl, amino, alkylamino, or dialkylamino, more preferably $R^{10}$ is benzoxazol-2-yl, 4-azabenzoxazol-2-yl, 2-pyridin-3-yl-[1.3.4]-oxadiazol-5-yl, 2-pyridin-4-yl-[1.3.4]-oxadiazol-5-yl, 2-ethyl-[1.3.4]-oxadiazol-5-yl, 2-isopropyl-[1.3.4]-oxadiazol-5-yl, 2-tert-butyl-[1.3.4]-oxadiazol-5-yl, 2-phenyl-[1.3.4]-oxadiazol-5-yl, 2-methoxymethyl-[1.3.4]-oxadiazol-5-yl, 2-furan-2-yl-[1.3.4]-oxadiazol-5-yl, 2-thien-2-yl-[1.3.4]-oxadiazol-5-yl, 2-(4-methoxyphenyl)-[1.3.4]-oxadiazol-5-yl, 2-(2-methoxyphenyl)-[1.3.4]-oxadiazol-5-yl, 2-(3-methoxyphenyl)-[1.3.4]-oxadiazol-5-yl, 2-(2-trifluoromethoxyphenyl)-[1.3.4]-oxadiazol-5-yl, 2-(3-trifluoromethoxyphenyl)-[1.3.4]-oxadiazol-5-yl, 2-(4-trifluoromethoxyphenyl)-[1.3.4]-oxadiazol-5-yl, 2-(4-dimethylaminophenyl)-[1.3.4]-oxadiazol-5-yl, pyradizin-3-yl, pyrimidin-2-yl, 3-phenyl-[1.2.4]-oxadiazol-5-yl, 3-ethyl-[1.2.4]-oxadiazol-5-yl, 3-cyclopropyl-[1.2.4]-oxadiazol-5-yl, 3-thien-3-yl-[1.2.4]-oxadiazol-5-yl, 3-pyridin-4-yl-[1.2.4]-oxadiazol-5-yl, 3-pyridin-2-yl-[1.2.4]-oxadiazol-5-yl, 5-ethyl-[1.2.4]-oxadiazol-3-yl, 5-phenyl-[1,2.4]-oxadiazol-3-yl, 5-thien-3-yl-[1.2.4]-oxadiazol-3-yl, 5-trifluoromethyl-[1.2.4]-oxadiazol-3-yl, 5-pyridin-4-yl-[1.2.4]-oxadiazol-3-yl, or 5-phenyloxazol-2-yl, most preferably benzoxazol-2-yl, 2-ethyl-[1.3.4]-oxadiazol-5-yl, and 3-phenyl-[1.2.4]-oxadiazol-5-yl.

B. Another preferred group of compounds is that wherein E is —C(R$^5$)(R$^6$)X$^1$ in which $R^5$ and $R^6$ taken together with the carbon atom to which both $R^5$ and $R^6$ are attached form cycloalkylene or heterocycloalkylene, preferably cyclopropylene, cyclopentylene, cyclohexylene, thiomorpholinyl-1-dioxide, tetrahydropyran-4-yl, tetrahydrothiopyran-4-yl, tetrahydropyran-4-yl-1-oxide, tetrahydropyran-4-yl,-1,1-dioxide, or piperidin-4-yl wherein the nitrogen atom is optionally substituted with alkyl or hydroxy, preferably tetrahydrothiopyran-4-yl-1,1-dioxide, and $X^1$ is —CHO, —C(O)R$^{10}$, —C(O)CF$_3$, —C(O)CF$_2$CF$_2$R$^9$, CH=CHS(O)$_2$R$^{10}$, —C(O)CF$_2$C(O)NR$^{10}$R$^{11}$, —C(O)C(O)NR$^{10}$R$^{11}$, —C(O)CH$_2$OR$^{10}$, —C(O)CH$_2$N(R$^{11}$)SO$_2$R$^{10}$, —C(O)C(O)N(R$^{11}$)(CH$_2$)$_2$OR$^{11}$, —C(O)C(O)N(R$^{11}$)(CH$_2$)$_2$NR$^1$ or —C(O)C(O)R$^{10}$. More preferably, —C(O)C(O)NR$^{10}$R$^{11}$ where $R^{11}$ is hydrogen and $R^{10}$ is benzyl.

C. Yet another preferred group of compounds is that wherein E is —CH$_2$CN.

D. Yet another preferred group of compounds is that wherein E is —CR$^{5a}$R$^{6a}$CN where $R^{5a}$ and $R^{61}$ together with the carbon atom to which they are attached form cycloalkylene optionally substituted with one or two $R^b$ independently selected from alkyl, halo, dialkylamino, aryl, aralkyl, cycloalkyl, cycloalkylalkyl, heteroaryl, heteroaralkyl, alkoxycarbonyl, or aryloxycarbonyl. Preferably, $R^{5a}$ and $R^{6'}$ together with the carbon atom to which they are attached form cyclopropylene, cyclobutylene, cyclopentylene, or cyclohexylene optionally substituted with groups described immediately above. More preferably, $R^{5a}$ and $R^{6a}$ together with the carbon atom to which they are attached form cyclopropylene, cyclobutylene, cyclopentylene, cyclohexylene, cycloheptylene, 2-methylcyclopropylene, 3-benzylcyclopentylene, 3-cyclohexylmethylcyclopentylene, 3-cyclopentylmethylcyclopentylene, 3-phenylcyclopentylene, 3-cyclohexylcyclopentylene, 3-cyclopentylcyclopentylene, 3-pyridin-2-ylmethylcyclopentylene, 3-pyridin-3-ylmethylcyclopentylene, 3-pyridin-4-ylmethylcyclopentylene, 2-methylcyclopropylene, 2,3-dimethylcyclopropylene, 3-benzylcyclobutylene, 3-methylcyclopentylene, 3,4-dimethylcyclopentylene, 3-ethylcyclopentylene, 3-(1,1-dimethylpropyl)cyclopentylene, 3-n-butylcyclopentylene, 3-ethoxycarbonylcyclopentylene, 3,4-diethoxycarbonyl-cyclopentylene, or 3-benzyl-4-dimethylaminocyclopentylene. Most preferably, cyclopropylene.

E. Yet another preferred group of compounds is that wherein E is —CR$^{5a}$R$^{6a}$CN where $R^{5a}$ is hydrogen or alkyl and $R^{6a}$ are independently selected from the group consisting of alkyl, haloalkyl, carboxyalkyl, alkoxycarbonylalkyl, cycloalkyl, cycloalkylalkyl, aryl, aralkyl, heteroaryl, heteroaralkyl, heterocyclyl, heterocyclylalkyl, cyano, -alkylene-X—R$^{12}$ (where X is —O—, —NR$^{13}$—, —CONR$^{13}$—, —S(O)$_{n1}$—, —NHCO—, —CO—, or —C(O)O— where n1 is 0-2, and $R^{12}$ and $R^{13}$ are independently hydrogen, alkyl, haloalkyl, cycloalkyl, cycloalkylalkyl, aryl, aralkyl, heteroaryl, or heteroaralkyl) wherein the aromatic or alicyclic ring in $R^{6a}$ is optionally substituted with one, two, or three $R^a$ independently selected from alkyl, haloalkyl, alkoxy, hydroxy, haloalkoxy, halo, carboxy, alkoxycarbonyl, amino, monsubstituted amino, disubstituted amino, nitro, aryloxy, benzyloxy, acyl, or arylsulfonyl optionally substituted with alkyl.

Preferably, $R^{5a}$ is hydrogen and $R^{6a}$ is alkyl, haloalkyl, aralkyl, heteroaryl, heteroaralkyl, cycloalkylalkyl, heterocyclylalkyl, alkoxycarbonylalkyl, or -alkylene-X—R$^{12}$ (where X is —O—, —NR$^{13}$—, —CONR$^{13}$—, —S(O)$_{n1}$—, —NHCO—, —CO—, or —C(O)O— where n1 is 0-2, and $R^{12}$ and $R^{13}$ are independently hydrogen, alkyl, haloalkyl, cycloalkyl, cycloalkylalkyl, aryl, aralkyl, heteroaryl, or heteroaralkyl) wherein the aromatic or alicyclic ring in $R^{6a}$ is optionally substituted with one, two, or three $R^a$ independently selected from alkyl, haloalkyl, alkoxy, hydroxy, haloalkoxy, halo, nitro, aryloxy, benzyloxy, carboxy, alkoxycarbonyl, amino, monsubstituted amino, disubstituted amino, or acyl and wherein the alkylene chain in alkyleneS-R$^{12}$ is one to three carbon atoms. Even, more preferably $R^{6a}$ is 2-phenethyl, benzyloxymethyl, phenylmethanesulfanylmethyl, 3-phenylpropyl, benzyl, 2-chlorobenzyloxymethyl, phenylmethanesulfonylmethyl, 3-methoxybenzyloxymethyl, 4-methoxyphenylmethanesulfanylmethyl, 4-methylphenylmethanesulfanylmethyl, 4-chlorobenzyloxymethyl, 2-methylbenzyloxymethyl, 3-methylbenzyloxymethyl, 3-methoxycarbonylbenzyloxymethyl, 4-methoxycarbonylbenzyloxymethyl, 2-tert-butoxycarbonylethyl, 2-chlorobenzyl, 4-chlorobenzyl, 3,4-dichlorobenzyl, phenyl, pyridin-4-yl, pyridin-3-yl, methoxymethyl, pyridin-3-ylmethyl, pyridin-4-ylmethyl, thiazol-4-ylmethyl, 2-cyclohexylethyl, 3-cyclohexylpropyl, piperidin-1-ylmethyl, 2-piperidin-1-ylethyl, 3-piperidin-1-ylpropyl, 1-methylpiperidin-4-ylmethyl, 2-(4-methylpiperidin-4-yl)ethyl, pyrrolidin-1-ylmethyl, 2-pyrrolidin-1-ylethyl, 3-pyrrolidin-1-ylpropyl, 2-tetrahydrothiopyran-4-ylethyl, 2-tetrahydropyran-4-ylethyl, tetrahydropyran-2-ylmethyl, tetrahydrothiopyran-4-methyl, 3-tetrahydropyran-4-ylpropyl, 3-tetrahydrothiopyran-4-ylpropyl, 4-cyclohexylbutyl, N-benzyl-N-methylaminomethyl, N-cyclohexylmethyl-N-methylaminomethyl, 2,2,3,3,3-pentafluoropropyl, thien-2-yl, 4-phenylcarbonylaminobutyl, cyclohexyloxymethyl, cyclohexylmethyloxymethyl, N-cyclohexyl-N-methylaminomethyl, pyridin-4-ylmethoxymethyl, 2-methylpropyl, 2,2-dimethylpropyl, 3,3-dimethylbutyl, 3-methylbutyl, morpholin-4-ylmethyl, thiomorpholin-4-ylmethyl, 3-morpholin-4-ylpropyl, 3-thiomorpholin-4-ylpropyl, 3-(4-methylpiperidin-1-yl)propyl, n-propyl, ethoxymethyl, ethylthiomethyl, 2-methylthioethyl, ethylsulfinylmethyl, 2-ethylsulfonylethyl, 2-methylsulfinylethyl, 4-dimethylaminobutyl, 2-N,N-dimethylaminocarbonylethyl, N,N-dimethylaminocarbonylmethyl, methoxycarbonylmethyl, indol-3-ylmethyl, 1-methylindol-3-ylmethyl, 1-ethylindol-3-ylmethyl, 1-(4-methylphenylsulfonyl)indol-3-ylmethyl, 1-benzyloxyethyl, 2-(4-hydroxyphenyl)ethyl, benzyloxycarbonylmethyl, 2-(benzyloxycarbonyl)ethyl, 4-nitrobenzyl, 4-benzyloxybenzyl, 3-chlorobenzyl, 4-benzoylbenzyl, 2-methylsulfonylethyl, naphth-1-ylmethyl, cyclopropylmethyl, cyclohexylmethyl, thien-2-ylmethyl, naphth-2-ylmethyl, 4-hydroxy-3-iodobenzyl, 4-hydroxybenzyl, indol-1-ylmethyl, 2-indol-1-ylethyl, 3-indol-1-ylpropyl, cycloheptylmethyl, or 3-cycloheptylpropyl.

F. Yet another preferred group of compounds is that wherein E is —CR$^{5a}$R$^{6a}$CN where R$^{5a}$ and R$^{6a}$ together with the carbon atom to which they are attached form heterocycloalkylene optionally substituted with one to four R$^c$ which are independently selected from alkyl, haloalkyl, hydroxyalkyl, alkoxyalkyl, alkoxyalkyloxyalkyl, aryloxyalkyl, heteroaryloxyalkyl, aminoalkyl, acyl, aryl, aralkyl, heteroaryl, heteroaralkyl, heterocyclyl, heterocyclylalkyl, cycloalkyl, cycloalkylalkyl, —S(O)$_{n2}$R$^4$, -alkylene-S(O)$_{n2}$—R$^5$, —COOR$^{16}$, -alkylene-COOR$^{17}$, —CONHR$^{18}$R$^{19}$, or -alkylene-CONHR$^{20}$R$^{21}$ (where n2 is 0-2 and R$^{14}$-R$^{17}$, R$^{18}$ and R$^{20}$ are independently hydrogen, alkyl, haloalkyl, aryl, aralkyl, heteroaryl, heteroaralkyl, cycloalkyl, cycloalkylalkyl, or heterocyclyl and R$^{19}$ and R$^{21}$ are independently hydrogen or alkyl) wherein the aromatic or alicyclic ring in the groups attached to heterocycloalkylene is optionally substituted with one, two, or three substituents independently selected from alkyl, haloalkyl, alkoxy, hydroxy, haloalkoxy, halo, carboxy, alkoxycarbonyl, amino, monsubstituted amino, disubstituted amino, or acyl. Preferably, R$^{5a}$ and R$^{6a}$ together with the carbon atom to which they are attached form pyrrolidinyl, piperidinyl, tetrahydropyranyl, tetrahydrothiopyranyl, tetrahydrofuranyl, tetrahydrothiopyran-4-yl-1-oxide, tetrahydrothiopyran-4-yl-1,1-dioxide, hexahydropyridmidinyl, or hexahydropyridazinyl optionally substituted as described above. More preferably, R$^{5a}$ and R$^{6a}$ together with the carbon atom to which they are attached form piperidin-4-yl substituted with one or two alkyl, haloalkyl, aminoalkyl, alkoxyalkyl, alkoxyalkyloxyalkyl, heterocyclyl, heterocyclylalkyl, -alkylene-CONHR$^{20}$R$^{21}$, or cycloalkyl. Most preferably, R$^{5a}$ and R$^{6a}$ together with the carbon atom to which they are attached form piperidin-4-yl optionally substituted at the 1-position with methyl, ethyl, propyl, n-butyl, n-pentyl, 3-dimethylaminopropyl, 4-dimethylaminobutyl, 3-morpholin-4-ylpropyl, 3-piperidin-1-ylpropyl, 3-(4-methylpiperazin-1-yl)propyl, 3-(1-methylpiperidin-4-yl)propyl, 4-morpholin-4-ylbutyl, 2-(2-methoxyethyloxy)ethyl, 4-methoxybutyl, 4-aminocarbonylbutyl, 3-aminocarbonylpropyl, morpholin-4-yl, 4-methylpiperazin-1-yl, 1-ethoxycarbonylpiperidin-4-yl, 1,1-dioxotetrhydrothiopyran-4-yl, hydroxy, 2,2,2-trifluoroethyl, or tert-butyl, 1,2-dimethylpiperidin-4-yl, 1,2,6-trimethylpiperidin-4-yl, 1,2,2-trimethylpiperidin-4-yl, 1-methyl-2-oxopiperidin-4-yl, 1-methylpiperidin-3-yl, 1-tert-butoxycarbonylpiperidin-4-yl, 1-cyclohexylpiperidin-4-yl, 1-cyclopropylmethylpyrrolidin-3-yl, 1-benzylpyrrolidin-3-yl, 1-benzyloxycarbonylpyrrolidin-3-yl, pyrrolidin-3-yl, 1-hydroxypyrrolidin-3-yl, 1-methylpyrrolidin-3-yl, 1-ethypyrrolidin-3-yl, 1-n-propyl or n-butylpyrrolidin-3-yl, 1-cyclohexylpyrrolidin-3-yl, 1-ethyl-2,2-dimethylpyrrolidin-4-yl, 1-propyl-2-methoxycarbonylpiperidin-4-yl, 2-oxopyrrolidin-3-yl, 1-ethyl-2-oxopyrrolidin-3-yl, morpholin-4-yl, 1-(1-methylpiperidin-4-ylcarbonyl)piperidin-4-yl, 1-ethoxycarbonylpiperidin-4-yl, 1-benzylazetidin-3-yl, tetrahydrothiopyran-4-yl-1-oxide, or tetrahydrothiopyran-4-yl-1,1-dioxide. Particularly preferably, R$^{5a}$ and R$^{6a}$ together with the carbon atom to which they are attached form piperidin-4-yl optionally substituted at the 1-position with methyl, ethyl, 2-propyl, or cyclopropyl, tetrahydrothiopyran-4-yl, tetrahydrothiopyran-4-yl-1-oxide, or tetrahydrothiopyran-4-yl-1,1-dioxide.

G. Yet another preferred group of compounds is that wherein E is a group of formula (a):

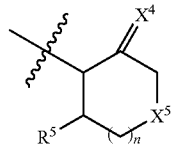

in which:

n is 0, 1, or 2, X$^4$ is —N$^{22}$—, —O— or —S— where R$^{22}$ is hydrogen, alkyl, or alkoxy; X$^5$ is —O—, —S(O)$_2$—, —S— or NR$^{23}$ where R$^{23}$ is selected from hydrogen, alkyl, —S(O)$_2$R$^{24}$, —C(O)OR$^{26}$, or acyl where R$^{24}$ is alkyl, haloalkyl, cycloalkyl, cycloalkylalkyl, heterocyclyl, heterocyclylalkyl, aryl, aralkyl, heteroaryl, or heteroaralkyl and R$^{26}$ is hydrogen or alkyl. Preferably, X$^4$ is —O—, n is 0 or 1, and X$^5$ is —O—.

(a) Within the above preferred and more preferred groups contained within (A-G), an even more preferred group of compounds is that wherein:

R$^{1a}$ is alkyl, cycloalkyl, aralkyl, heteroaralkyl, cycloalkylalkyl, heterocyclylalkyl, or -alkylene-X$^2$—R$^{32}$ [wherein X$^2$ is —NR$^{33}$—, —O—, —S(O)$_{n4}$, —CO—, —COO—, —OCO—, —NR$^{33}$CO—, —CONR$^{33}$—, —NR$^{33}$SO$_2$—, —SO$_2$NR$^{33}$—, —NR$^{33}$COO—, —OCONR$^{33}$—, —NR$^{33}$CONR$^{34}$, or —NR$^{33}$SO$_2$NR$^{34}$— (where R$^{33}$ and R$^{34}$ are independently hydrogen, alkyl, or acyl and n4 is 0-2) and R$^{32}$ is hydrogen, alkyl, haloalkyl, cycloalkyl, cycloalkylalkyl, heterocyclyl, aryl, aralkyl, heteroaryl, heteroaralkyl, heterocyclyl, or heterocyclylalkyl] wherein said alkylene chain is optionally substituted with one to six halo and wherein the aromatic or alicyclic ring in R$^{1a}$ is optionally substituted with one, two, or three R$^e$ independently selected from alkyl, haloalkyl, alkoxy, hydroxy, haloalkoxy, halo, nitro, cyano, carboxy, alkoxycarbonyl, aryl, heteroaryl, cycloalkyl, cycloalkylalkyl, aralkyl, heteroaralkyl, amino, monsubstituted amino, disubstituted amino, or acyl.

Preferably, $R^{1a}$ is 2-methylpropyl, 2,2-dimethylpropyl, 4,4-dimethylcyclohexylmethyl, 4-ethyl-4-methylcyclohexylmethyl, 4,4-diethylcyclohexylmethyl, 3,3-dimethylcyclohexylmethyl, 3,5-dimethylcyclohexylmethyl, 1-ethoxycarbonylpiperidin-4-ylmethyl, 1-methylpiperidin-4-ylmethyl, cycloheptylmethyl, cyclooctylmethyl, 3,3-dimethylbutyl, 3-methylbutyl, 2-cyclohexylethyl, 2,2,3-trimethylbutyl, 2-cyclohexyl-2-methylpropyl, 3,3-dimethylpentyl, 3-ethyl-3-methylpentyl, 2-(1-methylcyclohexyl)ethyl, tetrahydronaphthylmethyl, 2-tetrahydropyran-4-ylethyl, 2-(1-methylcyclopropyl)ethyl, 2-(1-methylcyclopropyl)-2-methylpropyl, 2-cyclopentylethyl, 2-cyclopentyl-2-methylpropyl, 4-isopropyl-4-methylcyclohexylmethyl, phenylmethanethiomethyl, phenylmethanesulfinylmethyl, dimethylaminomethyl, pyrrolidin-1-ylmethyl, piperidin-1-ylmethyl, morpholin-4-ylmethyl, thiomorpholin-4-ylmethyl, 1-oxo-thiomorpholin-4-ylmethyl, 1,1-dioxothiomorpholin-4-ylmethyl, tetrahydrothiopyran-4-ylmethyl, 1-oxotetrahydrothiopyran-4-ylmethyl, 1,1-dioxotetrahydrothiopyran-4-ylmethyl, 1-methylpiperazin-4-ylmethyl, benzyloxymethyl, n-butyl, ethoxymethyl, ethylthiomethyl, ethylsulfiylmethyl, ethylsulfonylmethyl, isopropylthiomethyl, isopropyloxymethyl, 2-dimethylaminoethyl, 2-piperidin-1-ylethyl, 2-pyrrolidin-1-ylethyl, 2-methylthioethyl, 2-methylsulfinylethyl, 2-methysulfonylethyl, tert-butylthiomethyl, tert-butyloxymethyl, benzyl, 4-methoxybenzyl, imidazol-4-ylmethyl, 4-dimethylaminobutyl, indol-3-ylmethyl, 2-dimethylaminocarbonylethyl, 2-pyrrolidin-1-ylcarbonylethyl, dimethylaminocarbonylmethyl, pyrrolidin-1-ylcarbonylmethyl, methoxycarbonylmethyl, 2-fluorophenylmethanesulfonylmethyl, 2-chlorophenylmethanesulfonylmethyl, 2-nitrophenylmethanesulfonylmethyl, 2-cyanophenylmethanesulfonylmethyl, pyridin-3-ylmethanesulfonylmethyl, pyridin-2-ylmethanesulfonylmethyl, pyridin-4-ylmethanesulfonylmethyl, 2-fluorophenylmethanethiomethyl, 2-chlorophenylmethanethiomethyl, 2-cyanophenylmethanethiomethyl, 2-nitrophenylmethanethiomethyl, cyclohexylmethanethiomethyl, cyclohexylsulfinylthiomethyl, cyclohexylmethanesulfonylmethyl, 3,4-dichlorobenzyl, 2-chlorobenzyl, 4-ethoxybenzyl, 4-nitrobenzyl, biphen-4-ylmethyl, naphth-1-ylmethyl, 2-methylbutyl, 1-methylpropyl, naphth-2-ylmethyl, 4-chlorobenzyl, 3-chlorobenzyl, 4-fluorobenzyl, indol-2-ylmethyl, 1-benzylimidazol-4-ylmethyl, 2-phenethyl, 4-hydroxybenzyl, 2-(4-hydroxyphenyl)ethyl, 4-ethyl-4-methylpiperidin-1-ylmethyl, 2-methylcyclohexylmethyl, 4-methoxycyclohexylmethyl, indol-1-ylmethyl, 1-methylpiperidin-2-ylmethyl, 2-bicyclo[2.2.1]hep-3-tylethyl, 8-methyl-8-aza-bicyclo[3.2.1]oct-3-ylmethyl, bicyclo[3.2.1]oct-3-ylmethyl, bicyclo[3.1.1]hept-3-ylmethyl, 6,6-dimethylbicyclo[3.1.1]hept-3-ylmethyl, 6,6-dimethylbicyclo[3.1.1]hept-4-ylmethyl, 2-bicyclo[2.2.1]hept-1-ylethyl, bicyclo[2.2.1]hept-2-ylethyl, thiophene-2-sulfonylmethyl, 3-chloro-2-fluorophenylmethane-sulfonylmethyl, benzenesulfonylmethyl, phenylmethanesulfonylmethyl, 2-benzenesulfonylethyl, 2-(pyridin-2-ylsulfonyl)ethyl, 2-(pyridin-4-ylsulfonyl)ethyl, 2-phenylmethanesulfonyl-ethyl, oxypyridin-2-ylmethanesulfonylmethyl, 4-methoxyphenyl-methanesulfonylmethyl, p-tolylmethanesulfonylmethyl, 4-chlorophenylmethanesulfonylmethyl, o-tolylmethanesulfonylmethyl, 3,5-dimethylphenylmethanesulfonylmethyl, 4-trifluoromethylphenylmethanesulfonylmethyl, 4-trifluoromethoxyphenylmethanesulfonylmethyl, 2-bromophenylmethanesulfonylmethyl, naphth-2-ylmethanesulfonylmethyl, 3-methylphenylmethanesulfonylmethyl, 3-trifluoromethylphenylmethanesulfonylmethyl, 3-trifluoromethoxyphenylmethane-sulfonylmethyl, 4-fluoro-2-trifluoromethoxyphenylmethanesulfonylmethyl, 2-fluoro-6-trifluoromethylphenylmethanesulfonylmethyl, 2,6-difluorobenzyl, 1-methylcyclopentylmethyl, cyclohexyl, pyridin-4-ylmethyl, 3-chlorophenylmethanesulfonylmethyl, 2-trifluoromethylphenylmethanesulfonylmethyl, 4-tert-butylphenylmethanesulfonylmethyl, 2-fluoro-3-methylphenylmethanesulfonyl-methyl, 3-fluorophenylmethanesulfonylmethyl, 4-fluorophenylmethanesulfonylmethyl, 2,5-difluorophenylmethanesulfonylmethyl, 2,6-difluorophenylmethanesulfonylmethyl, 2,5-dichlorophenylmethanesulfonylmethyl, 3,4-dichlorophenylmethanesulfonylmethyl, 2-(1,1-difluoromethoxy)phenylmethanesulfonylmethyl, 3-cyanophenylmethane-sulfonylmethyl, 2-trifluoromethoxyphenylmethanesulfonylmethyl, 3-trifluoromethoxyphenylmethanesulfonylmethyl, 2,3-difluorophenylmethane-sulfonylmethyl, 2,5-difluorophenylmethanesulfonylmethyl, biphenyl-2-ylmethane-sulfonylmethyl, cyclohexylmetthyl, 3-fluorophenyl-methanesulfonylmethyl, 2-pyridin-2-ylsulfonylethyl, 2-phenylsulfonylethyl, 2,2-difluoro-3-phenylpropyl, 2,2-dichloro-3-phenylpropyl, 2,2,2-trichloroethyl, 2,2-dichloroethyl, 1,4-dimethylcyclopentylmethyl, 3,4-difluorophenylmethanesulfonylmethyl, 2,4-difluorophenylmethanesulfonylmethyl, 2,4,6-trifluorophenylmethanesulfonylmethyl, 2,4,5-trifluorophenylmethanesulfonylmethyl, 2,3,4-trifluorophenylmethanesulfonylmethyl, 2,3,5-trifluorophenylmethanesulfonylmethyl, 2,5,6-trifluorophenylmethanesulfonyl-methyl, 2-chloro-5-trifluoromethylphenylmethanesulfonylmethyl, 2-methylpropane-1-sulfonylmethyl, 2-fluoro-3-trifluoromethylphenylmethanesulfonyhnethyl, 2-fluoro-4-trifluoromethylphenylmethanesulfonylmethyl, 2-fluoro-5-trifluoromethyl-phenylmethanesulfonylmethyl, 4-fluoro-3-trifluoromethylphenylmethanesulfonylmethyl, 2-methoxyphenylmethanesulfonylmethyl, 3,5-bis-trifluoromethylphenyl-methanesulfonylmethyl, 4-difluoromethoxyphenylmethanesulfonylmethyl, 3-difluoromethoxyphenylmethanesulfonylmethyl, 2,6-dichlorophenyhnethanesulfonylmethyl, biphenyl-4-ylmethanesulfonylmethyl, 3,5-dimethylisoxazol-4-ylmethanesulfonylmethyl, 5-chlorothien-2-ylmethanesulfonylmethyl, 2-[4-(1,1-difluoromethoxy)benzenesulfonyl]ethyl, 2-[2-(1,1-difluoromethoxy)benzenesulfonyl]ethyl, 2-[3-(1,1-difluoromethoxy)benzenesulfonyl]ethyl, 2-(4-trifluoromethoxybenzenesulfonyl)ethyl, 2-(3-trifluoromethoxybenzenesulfonyl)-ethyl, 2-(2-trifluoromethoxybenzenesulfonyl)-ethyl, (cyanomethylmethylcarbamoyl)methyl, biphenyl-3-ylmethyl, 2-oxo-2-pyrrolidin-1-ylethyl, 2-benzenesulfonylethyl, isobutylsulfanylmethyl, 2-phenylsulfanylethyl, cyclohexylmethanesulfonylmethyl, 2-cyclohexylethanesulfonyl, benzyl, naphth-2-yl, phenylmethanesulfanylmethyl, 2-trifluoromethylphenylmetahnesulfanylmethyl, phenylsulfanylethyl, cyclopropylmethanesulfonylmethyl, 2-methylpropylsulfonylmethyl, 5-bromothien-2-ylmethyl, 3-phenylpropyl, 2,2-difluoro-3-phenylpropyl, 3,4,5-trimethoxy-phenylmethanesulfonyl-methyl, 2,2-difluoro-3-thien-2-ylpropyl, cyclohexylethyl, cyclohexylmethyl, cyclopentylmethyl, tert-butylmethyl, 1-methylcyclohexylmethyl, 1-methylcyclopentylmethyl, 2,2-difluoro-3-phenylpropyl, 2,2-dimethyl-3-phenylpropyl, 1-benzylcyclopropylmethyl, or benzyloxymethyl.

More preferably, $R^{1a}$ is cyclohexyl, 2-cyclohexylethyl, cyclohexylmethyl, tert-butylmethyl, 1-methylcyclohexylmethyl, 1-methylcyclopentylmethyl, 2,2-difluoro-3-phenylpropyl, 2,2-dichloro-3-phenylpropyl, 2,2,2-trichloroethyl, 2,2-dichloroethyl, 1,4-dimethylcyclopentylmethyl, 2,2-dimethyl-3-phenylpropyl, 1-benzylcyclopropylmethyl, 2-(1,1-difluoromethoxy)phenyl-methanesulfonylmethyl, 2-(1,1-difluoromethoxy)phenylmethaneoxymethyl, pyridin-4-ylmethyl, phenylmethanesulfonylmethyl, pyridin-2-ylmethanesulfonylmethyl, pyridin-4-ylmethanesulfonylmethyl, 2-methylpropylsulfonylmethyl, cyclopropylmethanesulfonylmethyl, pyridin-3-ylmethanesulfonylmethyl, 2,6-difluorophenylmethanesulfonylmethyl, 2-pyridin-2-ylsulfonylethyl, 2-phenylsulfonylethyl, benzyloxymethyl, 2,2-dimethylpropyl, cyclopentylmethyl, morpholin-4-ylmethyl, 5-bromothien-2-ylmethyl, pyridin-4-ylmethyl, 2-chlorobenzyl, or 4-fluorobenzyl; and $R^1$ is hydrogen.

(b) Yet another more preferred group of compounds within groups (A-F) is that wherein $R^1$ and $R^{1a}$ together with the carbon atoms to which they are attached form cyclohexylene or heterocycloalkylene, preferably 3,3-dimethylcyclobutyl, cyclohexyl, cyclopentyl, cyclooctyl, tetrahydrothiopyran-1,1-dioxide, or piperidin-4-yl wherein the nitrogen atom at the 1-position of the piperidinyl ring is optionally substituted with $R^f$ where $R^f$ is alkyl or —SO$_2$R where is alkyl, cycloalkyl, cycloalkylalkyl, aryl, aralkyl, heteroaryl or heteroaralkyl where the rings in $R^f$ are optionally substituted with one, two, or three substitutents independently selected from alkyl, alkoxy, haloalkyl, haloalkoxy, hydroxy, halo, or carboxy.

(1) Within the above preferred, more preferred, and even more preferred groups above, a particularly preferred group of compounds is that wherein:

$R^3$ is hydrogen, alkyl, cycloalkyl, phenyl, benzyl, naphthyl, alkylSO$_2$alkyl, cycloalkylSO$_2$alkyl, arylSO$_2$alkyl, pyrrolidinyl, piperidinyl, morpholinyl, thiomorpholinyl, piperazinyl, indolinyl, pyranyl, thiopyranyl, furanyl, thienyl, pyrrolyl, oxazolyl, thiazolyl, imidazolyl, pyridinyl, isoxazolyl, pyrimidinyl, pyrazinyl, pyridazinyl, indolyl, quinolinyl, benzofuranyl, benzthienyl, benzimidazolyl, benzthiazolyl, benzoisoxazolyl, benzoxazolyl or amino; wherein the aromatic or alicyclic ring in $R^3$ is optionally substituted by one, two, or three $R^g$;

each $R^g$ is independently alkyl, halo, hydroxy, oxo, carboxy, cyano, nitro, carboxamide, cycloalkyl, phenyl, naphthyl, pyrrolidinyl, piperidinyl, morpholinyl, thiomorpholinyl, piperazinyl, furanyl, thienyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl, quinoxalinyl, alkoxy, —COR (where R is alkyl), —OC(O)R (where R is alkoxy or aryl), aryloxy, benzyloxy, alkoxycarbonyl, aryloxycarbonyl, carbamoyl wherein the nitrogen atom may be independently mono or di-substituted by alkyl, aryl, pyrrolidinyl, piperidinyl, morpholinyl, thiomorpholinyl, piperazinyl, furanyl, thienyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, alkylthio, arylthio, alkylsulfinyl, alkylsulfonyl, arylsulfinyl, arylsulfonyl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, pyrrolidinyl, piperidinyl, morpholinyl, thiomorpholinyl, piperazinyl, furanyl, thienyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, where the aromatic or alicyclic rings in $R^g$ may be further optionally substituted by one, two or three $R^h$ independently selected from alkyl, alkoxy, haloalkyl, haloalkoxy, halo, hydroxy, carboxy, carboxamido, cyano, nitro, aryl or cycloalkyl;

$R^2$ is hydrogen or methyl;

$R^4$ is as defined in the Summary of the Invention; and $R^{4a}$ is hydrogen, alkyl, cycloalkyl, aryl, alkoxy, or hydroxy.

Preferably, $R^3$ is hydrogen, methyl, ethyl, isopropyl, cyclopropyl, cyclopentyl, cyclohexyl, phenyl, benzyl, naphthyl, pyrrolidinyl, piperidinyl, morpholinyl, thiomorpholinyl, piperazinyl, furanyl, thienyl, thiazolyl, imidazolyl, pyridinyl, pyrazinyl, or amino wherein the aromatic or alicylic rings in $R^3$ are optionally substituted with one, two, or three $R^g$ independently selected from methyl ethyl, fluoro, chloro, bromo, iodo, hydroxy, oxo, carboxy, cyano, nitro, carboxamide, cyclopropyl, phenyl, pyrrolidinyl, piperidinyl, morpholinyl, thiomorpholinyl, piperazinyl, thienyl, imidazolyl, methoxy, acetyl, acetoxy, phenoxy, benzyloxy, methoxycarbonyl, phenoxycarbonyl, carbamoyl wherein the nitrogen atom is mono or disubstituted independently with methyl, ethyl or phenyl, methylthio, phenylthio, phenylsulfonyl, methylsulfonyl, methoxycarbonylamino, phenoxycarbonylamino, methylcarbamoyloxy, phenylcarbamoyloxy, methylsulfonylamino, phenylsulfonylamino, methylaminosulfonyl, phenylaminosulfonyl, amino wherein the nitrogen atom is mono or disubstituted independently with methyl or phenyl wherein the aromatic or alicyclic rings in $R^g$ are further optionally substituted with one, two, or three $R^h$ independently selected from methyl, cyclopropyl, phenyl, methoxy, fluoro, chloro, hydroxy, carboxy, or carboxamido.

Even more preferably, $R^3$ is hydrogen, methyl, ethyl, isopropyl, cyclopropyl, cyclohexyl, phenyl, naphthyl, benzyl, pyrrolidinyl, piperidinyl, morpholinyl, thiomorpholinyl, furanyl, thienyl, thiazolyl, imidazolyl, pyridinyl, pyrazinyl or amino wherein the aromatic or alicyclic rings in $R^3$ are optionally substituted with one, two, or three $R^g$ independently selected from methyl, fluoro, chloro, phenyl, thienyl, methoxy, acetyl, acetoxy, phenoxy, benzyloxy, methoxycarbonyl, carbamoyl wherein the nitrogen atom is mono or disubstituted independently with methyl or phenyl, methylthio, phenylthio, phenylsulfonyl, methylsulfonyl, methoxycarbonylamino, methylcarbamoyloxy, phenylcarbamoyloxy, methylsulfonylamino, phenylsulfonylamino, amino wherein the nitrogen atom is mono or disubstituted independently with methyl or phenyl where the aromatic or alicyclic ring in $R^g$ is optionally substituted with one, two, or three $R^h$ independently selected from methyl, cyclopropyl, phenyl, methoxy, fluoro, chloro, hydroxy, carboxy, or carboxamido. Most preferably, $R^3$ is hydrogen, isopropyl, benzyloxy, cyclohexyl, phenyl, 4-methoxyphenyl, 4-chlorophenyl, 4-fluorophenyl, 2-fluorophenyl, 2-fluoro-4-chlorophenyl, naphthyl, methyl, piperidinyl, morpholinyl, furanyl, thienyl, pyridin-4-yl, pyrazinyl, methylamino, ethylamino, dimethylamino or diethylamino. Particularly preferably $R^3$ is hydrogen or methyl;

$R^{4a}$ is hydrogen, alkyl or alkoxy; preferably, hydrogen; and $R^4$ is —S(O)$_2$R$^{38}$ where $R^{38}$ is phenyl or naphthyl optionally substituted with one, two, or three $R^i$ independently selected from alkyl, alkoxy, halo, haloalkyl, haloalkoxy, hydroxy, alkylthio, alkylsulfonyl, aminosulfonyl, acyl, amino, monosubstituted amino, disubstituted amino, hydroxyalkyl, alkoxyalkyl, aminoalkyl, aryl, heteroaryl, or heterocyclyl where the aromatic or alicyclic ring in $R^i$ is optionally substituted with one or two substituents independently selected from alkyl, halo, alkoxy, haloalkyl, haloalkoxy, hydroxy, amino, alkylamino, dialkylamino, carboxy, or alkoxycarbonyl. Preferably, $R^4$ is phenylsulfonyl.

H. Another preferred group of compounds of Formula (Ia) or (Ib) is that where $R^4$ is $-S(O)_2R^{38}$ where $R^{38}$ is phenyl or naphthyl optionally substituted with one, two, or three $R^i$ independently selected from alkyl, alkoxy, halo, haloalkyl, haloalkoxy, hydroxy, alkylthio, alkylsulfonyl, aminosulfonyl, acyl, amino, monosubstituted amino, disubstituted amino, hydroxyalkyl, alkoxyalkyl, aminoalkyl, aryl, heteroaryl, or heterocyclyl where the aromatic or alicyclic ring in $R^i$ is optionally substituted with one or two substituents independently selected from alkyl, halo, alkoxy, haloalkyl, haloalkoxy, hydroxy, amino, alkylamino, dialkylamino, carboxy, or alkoxycarbonyl. Preferably, $R^4$ is phenylsulfonyl. Within this group, more preferred groups are those where $R^1$, $R^{1a}$, $R^2$-$R^4$ and $R^{4a}$ are as described in in preferred embodiments above. Within the preferred and more preferred groups, an even more preferred group of compounds is that wherein E is as defined in Groups (A-G) above.

I. Another preferred group of compounds of Formula (Ia) or (Ib) is that wherein:

$R^1$, $R^2$, and $R^{4a}$ are hydrogen;

$R^{1a}$ is cycloalkylalkyl wherein the alicyclic ring is optionally substituted with alkyl, heteroaralkyl, or -alkylene-$S(O)_{n4}$—$R^{32}$ where n4 is 0 to 2 and $R^{32}$ is aralkyl where the aromatic ring is optionally substituted with haloalkoxy;

$R^3$ is hydrogen, alkyl, heterocyclyl, or alkylthio;

$R^4$ is phenylsulfonyl;

E is —$CHR^6COR^{10}$ where $R^6$ is alkyl and $R^{10}$ is heteroaryl optionally substituted with alkyl or aryl, —$CH_2CN$, or —$CR^{5a}R^{6a}$ where $R^{5a}$ and $R^{6a}$ together with the carbon atom to which they are attached form cycloalkylene or heterocycloalkylene; or a pharmaceutically acceptable salt thereof.

A person skilled in the art will recognize that a compound in this group can tautomerize to give a compound of Formula (Ib) where $R^{4a}$ is hydrogen. The amount of each tautomer present will depend on various conditions such as steric hinderance, pH, temperature, and the like. Accordingly, this group encompasses individual tautomeric forms of compounds of Formula (Ia) as well as mixtures thereof.

Reference to the preferred embodiments set forth above is meant to include all combinations of particular and preferred groups unless stated otherwise.

General Synthetic Scheme

Compounds of this invention can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "*Protective Groups in Organic Chemistry*" John Wiley and Sons, 1999.

Compounds of Formula (Ia) where E is —$C(R^5)(R^6)X^1$ or —$C(R^{5a})(R^{6a})CN$ and $R^1$, $R^{1a}$, $R^2$, $R^3$, $R^4$, $R^5$, $R^{5a}$, $R^6$ and $R^{6a}$ are as defined in the Summary of the Invention can be prepared by proceeding as in the following Reaction Scheme 1 below.

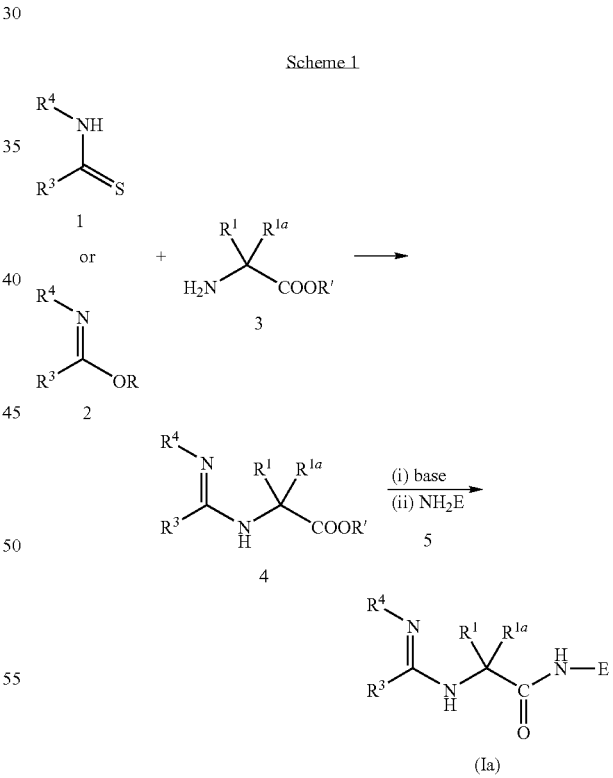

Compounds of Formula (Ia) can be prepared by reacting an amino acid of formula 3 where R' is alkyl, with a thione of formula 1 to give a compound of formula 4. The reaction is carried out in the presence of a suitable coupling agent such as 2-chloro-1-methylpyridinium iodide (Yong, Y. F, et. al., *J. Org. Chem.* 1997, 62, 1540), phosgene or triphosgene (Barton, D. H., et. al., *J. Chem. Soc. Perkin Trans. I*, 1982, 2085), alkyl halides (Brand, E and Brand, F. C., *Org. Synth.*, 1955, 3, 440), or carbodiimide (Poss, M. A., et. al., *Tet. Lett.*, 1992, 40, 5933).

Alternatively, a compound of formula 4 is prepared by reacting a compound of formula 2 with an amino acid of formula 3. The reaction is carried out optionally in the presence of a base such as triethylamine. Suitable reaction conditions are known to those skilled in the art and examples of such amine additions can be found in the art e.g., Haake, M., et. al., *Synthesis*, 1991, 9, 753; Dauwe, C., et al, *Synthesis*, 1995, 2, 171, Reid, et. al., *Justus Liebigs Ann. Chemn.*, 1966, 97, 696; and Dean N. D., and Papadopoulos, E. P. *J. Het. Chem.*, 1982, 19, 1117.

Compounds 1, 2 and 3 are commercially available or they can be prepared by methods well known in the art. For example, a compound of formula 1 where $R^3$ is phenyl, 4-methoxyphenyl, or 4-fluorophenyl and $R^4$ is as defined in the Summary of the invention can be readily prepared by reacting commercially available thiobenzamide, 4-fluorothiobenzamide and 4-methoxythiobenzamide respectively, with $R^{38}SO_2L$ where L is a suitable leaving group such as halo, under conditions well known in the art (e.g., see U.S. Pat. No. 6,136,844 the disclosure of which is incorporated herein by referenced in its entirety). For example, a compound of formula 1 where $R^3$ is phenyl and $R^4$ is $—SO_2R^{38}$ can be prepared by reacting thiobenzamide with $R^{38}SO_2Cl$ in the presence of a base such as triethylamine, pyridine, and the like and in a suitable organic solvent such as tetrahydrofuran, dioxane, dichloromethane, and the like.

Compounds of formula 2 are either commercially available or they can be prepared by methods known in the art. Some such methods are described in Francesconi, I., et. al., *J. Med. Chem.*, 1999, 42, 2260; Kurzer, F., et. al., *Org. Synth.* 1963, 645; and Futman, A. D., U.S. Pat. No. 3,984,410. For example, ethyl benzenesulfonyl formimidate can be prepared by methods described in H. Stetter, D. H. *Theisen, Chem Ber.*, 1969, 102, 1641-42 and Ortiz, J. A., *Arzneim.-Forsch./DrugRes*, 1977, 47, 431-434.

Amino acids of formula 3 such as esters of alanine, cysteine, aspartic acid, glutamic acid, phenylalanine, histidine, and lysine are commercially available. Others can be prepared by methods well known in the art. Some such methods are described in PCT Applications Publication Nos. WO 00/55144, WO 01/19816, WO 02/20485, WO 03/029200, U.S. Provisional Application No. 60/422,337, U.S. Pat. Nos. 6,353,017B1, 6,492,662B1, 353,017B1 and 6,525,036B1, the disclosures of which are incorporated herein by reference in their entirety.

Hydrolysis of the ester group in 4, followed by reaction of the resulting acid with an amine of formula 5 where E is as defined in the Summary of the Invention provides a compound of Formula (Ia). The reaction can be effected with an appropriate coupling agent (e.g., benzotriazol-1-yloxy-trispyrrolidinophosphonium hexafluorophosphate (Py-BOP®), 1-(3-dimethylaminopropyl)-3-ethylcarbodiimide hydrochloride (EDCI), O-(7-azabenzotrizol-1-yl)-1,1,3,3,tetra-methyluronium-hexafluorophosphate (HATU), O-benzotriazol-1-yl-N,N,N',N'-tetramethyl-uronium hexafluorophosphate (HBTU), 1,3-dicyclohexylcarbodiimide (DCC), or the like) and optionally an appropriate catalyst (e.g., 1-hydroxybenzotriazole (HOBt), 1-hydroxy-7-azabenzotriazole (HOAt), or the like) and non-nucleophilic base (e.g., triethylamine, N-methylmorpholine, and the like, or any suitable combination thereof) at ambient temperature and requires 5 to 10 h to complete. Suitable reaction solvents include, but are not limited to, dimethylformamide, methylene chloride, and the like.

Alternatively, the free acid of compound 4 can be converted to an acid halide and then reacted with 5 to give a compound of Formula (Ia). The reacting is carried out in the presence of a base such as triethylamine, pyridine, and the like and in a suitable organic solvent such as tetrahydrofuran, dioxane, and the like.

Compounds of formula 5 where E is $—CR^5R^6X^1$ can be prepared by methods disclosed in U.S. patent application Ser. Nos. 60/373,176, 09/525,507, and 10/035,783 the disclosures of which are incorporated herein by reference in their entirety. Compounds of formula 5 where E is $—CR^{5a}R^{6a}CN$ are either commercially available or they can be prepared by methods well known in the art. For example, aminoacetonitrile is commercially available. Other nitriles can be prepared by methods disclosed in U.S. Patent Application No. 60/431,354; PCT Applications Publication Nos. WO 01/19816, WO 02/20485, WO 03/029200, U.S. Pat. Nos. 6,420,364B1, 6,353,017B1, 6,492,662B1, and 6,525,036B1, the disclosures of which are incorporated herein by reference in their entirety.

A compound of Formula (Ia) can be converted to other compounds of Formula (Ia). For example, a compound of Formula (Ia) where E is $—C(R^7)(R^8)R^{10}$ where $R^7$ is hydrogen and $R^8$ is hydroxy can be converted to other compounds of Formula (Ia) where E is $—COR^{10}$ by oxidation of the hydroxy group. The oxidation reaction is carried out with an oxidizing agent (e.g., Dess-Martin Periodinane®, TEMPO/bleach, or the like) in a suitable solvent (e.g., methanol, water, or the like, or any suitable combination thereof) at ambient temperature and requires 16 to 24 h to complete. Additionally, as stated previously, a compound of Formula (Ia) where $R^2$ is hydrogen can tautomerize to give a corresponding compound of Formula (Ib) where $R^{4a}$ is hydrogen.

Detailed descriptions for the synthesis of a compound of Formula (Ia) by the processes in Reaction Scheme 1 are set forth in the Example 1 below.

Alternatively, a Formula (Ia) where E is $—C(R^5)(6)X^1$ or $—C(R^{5a})(R^{6a})CN$ and $R^1$, $R^{1a}$, $R^2$, $R^3$, $R^4$, $R^5$, $R^{5a}$, $R^6$ and $R^{6a}$ are as defined in the Summary of the Invention can be prepared by proceeding as in the following Reaction Scheme 2 below.

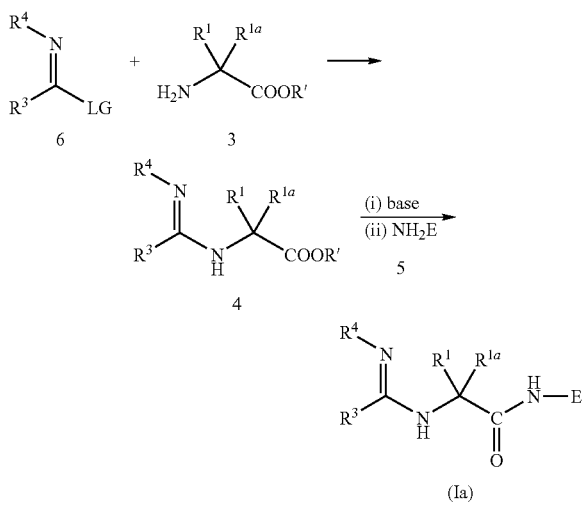

Reaction of a compound of formula 6 where LG is a leaving group such as halo with an amino compound of formula 3 provides a compound of formula 4 which is then converted to a compound of Formula (Ia) as described above. The reaction is carried out by methods well known in the art. Some such methods are described in Dunn. A. D., *Org. Prep. Proceed. Int.,* 1998, 30, 709; Lindstroem, S., et. al., *Heterocycles,* 1994, 38, 529; Katrizky, A. R., et. al., *Synthesis,* 1990, 561; Hontz, A. C., et. al., *Org. Synth.,* 1963, IV, 383; and Stephen, H., *J Chem., Soc.,* 1957, 490.

Alternatively, a compound of Formula (Ia) where E is —C(R$^5$)(R$^6$)X$^1$ or —C(R$^{5a}$)(R$^{6a}$)CN and R$^3$, R$^4$, R$^1$, R$^{1a}$, R$^5$, R$^{5a}$, R$^6$ and R$^{6a}$ are as defined in the Summary of the Invention can be prepared by proceeding as in the following Reaction Scheme 3 below.

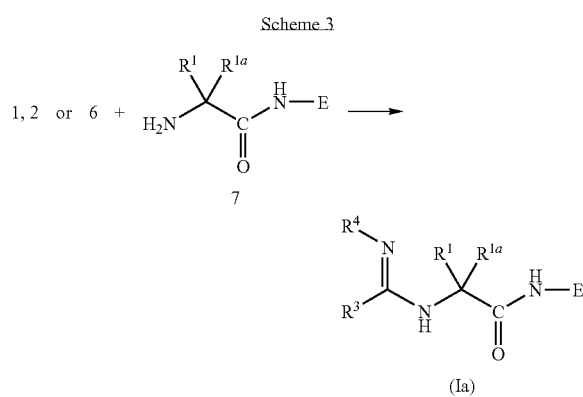

Reaction of a compound of formula 1, 2 or 6 with an amino compound of formula 7 provides a compound of Formula (Ia). The reaction is carried out under the reaction conditions described in Scheme 1 above. Compounds of formula 7 can be prepared by reacting an amino acid of formula 3 (R'=H) with an amino-protected compound of formula 5 under the coupling reaction conditions described above, followed by removal of the amino protecting group. Suitable amino protecting groups include, but are not limited to, tert-butoxycarbonyl, benzyloxycarbonyl, and the like. Alternatively, compound of formula 7 where E is —CR$^{5a}$R$^{6a}$CN can be prepared by reacting 5 with an amino amide of formula CR$^{5a}$R$^{6a}$(CONH$_2$)(NH$_2$) followed by dehydration of the resulting amide with a suitable dehydrating agent such as cyanuric chloride in dimethylformamide.

Other methods that can be utilized for preparing compounds of Formula (Ia) and (Ib) are described in PCT Application Publication Nos. WO 02/20485 and WO 03/029200, and U.S. Pat. No. 6,420,364, the disclosures of which are incorporated herein by reference in their entirety.

Additional Processes for Preparing Compounds of Formula (Ia) or (Ib):

A compound of Formula (Ia) or (Ib) can be prepared as a pharmaceutically acceptable acid addition salt by reacting the free base form of the compound with a pharmaceutically acceptable inorganic or organic acid. Alternatively, a pharmaceutically acceptable base addition salt of a compound of Formula (Ia) or (Ib) can be prepared by reacting the free acid form of the compound with a pharmaceutically acceptable inorganic or organic base. Inorganic and organic acids and bases suitable for the preparation of the pharmaceutically acceptable salts of compounds of Formula (Ia) or (Ib) are set forth in the definitions section of this Application. Alternatively, the salt forms of the compounds of Formula (Ia) or (Ib) can be prepared using salts of the starting materials or intermediates.

The free acid or free base forms of the compounds of Formula (Ia) or (Ib) can be prepared from the corresponding base addition salt or acid addition salt form. For example, a compound of Formula (Ia) or (Ib) in an acid addition salt form can be converted to the corresponding free base by treating with a suitable base (e.g., ammonium hydroxide solution, sodium hydroxide, and the like). A compound of Formula (Ia) or (Ib) in a base addition salt form can be converted to the corresponding free acid by treating with a suitable acid (e.g., hydrochloric acid, etc).

The N-oxides of compounds of Formula (Ia) or (Ib) can be prepared by methods known to those of ordinary skill in the art. For example, N-oxides can be prepared by treating an unoxidized form of the compound of Formula (Ia) or (Ib) with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds of Formula (Ia) or (Ib) can be prepared from the N-oxide of an appropriate starting material.

Compounds of Formula (Ia) or (Ib) in unoxidized form can be prepared from N-oxides of compounds of Formula (Ia) or (Ib) by treating with a reducing agent (e.g., sulfur, sulfur dioxide, triphenyl phosphine, lithium borohydride, sodium borohydride, phosphorus trichloride, tribromide, or the like) in an suitable inert organic solvent (e.g., acetonitrile, ethanol, aqueous dioxane, or the like) at 0 to 80° C.

Prodrug derivatives of the compounds of Formula (Ia) or (Ib) can be prepared by methods known to those of ordinary skill in the art (e.g., for further details see Saulnier et al. (1994), *Bioorganic and Medicinal Chemistry Letters*, Vol. 4, p. 1985). For example, appropriate prodrugs can be prepared by reacting a non-derivatized compound of Formula (Ia) or (Ib) with a suitable carbamylating agent (e.g., 1,1-acyloxy-alkylcarbonochloridate, para-nitrophenyl carbonate, or the like).

Protected derivatives of the compounds of Formula (Ia) or (Ib) can be made by means known to those of ordinary skill in the art. A detailed description of the techniques applicable to the creation of protecting groups and their removal can be found in T. W. Greene, *Protecting Groups in Organic Synthesis,* 3$^{rd}$ edition, John Wiley & Sons, Inc. 1999.

Compounds of the present invention may be conveniently prepared, or formed during the process of the invention, as solvates (e.g. hydrates). Hydrates of compounds of the present invention may be conveniently prepared by recrystallisation from an aqueous/organic solvent mixture, using organic solvents such as dioxin, tetrahydrofuran or methanol.

Compounds of Formula (Ia) or (Ib) can be prepared as their individual stereoisomers by reacting a racemic mixture of the compound with an optically active resolving agent to form a pair of diastereoisomeric compounds, separating the diastereomers and recovering the optically pure enantiomer. While resolution of enantiomers can be carried out using covalent diasteromeric derivatives of compounds of Formula (Ia) or (Ib), dissociable complexes are preferred (e.g., crystalline diastereoisomeric salts). Diastereomers have distinct physical properties (e.g., melting points, boiling points, solubilities, reactivity, etc.) and can be readily separated by taking advantage of these dissimilarities. The diastereomers can be separated by chromatography or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques Andre Collet, Samuel H. Wilen, Enantiomers, Racemates and Resolutions, John Wiley & Sons, Inc. (1981).

Pharmacology and Utility

The compounds of the invention are selective inhibitors of cysteine proteases, in particular, cathepsin S, K, B, and/or F, and accordingly are useful for treating diseases in which cysteine protease activity contributes to the pathology and/or symptomatology of the disease. For example, the compounds of the invention are useful in treating autoimmune disorders, including, but not limited to, juvenile onset diabetes, psoriasis, multiple sclerosis, pemphigus vulgaris, Graves' disease, myasthenia gravis, systemic lupus erythemotasus, rheumatoid arthritis and Hashimoto's thyroiditis, allergic disorders, including, but not limited to, asthma, allogeneic immune responses, including, but not limited to, organ transplants or tissue grafts and endometriosis.

Cathepsin S is also implicated in disorders involving excessive elastolysis, such as chronic obstructive pulmonary disease (e.g., emphysema), bronchiolitis, excessive airway elastolysis in asthma and bronchitis, pneumonitis and cardiovascular disease such as plaque rupture and atheroma. Cathepsin S is implicated in fibril formation and, therefore, inhibitors of cathepsins S are of use in treatment of systemic amyloidosis.

The cysteine protease inhibitory activities of the compounds of the invention can be determined by methods known to those of ordinary skill in the art. Suitable in vitro assays for measuring protease activity and the inhibition thereof by test compounds are known. Typically, the assay measures protease-induced hydrolysis of a peptide-based substrate. Details of assays for measuring protease inhibitory activity are set forth in Biological Examples 1-5, infra.

Administration and Pharmaceutical Compositions

In general, compounds of Formula (Ia) or (Ib) will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. For example, therapeutically effective amounts of a compound of Formula (Ia) or (Ib) may range from about 10 micrograms per kilogram body weight (μg/kg) per day to about 20 milligram per kilogram body weight (mg/kg) per day, typically from about 100 μg/kg/day to about 10 mg/kg/day. Therefore, a therapeutically effective amount for a 80 kg human patient may range from about 1 mg/day to about 1.6 g/day, typically from about 1 mg/day to about 100 mg/day. In general, one of ordinary skill in the art, acting in reliance upon personal knowledge and the disclosure of this Application, will be able to ascertain a therapeutically effective amount of a compound of Formula (Ia) or (Ib) for treating a given disease.

The compounds of Formula (Ia) or (Ib) can be administered as pharmaceutical compositions by one of the following routes: oral, systemic (e.g., transdermal, intranasal or by suppository) or parenteral (e.g., intramuscular, intravenous or subcutaneous). Compositions can take the form of tablets, pills, capsules, semisolids, powders, sustained release formulations, solutions, suspensions, elixirs, aerosols, or any other appropriate composition and are comprised of, in general, a compound of Formula (Ia) or (Ib) in combination with at least one pharmaceutically acceptable excipient. Acceptable excipients are non-toxic, aid administration, and do not adversely affect the therapeutic benefit of the active ingredient. Such excipient may be any solid, liquid, semisolid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, and the like. Liquid and semisolid excipients may be selected from water, ethanol, glycerol, propylene glycol and various oils, including those of petroleum, animal, vegetable or synthetic origin (e.g., peanut oil, soybean oil, mineral oil, sesame oil, and the like). Preferred liquid carriers, particularly for injectable solutions, include water, saline, aqueous dextrose and glycols.

The amount of a compound of Formula (Ia) or (Ib) in the composition may vary widely depending upon the type of formulation, size of a unit dosage, kind of excipients and other factors known to those of skill in the art of pharmaceutical sciences. In general, a composition of a compound of Formula (Ia) or (Ib) for treating a given disease will comprise from 0.01% w to 10% w, preferably 0.3% w to 1% w, of active ingredient with the remainder being the excipient or excipients. Preferably the pharmaceutical composition is administered in a single unit dosage form for continuous treatment or in a single unit dosage form ad libitum when relief of symptoms is specifically required. Representative pharmaceutical formulations containing a compound of Formula (Ia) or (Ib) are described in Example 1 below.

EXAMPLES

The present invention is further exemplified, but not limited by, the following examples that illustrate the preparation of compounds of Formula (Ia) or (Ib) (examples) and intermediates references) according to the invention.

General Procedures

Example A

Synthesis of 2(RS)-benzyloxycarbonylamino-4(RS)-(2-methoxyphenyl)pentanoic acid

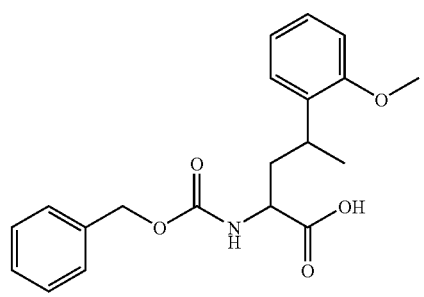

To d,l-2-methoxy-α-methylbenzyl alcohol (0.5 g, 3.29 mmol) was added 48% aq. HBr (2 mL) and the reaction mixture was stirred rapidly for 1.5 h. The reaction mixture was diluted with hexane (30 mL), washed with water, dried with MgSO$_4$, filtered, and evaporated under vacuum. The crude d,l-2-methoxy-α-methylbenzyl bromide was added to a solution of tributyltin hydride (0.67 mL, 2.49 mmol), Z-dehydroalanine methyl ester (0.25 g, 1.06 mmol), and 2,2'-azobisisobutyronitrile (15 mg, 0.09 mmol) in benzene (5 mL). The reaction mixture was heated at 80° C. under a nitrogen atmosphere for 5 h. Benzene was removed under vacuum and the residue was dissolved in methanol (20 mL). 2N KOH (5 mL) was added and the mixture was rapidly stirred at room temperature over night. Methanol was removed under vacuum and the residue was diluted with water (20 mL). The aqueous solution was washed with ether to remove the tin by-products. The aqueous layer was acidified with 6 N HCl (aq.) and the product was extracted with ethyl acetate. The combined organic layers were washed with brine, dried with MgSO$_4$, filtered, and evaporated under vacuum to give 2-benzyloxycarbonylamino-4-(2-methoxyphenyl)pentanoic acid (190 mg, 0.53 mmol) as a mixture of diastereomers in sufficiently pure form to be used without further purification. MS: (M$^+$+H) 358, (M$^+$−H) 356.

Following the procedure described above, and utilizing appropriate starting materials the following amino acids were prepared:

2(RS)-benzyloxycarbonylamino-4(RS)-(2-methoxyphenyl)hexanoic acid;

2(RS)-benzyloxy-carbonylamino-4(RS)-(4-fluorophenyl)pentanoic acid;

2(RS)-benzyloxycarbonylamino-4(RS)-(4-chlorophenyl)pentanoic acid;

2(RS)-benzyloxycarbonylamino-4(RS)-(4-methoxyphenyl)pentanoic acid;

2(RS)-benzyloxycarbonylamino-4(RS)-(2-trifluoromethylphenyl)pentanoic acid;

2(RS)-benzyloxycarbonylamino-4(RS)-(3-trifluoromethylphenyl)pentanoic acid;

2(RS)-benzyloxycarbonylamino-4(RS)-(napth-1-yl)pentanoic acid;

2(RS)-benzyloxycarbonylamino-4(RS)-(2,6-dimethylphenyl)pentanoic acid;

2(RS)-benzyloxycarbonylamino-4(RS)-(2,4-difluorophenyl)pentanoic acid;

2(RS)-benzyloxycarbonylamino-4(RS)-(2,4-dimethylphenyl)pentanoic acid;

2(RS)-benzyloxycarbonylamino-4(RS)-(2,5-dimethylphenyl)pentanoic acid; and

2(RS)-benzyloxycarbonylamino-4(RS)-(2,4-dichlorophenyl)pentanoic acid,

The benzyloxycarbonyl group can be removed as described in Example C below to give the corresponding free amino acid.

Example B

Synthesis of 2(S)-2,6-difluorophenylalanine

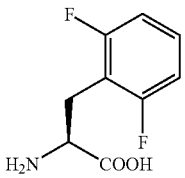

Step 1

N-(Benzyloxycarbonyl)-α-phosphonoglycine trimethyl ester (Aldrich No. 37,635-3; 6.7 g, 20 mmol) and 1,8-diazabicyclo[5,4,0]undec-7-ene (Aldrich No. 13, 900-9; 3.3 mL, 22 mmol) were dissolved in methylene chloride (11 mL) and stirred at room temperature for 15 min., and then cooled to <−30° C. A solution of 2,6-difluorobenzaldehyde (1.9 mL, 20 mmol) in methylene chloride (25 mL) was added to the reaction mixture dropwise over 20 min. The reaction mixture was stirred for another 20 min., and then allowed to warm up to room temperature for 30 min. The reaction mixture was then poured into ethyl ether (300 mL) and washed with 1 N HCl, brine and dried over MgSO$_4$. Rotary evaporation gave 2-benzyloxycarbonylamino-3-(2,6-difluorophenyl)acrylic acid methyl ester. This crude product was purified by chromatography on a Medium Pressure Liquid Column (MPLC) eluting with 20% ethyl acetate/80% hexane to give pure product (5 g, 72% yield, liquid).

Step 2

A mixture of 2-benzyloxycarbonylamino-3-(2,6-difluorophenyl)acrylic acid methyl ester (14.4 mmol), and catalyst, (+)-1,2-bis-[(2S,5S)2,5-diethylphopholano]benzene (cyclooctadiene)rhodium (I) trifluoromethanesulfonate (Strem. Chemical No. 45-0151; 104 mg, 0.14 mmol) was dissolved in ethanol (150 mL). Hydrogenation was performed at 50 psi H$_2$ at room temperature over 2 days. The solvent was then removed by rotary evaporation to give 2(S)-benzyloxycarbonylamino-3-(2,6-difluorophenyl)propionic acid methyl ester.

Step 3

2(S)-Benzyloxycarbonylamino-3-(2,6-difluorophenyl)propionic acid methyl ester (5 g, 14.4 mmol) was dissolved in methanol (60 mL) and cooled on ice. 1 N NaOH (22 mL, 22 mmol) was added dropwise over 15 min. The reaction mixture was removed from cooling and continue stirring at room temperature for 4 h. The solvent was then removed by rotary evaporation. The residue was treated with water (100 mL) and then with 1 N HCl to adjust the pH to 4. The product was extracted with ethyl acetate (300 mL, 200 mL). Evaporation of the solvent and crystallization of the residue from methylene chloride/hexane gave 2(S)-benzyloxycarbonylamino-3-(2,6-difluoro-phenyl)propionic acid (4.6 g, 13.7 mmol, 94% yield).

Step 4

2(S)-Benzyloxycarbonylamino-3-(2,6-difluorophenyl)-propionic acid was hydrogenated at 50 psi in ethanol (25 mL) in the presence of 5% palladium on activated carbon (600 mg) for 24 h. The catalyst was removed by filtration through celite and the solvent evaporated to give a residue which was crystalized from ethyl ether to give 2(S)-2,6-difluorophenylalanine (2.2 g, 11 mmol, 80% yield). $^1$H NMR (DMSO-d$_6$): δ 7.28 (m, 1H), 7.0 (t, J=7.6 Hz, 2H), 2.77 (m, 2H). MS: 202.2 (M+1), 199.7(M−1).

Example C

Synthesis of 2(RS)-amino-4(RS)-6,6-trimethylheptanoic acid

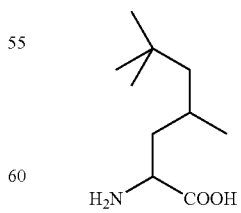

Step 1

To a mixture of the 3,5,5-trimethylhexanal (17.4 mL, 0.10 mol), ammonium chloride (53.5 g, 0.205 mol) and diethyl ether (113 mL) was added sodium cyanide (7.35 g, 0.15 mol)

in water (38 mL). The reaction mixture was allowed to stir vigorously for 16 h. The layers were separated. The aqueous layer was extracted with diethyl ether. The combined organic layer was then extracted with 1 N HCl. Saturated sodium bicarbonate was then added until 1-cyano-3,5,5-trimethyl-hexylamine was completely precipitated. Vacuum filtration and washing with 5 mL ice cold water followed by lyophilization gave 1-cyano-3,5,5-trimethylhexylamine (5.805 g, 0.034 mol, 34.5%) as a white solid.

Step 2

1-Cyano-3,5,5-trimethylhexylamine (1.02 g, 5.0 mmol) was treated with 6N HCl (10 mL) and heated at reflux for 30 h. The reaction mixture was allowed to cool to room temperature. Water (50 mL) was added, and the mixture was washed with diethyl ether. The aqueous layer was basified to pH 8.5 with 2 M KOH. A white precipitate formed which was collected by vacuum filtration to give 2(RS)-amino-4(RS),6,6-trimethyl-heptanoic acid (364 mg).

Example D

Synthesis of 2(RS)-amino-4-methyl-4-phenylpentanoic acid

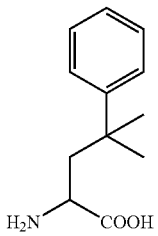

Step 1

4-Methyl-4-phenyl-1-pentene was prepared by reacting 2-phenyl-2-propanol with 3-(trimethylsilyl)propene by the method of Cella, *J. Org. Chem.*, 1982, 47, 2125-2130.

Step 2

4-Methyl-4-phenyl-1-pentene was ozonolyzed at −78° C. in dichloromethane followed by dimethyl sulfide quenching to give crude product which was purified by silica gel chromatography to give 3-methyl-3-phenylbutanal which was then converted to the title compound by proceeding as described in Example D above.

Reference E

Synthesis of 2(R)-tert-butoxycarbonylamino-3-cyclopropylmethanesulfonylpropionic acid

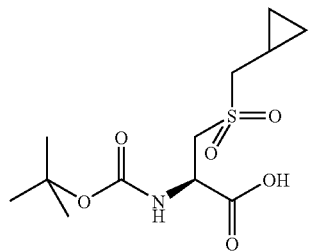

Step 1

Sodium hydroxide (2.16 g, 54 mmol) was dissolved in water (27 mL) and the solution added to a suspension of (R)-2-tert-butoxycarbonylamino-3-mercaptopropionic acid (8.2 g, 37 mmol) in methanol (54 mL). After a clear solution had formed bromomethyl-cyclopropane (5 g, 37 mmol) was added and the resulting reaction mixture stirred for three days. Methanol was removed under reduced pressure. The residue was treated with 1M hydrochloric acid (200 mL) and then extracted with dichloromethane. The combined organic phases were washed with brine and dried with magnesium sulfate. The solvent was evaporated under reduced pressure to give 2-tert-butoxycarbonylamino-3-cyclopropylmethylsulfanyl-propionic acid (7.94 g).

Step 2

Sodium hydroxide (2.32 g, 58 mmol) was dissolved in water (27 mL). 2-tert-Butoxycarbonylamino-3-cyclopropylmethylsulfanyl-propionic acid (7.94 g, 29 mmol) was added. A solution of Oxone™ in water (100 mL) was added slowly. The pH was adjusted to 3 by addition of sodium bicarbonate and the reaction mixture stirred for 30 minutes and extracted with ethyl acetate. The combined organic phases were washed with brine and dried with magnesium sulfate. The solvent was removed to yield 2(R)-tert-butoxycarbonylamino-3-cyclopropylmethanesulfonyl-propionic acid (4.64 g, 15 mmol, 31%).

Example F

Synthesis of 2(RS)-benzyloxycarbonylamino-4-ethylhexanoic acid

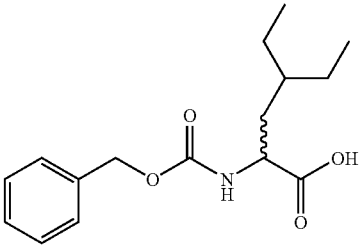

Step 1

A mixture of 2-benzyloxycarbonylaminomalonic acid diethyl ester (Bladon, C. M. *J. Chem. Soc. Perkin Trans.* 1990, 1, 1151-1158) (1.237 g), iodo-2-ethylbutane (1.272 g) and lithium hydroxide (0.287 g) in N-methylpyrrolidone (8 mL) was stirred for 2 days at room temperature and then diluted with ice water. The aqueous solution was extracted with ether and the product purified by chromatography on silica gel to give 2-benzyloxycarbonylamino-2-(2-ethylbutyl)malonic acid diethyl ester (0.520 g).

Step 2

A solution of 2-benzyloxycarbonylamino-2-(2-ethylbutyl)malonic acid diethyl ester (0.520 g) in ethanol (5 mL) was treated with sodium hydroxide (2.91 mL, 1 N) and then stirred at room temperature for 8 h. The reaction mixture was diluted with water and acidified with HCl and the product was then extracted with ethyl acetate to give 2-benzyloxycarbonylamino-2-(2-ethylbutyl)malonic acid monoethyl ester (0.461 g).

Step 3

2-Benzyloxycarbonylamino-2-(2-ethylbutyl)malonic acid monoethyl ester was heated at 75° C. in ethanol (5 mL) with sodium hydroxide (5 mL, 1 N) for 3 h and 2-benzyloxycarbonylamino-2-(2-ethylbutyl)malonic acid was isolated by extraction of the acidified reaction mixture. 2-Benzyloxycarbonylamino-2-(2-ethylbutyl)malonic acid was heated at 103° C. for 1 h and the resulting residue was purified by column chromatography on silica gel to give 2(RS)-benzyloxycarbonylamino-4-ethylhexanoic acid (0.220 g).

Example G

Synthesis of 2(S)-benzyloxycarbonylamino-3-pyrazol-1-ylpropionic acid

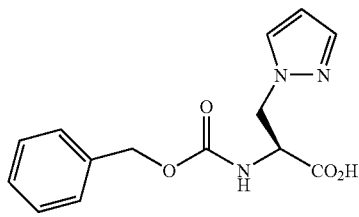

The title compound was prepared by treating S-benzyloxycarbonylserine-β-lactone with pyrazole in acetonitrile at 60° C. for 16 h (see *J. Am. Chem. Soc.*, 1985, 107, 7105-7109).

Following the procedure described above, but substituting pyrazole with 1,2,4-triazole and 1,2,3-triazole provided 2(S)-benzyloxycarbonylamino-3-[1,2,4]-triazol-1-ylpropionic acid and 2(8)-benzyloxycarbonylamino-3-[1,2,3]-triazol-1-ylpropionic acid respectively.

Reference H

Synthesis of 2(S)-benzyloxycarbonylamino-3-(1-methylcyclopentyl)-propionic acid

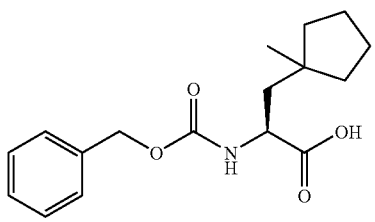

Step 1

1-Methylcyclopentanol (20 g, 0.2 mol) was added to hydrobromic acid (40 mL) at room temperature. After stirring for 1 h, the solution was extracted with hexane and the hexane was washed with brine and dried with magnesium sulfate. After concentration of the organic layer, 20.5 g of 1-methylcyclopentyl bromide was obtained.

Step 2

Tributyltin hydride (37.8 g, 130 mmol) was added at reflux to a 500 ml of flask charged with benzene (200 mL) was added Z-dehydro-Ala-OH (15 g, 64 mmol), 1-methylcyclopentanylbromide (20.5 g) and AIBN (1.9 g). After 2 h, the solvent was removed and the residue was purified by column chromatograph to yield 7.9 g of 2-benzyloxycarbonylamino-3-(1-methylcyclopentyl)-propionic acid methyl ester.

Step 3

2-Benzyloxycarbonylamino-3-(1-methylcyclopentyl)-propionic acid methyl ester (7.6 g, 23.8 mmol) was dissolved in a mixture of acetonitrile (82 mL) and 0.2 M aqueous NaHCO$_3$ (158 mL) and Alcalase 2.4 L (1.1 mL) was added and the reaction mixture was stirred vigorously for 8 h. The reaction mixture was then evaporated at 30° C. to remove acetonitrile, and the aqueous residue was washed with ether. The ethereal layer was concentrated to yield 1.9 g of 2(R)-benzyloxycarbonylamino-3-(1-methylcyclopentyl)-propionic acid methyl ester. The aqueous phase was filtered with Celite, the pH was adjusted to 3 with 6 N HCl, and the solution was extracted with ethylacetate. The ethyl acetate layer was dried and evaporated to yield 1.4 g of 2(S)-benzyloxycarbonylamino-3-(1-methylcyclopentyl)propionic acid.

Example I

Synthesis of 2(S)-(tert-butoxycarbonyl)amino-1-(oxazolo[4,5-b]pyridin-2-yl)butan-1-ol

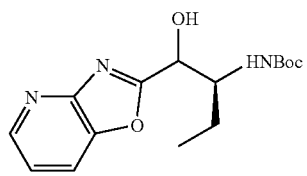

Step 1

A mixture of 2-amino-3-hydroxypyridine (11 g, 100 mmol), triethylorthoformate (80 mL) and p-toluenesulfonic acid (61 mg) was heated at 140° C. for 8 h. Excess triethylorthoformate was removed under vacuum and oxazolo[4,5-b]pyridine was crystalized from ethyl acetate (9 g).

Step 2

In a round bottom flask equipped with stir bar was placed oxazolo[4,5-b]pyridine (600 mg, 5 mmol) in THF (30 mL) and the reaction mixture was cooled to 0° C. under N$_2$ atomosphere. Isopropylmagnesium chloride (2 M in THF, 2.5 mL, 5 mmol) was added. After stirring for 1 h at 0° C., (S)-2-(tert-butoxycarbonyl)aminobutyraldehyde (573 mg, 3 mmol) in THF (20 mL) was added. The ice bath was removed and the reaction mixture was allowed to warm to room temperature. After 2 h, the reaction mixture was quenched with saturated ammonium chloride solution and concentrated to dryness. The residue was extracted with EtOAc, then washed with brine, dried with anhyd. MgSO$_4$, filtered and concentrated. The crude product was purified by chromatograph to yield 383 mg of the desired compound.

H$^1$ NMR (DMSO-d$_6$): δ 8.42 (m, 114), 8.18 (m, 1H), 7.3 (m, 1H), 6.8-6.6 (dd, d, 1H, OH, diastereomer), 6.3-6.02 (d, d, 1H, NH, diastereomer), 4.82-4.5 (m,m, 1H, diastereomer), 1.8-1.3 (m, 2H), 1.2-1.05 (s,s, 9H, diastereomer), 0.89 (m, 3H). MS: 306.2 (M−1), 308.6 (M+1).

Example J

Synthesis of 2(S)-tert-butoxycarbonylamino-3-thiazol-2-ylpropionic acid

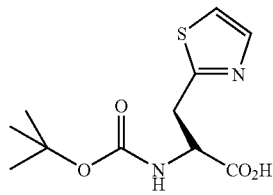

To 2-tert-butoxycarbonylamino-3-thiazol-2-yl-propionic acid methyl ester (500 mg, 1.75 mmol) in a mixture of acetonitrile (6 mL) and 0.2 M aqueous NaHCO₃ (12 mL) was added Alcalase (2.4 L, 0.08 mL), and the solution was stirred vigorously at room temperature for about 2.5 h. The reaction mixture was then evaporated at 30° C. to remove acetonitrile, and the aqueous residue was washed with ether. The aqueous phase was acidified with 6 N HCl to pH 3 and the solution was extracted with ethyl acetate. The combined organic layers were then dried and evaporated to yield 2(S)-tert-butoxycarbonylamino-3-thiazol-2-yl-propionic acid (204 mg).

Reference K

Synthesis of 4(S)-amino-2,2-difluoro-3-hydroxyhexanoic acid dimethylamide

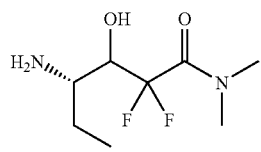

Activated zinc dust (2.16 g, 33 mmol) was suspended in dry THF (2 mL). A mixture of ethyl bromodifluoro acetate (6.5 g, 32 mmol) and (1S)-(1-formylpropyl) carbamic acid tert-butyl ester (2 g, 10.7 mmol), in THF (10 mL), was added over 20 min while the reaction mixture was sonicated. After complete addition, sonication was continued for a further 30 min. The reaction mixture was then diluted with ethyl acetate (200 mL) and washed with 1N aqueous KHSO₄, brine, dried with magnesium sulfate and evaporated. The crude product was dissolved in ethanol (15 mL) and a solution of dimethylamine (40% in water; 2 mL) was added. After stirring for 16 h at ambient temperature, the solvents were evaporated and the product was purified by flash chromatography on silica gel (hexane/ethyl acetate ratio of 3:1) to yield 200 mg 4(S)-Boc-amino-2,2-difluoro-3-hydroxy-hexanoic acid dimethylamide of colorless oil which was dissolved in a mixture of TFA/dichloromethane (1:1; 6 mL), stirred for 1 h and evaporated to dryness. The product, 4(S)-amino-2,2-difluoro-3-hydroxy-hexanoic acid dimethylamide, was obtained as the TFA salt and used without further purification.

Reference L

Synthesis of 3(S)-amino-2-hydroxypentanoic acid benzylamide

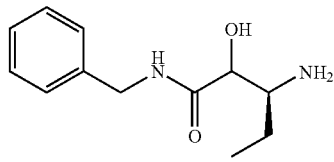

Step 1

(1S)-(2-Cyano-1-ethyl-2-hydroxyethyl)carbamic acid tert-butyl ester (10 g, 46.7 mmol) was dissolved in 1,4-dioxane (100 mL). Anisole (5 mL) was added and then concentrated HCl (100 mL). The reaction mixture was heated under reflux for 24 h. The reaction mixture was evaporated to dryness under vacuum and re-dissolved in 100 mL water. The solution was washed with ether and then neutralized with saturated aqueous NaHCO₃. Di-tert-butyl dicarbonate (10 g, 46 mmol) was added with 1,4-dioxane (200 mL), and the reaction mixture was stirred at ambient temperature for 24 h. The dioxane was removed under vacuum and the remaining aqueous solution was washed with ether. The solution was acidified with 1N HCl and extracted with ethyl acetate. The combined organic layers were washed with brine, dried with magnesium sulfate and evaporated to yield 3-tert-butoxycarbonylamino-2-hydroxypentanoic acid (4.5 g) as yellowish oil.

Step 2

3-tert-Butoxycarbonylamino-2-hydroxypentanoic acid (300 mg, 1.29 mmol) was combined with EDC (400 mg, 2.1 mmol) and HOBt (400 mg, 2.6 mmol). A solution of benzylamine (0.22 mL) and 4-methylmorpholine (0.5 mL) in dichloromethane (4 mL) was added in one portion. The reaction mixture was stirred at ambient temperature for 2 h. After dilution with ethyl acetate (150 mL), the solution was washed with 1 N aqueous HCl, water, saturated aqueous NaHCO₃ solution and brine. The resultant mixture was dried with magnesium sulfate and evaporated under vacuum to yield 3(S)-amino-2-hydroxy-pentanoic acid benzylamide (380 mg) as a white solid.

Step 3

3(S)-Amino-2-hydroxypentanoic acid benzylamide was dissolved in a mixture of TFA/dichloromethane (1:1; 6 mL), stirred for 1 h and evaporated to dryness to give 3(S)-amino-2-hydroxypentanoic acid benzylamide was obtained as the TFA salt and used without further purification.

Reference M

Synthesis of 2(S)-amino-1-(3-phenyl-[1.2.4]oxadiazol-5-yl)butan-1-ol

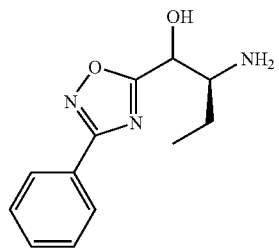

3-tert-Butoxycarbonylamino-2-hydroxy-pentanoic acid (500 mg, 2.14 mmol) was combined with EDC (600 mg, 3.14 mmol), HOBt (600 mg, 3.92 mmol), and N-hydroxy-benzamidine (292 mg, 2.14 mmol). Dichloromethane (10 mL) was added and then 4-methylmorpholine (1 mL). The reaction mixture was stirred at ambient temperature for 16 h. After dilution with ethyl acetate (200 mL), the solution was washed with water (30 mL), saturated aqueous NaHCO$_3$ solution and brine, dried with MgSO$_4$ and evaporated under vacuum. The crude product was dissolved in pyridine (10 mL) and heated at 80° C. for 15 h. The pyridine was evaporated under vacuum and the residue was purified by flash chromatography on silica gel (eluent:ethyl acetate) to yield 2(S)-tert-butoxycarbonylamino-1-(3-phenyl-[1.2.4]oxadiazol-5-yl)butan-1-ol (290 mg, 0.83 mmol). 2(S)-tert-butoxycarbonylamino-1-(3-phenyl-[1.2.4]oxadiazol-5-yl)butan-1-ol (145 mg, 0.41 mmol) was dissolved in CH$_2$Cl$_2$ (4 mL) and TFA (4 mL) was added. After stirring for 1 h, the reaction mixture was evaporated to dryness to yield 2(S)-amino-1-(3-phenyl-[1.2.4]oxadiazol-5-yl)-butan-1-ol.

Reference N

Synthesis of 2(S)-amino-1-(2-phenyl-[1,3]dithian-2-yl)hexan-1-ol

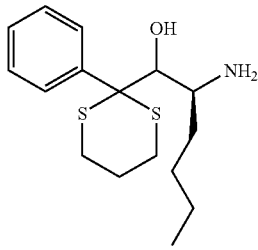

Step 1

2-Phenyl-1,3-dithiane (Aldrich) (3.79 g; 19.3 mmol) was mixed with dry distilled THF (20 mL) under a nitrogen atmosphere. The solution was cooled to −60° C. and n-butyl lithium (1.6M in pentane, 1.56 mmol, 9.74 mL) was added slowly by syringe. The reaction mixture was warmed to −20° C. and held at that temperature for 30 min., and then held at −10° C. for 15 min. The yellow solution was cooled to −78° C. and (1-formylpentyl)carbamic acid tert-butyl ester (1.6 g, 1.4 mmol, in 5 mL THF) was added rapidly (over 20 seconds) and 60 seconds later a mixture of 2 mL acetic acid and 5 mL THF was added rapidly. After warming to 23° C. the solution was concentrated at reduced pressure. Excess 2-phenyl-1,3-dithiane was removed by its crystallization away from the desired product using a minimum of ethyl acetate in hexane. The mother liquors were concentrated and chromatographed using a hexane-ethyl acetate gradient to afford {1-[hydroxy-(2-phenyl-[1,3]dithian-2-yl)methyl]pentyl}carbamic acid tert-butyl ester. (1.7 g, 56% yield).

Step 2

To {1-[hydroxy-(2-phenyl-[1,3]dithian-2-yl)methyl]pentyl}carbamic acid tert-butyl ester (608 mg, 1.47 mmol) in dioxane (2.7 mL) at 10° C. was added hydrochloric acid (2.7 mL, 4 M in dioxane). The solution was warmed to 23° C. After 3 h, the solution was diluted with toluene (5 ml) and concentrated under reduced pressure. The gummy solid was washed with diethyl ether resulting in the hydrochloride salt of 2(8)-amino-1-(2-phenyl-[1,3]dithian-2-yl)hexan-1-ol, (414 mg, 82%) as a free flowing solid after removal of excess ether under reduced pressure.

Reference O

Synthesis of 3-amino-4-hydroxypyrrolidine-1-carboxylic acid tert-butyl ester

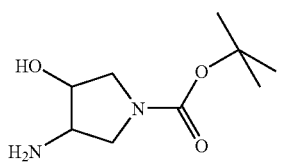

6-Oxa-3-aza-bicyclo[3.1.0]hexane-3-carboxylic acid tert-butyl ester (12.1 g, 65.3 mmol) was dissolved in a 8:1 methanol/water mixture (108 mL). Ammonium chloride (15 g) and sodium azide (21.4 g, 329 mmol) was added and the reaction mixturewas heated at 60° C. overnight. After dilution with ether (500 mL), the reaction mixturewas washed with saturated aqueous NaHCO$_3$ (200 mL) and brine (200 mL), dried with MgSO$_4$ and evaporated under vacuum. The crude product was dissolved in methanol (200 mL). 10% Palladium on activated carbon (1.5 g) was added and the reaction mixturewas stirred at ambient temperature under a hydrogen atmosphere until TLC analysis showed the disappearance of the starting material. The reaction mixture was filtered through a pad of Celite and evaporated to dryness under vacuum. The product was purified by flash chromatography on silica gel using 5% methanol in ethyl acetate to 20% methanol, 3% triethylamine in ethyl acetate to give 4.3 g of 3-amino-4-hydroxy-pyrrolidine-1-carboxylic acid tert-butyl ester as yellowish solid.

Reference P

Synthesis of 2-amino-2-methyl-1-oxazolo[4,5-b]pyridin-2-yl-propan-1-ol

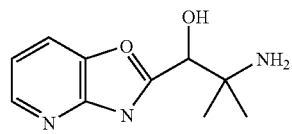

Step 1

2-Amino-2-methyl-1-propanol (17.8 g, 200 mmol) was dissolved in a mixture of water and dioxane (100 mL) and cooled to 0° C. NaOH (8 g, 200 mmol) and di-t-butyl-dicarbonate (52.4 g, 240 mmol) were added and the reaction was allowed to warm to room temperature with stirring for 2 h. After removing the dioxane, the residue was extracted with EtOAc, washed with brine, dried with anhydrous MgSO$_4$, filtered and concentrated to yield 35 g of 2-Boc-amino-2-methyl-1-propanol.

Step 2

A solution of oxalyl chloride (15.24 g, 120 mmol) in 200 mL of MeCl$_2$ was stirred and cooled to −60° C. followed by the drop wise addition of dimethylsulfoxide (19.7 g, 252 mmol) in 60 ml of MeCl$_2$. After 10 min, a solution of 2-Boc-amino-2-methyl-1-propanol (18.9 g, 100 mmol) in MeCl$_2$ (60 ml) was added drop wise at −70° C. The reaction mixture was allowed to warm to −40° C. for 10 min followed by cooling to −70° C. before the addition of a solution of triethylamine (28.28 g, 280 mmol) in MeCl$_2$ (60 mL). The reaction mixture was allowed to warm to room temperature over a two-hour period and 40 mL of saturated sodium dihydrogen phosphate was added. The organic layer was washed with brine and dried over MgSO$_4$. The solvent was removed to yield 17.3 g of 2-Boc-amino-2-methylpropionaldehyde.

Step 3

A mixture of 2-amino-3-hydroxypyridine (11 g, 100 mmol), triethylorthoformate (80 mL) and p-toluenesulfonic acid (61 mg) was heated at 140° C. for 8 h. Excess triethylorthoformate was removed under vacuum. The product was crystallized from ethyl acetate to yield 9 g of 1-oxazolo[4,5-b]pyridine.

Step 4

To a stirred solution of the 1-oxazolo[4,5-b]pyridine (2.4 g, 20 mmol) in THF (100 mL) was added n-BuLi (1.6 M solution in 12.5 mL of hexane) drop wise under N$_2$ at −78° C. After 1 h, MgBr.Et$_2$O (5.16 g, 20 mmol) was added and the reaction mixture was allowed to warm to −45° C. for 1 h before being treated with 2-Boc-amino-2-methylpropionaldehyde (2.24 g, 12 mmol) in THF (20 mL). The reaction mixture was stirred for 1 h, quenched with saturated NH$_4$Cl, and extracted with ethyl acetate. The organic layer was washed with brine, dried with MgSO$_4$ and concentrated. The residue was purified by silica gel column chromatography to yield 2-Boc-amino-2-methyl-1-oxazolo[4,5-b]pyridin-2-yl-1-propanol (1.18 g).

Step 5

2-Boc-amino-2-methyl-1-oxazolo[4,5-b]pyridin-2-yl-1-propanol (156 mg, 0.508 mmol) and MeCl$_2$ (5 mL) were mixed and TFA (0.5 mL) was added at room temperature. After stirring for 1 h, the solvent and excess TFA were removed under vacuum to produce 2-amino-2-methyl-1-oxazolo[4,5-b]pyridin-2-yl-propan-1-ol. TFA salt (165 mg).

Reference Q

Synthesis of 2(S)-amino-1-(5-methoxymethyl-[1.3.4] oxadiazol-2-yl)-butan-1-ol

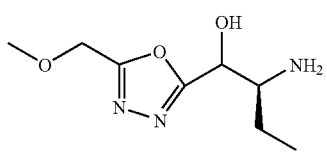

Step 1

(S)-(+)-2-amino-1-butanol (50 g, 561 mmol) in a mixture of water and dioxane (200 mL: 200 mL) was cooled to 0° C. and mixed with NaOH (26.9 g, 673 mmol) and di-tert-butyl-dicarbonate (146.96 g, 673 mmol). After the addition, the reaction was allowed to warm to room temperature. The reaction mixture was stirred for 2 h. After removing the dioxane, the residue was extracted with EtOAc, then washed with brine and dried with anhydrous MgSO$_4$, filtered and concentrated. Without further purification, the crude 2(S)-Boc-amino-1-butanol (120 g) was used for next step reaction.

Step 2

A solution of oxalyl chloride (40.39 g, 265 mmol) in MeCl$_2$ (700 mL) was stirred and cooled to −60° C. Dimethylsulfoxide (51.7 g, 663 mmol) in MeCl$_2$ (100 mL) was added dropwise. After 10 min., a solution of 2(S)-Boc-amino-1-butanol (50 g, 265 mmol) in MeCl$_2$ (100 mL) was added dropwise at −70° C. The reaction mixture was allowed to warm to −40° C. for 10 min. and then cooled to −70° C. again. A solution of triethylamine (74.9 g, 742 mmol) in MeCl$_2$ (100 mL) was added. The reaction mixture was allowed to warm to room temperature over 2 h. Saturated sodium dihydrogen phosphate (100 mL) was added, and then the organic layer was washed with brine and dried over MgSO$_4$. The solvent was removed to yield 45 g of 2(S)-Boc-aminobutyraldehyde.

Step 3

A mixture of methyl methoxyacetate (52 g, 500 mmol), hydrazine hydrate (30 mL) was heated to reflux for 8 h. Excess hydrazine and water were removed under vacuum. The residue was extracted with n-butanol, dried with Na$_2$SO$_4$. Excess n-butanol was removed to yield 45 g of hydrazide.

Step 4

A mixture of above hydrazide (45 g), triethylorthoformate (146 mL) and p-toluenesulfonic acid (61 mg) was heated at 140° C. for 8 h. Excess triethylorthoformate was removed under vacuum. The product was purified by silica gel column chromatography to yield 4.6 g of 2-methoxymethyl-1,3,4-oxadiazole.

Step 5

To a stirred solution of 2-methoxymethyl-1,3,4-oxadiazole (4.6 g, 40 mmol) in THF (100 mL) was added n-BuLi (1.6 M solution in 25.2 mL of hexane) dropwise under N$_2$ at −78° C. After 1 h, MgBr.Et$_2$O (10.4 g, 40.3 mmol) was added and the reaction mixture was allowed to warm to −45° C. for 1 h before being treated with 2(S)-Boc-aminobutyraldehyde (5.28 g, 28.25 mmol) in THF (20 mL). The reaction mixture was stirred for 1 h, quenched with saturated NH$_4$Cl, and extracted with ethyl acetate. The organic layer was washed with brine, dried with MgSO$_4$ and concentrated. The residue was purified by silica gel column chromatography to yield 2(S)-Boc-amino-1-(5-methoxymethyl-[1.3.4]-oxadiazol-2-yl)-1-butanol (500 mg).

Step 6

2(S)-Boc-Amino-1-(5-methoxymethyl-[1.3.4]-oxadiazol-2-yl)-1-butanol (500 mg, 1.66 mmol), and CH$_2$Cl$_2$ (5 mL) were mixed and TFA (0.5 mL) was added at room temperature. After stirring for 1 h, the solvent and excess TFA were removed under vacuum to produce 2(S)-amino-1-(5-methoxymethyl-[1.3.4]oxadiazol-2-yl)-butan-1-ol. TFA salt (340 mg).

Reference R

Synthesis of 2(S)-amino-1-(5-phenyl-[1.3.4]oxadiazol-2-yl)butan-1-ol

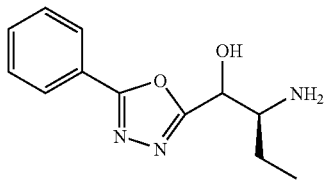

Step 1

A mixture of the benzoic hydrazide (22.5 g, 165 mmol), triethylorthoformate (150 mL) and p-toluenesulfonic acid (300 mg) was heated at 120° C. for 12 h. Excess triethylorthoformate was removed under vacuum and the residue was purified by silica gel column chromatography to produce 2-phenyl-[1.3.4]-oxadiazole (14.5 g).

Step 2

To a stirred solution of the 2-phenyl-[1.3.4]oxadiazole (10 g, 68.5 mmol) in THF (100 mL) was added n-BuLi (1.6 M solution in 42.8 mL of hexane) dropwise under $N_2$ at −78° C. After 1 h, $MgBr.Et_2O$ (17.69 g, 68.5 mmol) was added and the reaction mixture was allowed to warm to −45° C. for 1 h before being treated with (S)-2-Boc-aminobutyraaldehyde (7.8 g, 41 mmol) in THF (20 mL). The reaction mixture was stirred for 1 h, quenched with saturated $NH_4Cl$, and extracted with ethyl acetate. The organic layer was washed with brine, dried with $MgSO_4$ and concentrated. The residue was purified by silica gel column chromatography to yield 2-(2(S)-Boc-amino-1-hydroxybutyl)-5-phenyl-[1.3.4]-oxadiazole (9.7 g).

Step 3

2-(2(5)-Boc-amino-1-hydroxybutyl)-5-phenyl-[1.3.4]-oxadiazole (505 mg, 1.5 mmol) and $CH_2Cl_2$ (5 mL) were mixed and TFA (1 mL) was added at room temperature. After stirring for 1 h, the solvent and excess TFA were removed under vacuum to produce 530 mg of 2(S)-amino-1-(5-phenyl-[1.3.4]oxadiazol-2-yl)-1-butanol TFA salt.

Reference S

Synthesis of 2(S)-amino-1-oxazolo[4,5-b]pyridin-2-yl-butan-1-ol

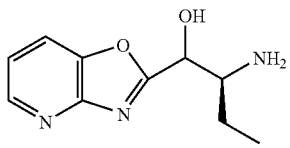

Step 1

A mixture of 2-amino-3-hydroxypyridine (25 g, 227 mmol), triethylorthoformate (75 mL) and p-toluenesulfonic acid (61 mg) was heated at 140° C. for 8 h. Excess triethylorthoformate was removed under vacuum. The product was crystallized from ethyl acetate to yield 22.5 g of oxazolo[4,5-b]pyridine.

Step 2

To a stirred solution of the oxazolo[4,5-b]pyridine (12 g, 100 mmol) in THF (300 mL) was added n-BuLi (1.6 M solution in 62.5 mL of hexane) drop wise under $N_2$ at −78° C. After 1 h, $MgBr.Et_2O$ (25.8 g, 100 mmol) was added and the reaction mixture was allowed to warm to −45° C. for 1 h before being treated with (S)-2-Boc-aminobutylaldehyde (11.46 g, 60 mmol) in THF (50 mL). The reaction mixture was stirred for 1 h, quenched with saturated $NH_4Cl$, and extracted with ethyl acetate. The organic layer was washed with brine, dried with $MgSO_4$ and concentrated. The residue was purified by silica gel column chromatography to yield 2(S)-Boc-amino-1-(oxazolo[4,5-b]pyridin-2-yl)-1-butanol (14.1 g).

Step 3

2-Boc(S)-Amino-1-(oxazolo[4,5-b]pyridin-2-yl)-1-butanol (311 mg, 1 mmol) and methylene chloride (5 mL) were mixed and TFA (1 mL) was added at room temperature. After stirring for 1 h, the solvent and excess TFA were removed under vacuum to produce 355 mg of 2(S)-amino-1-oxazolo[4,5-b]pyridin-2-yl-butan-1-ol TFA salt.

Reference T

Synthesis of 2(S)-amino-1-(5-pyridin-4-yl-[1.3.4]oxadiazol-2-yl)-butan-1-ol

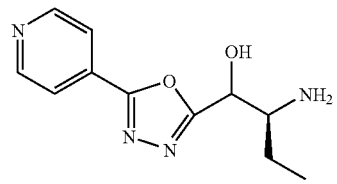

Step 1

A mixture of the isonicotinic hydrazide (13.7 g, 100 mmol), triethylorthoformate (60 mL) and p-toluenesulfonic acid (30 mg) was heated at 130° C. for 12 h. Excess triethylorthoformate was removed under vacuum. The crude was crystallized from ethyl acetate to give 14.8 g of 5-pyridin-4-yl-[1.3.4]oxadiazole.

Step 2

To a stirred solution of the 5-pyridin-4-yl-[1.3.4]oxadiazole (11.5 g, 78.2 mmol) in THF (300 mL) was added HMPA (5 ML) and n-BuLi (1.6 M solution in 48.9 mL of hexane) dropwise under $N_2$ at −78° C. After 1 h, $MgBr.Et_2O$ (20.2 g, 78.2 mmol) was added and the reaction mixture was allowed to warm to −45° C. for 1 h before being treated with 2-Boc-amino-butyraldehyde (9.7 g, 50.8 mmol) in THF (50 mL). The reaction mixture was stirred for 1 h, quenched with saturated $NH_4Cl$, and extracted with ethyl acetate. The organic layer was washed with brine, dried with $MgSO_4$ and concentrated. The residue was purified with silica gel column chromatography to yield 2(S)-Boc-amino-1-(5-pyridin-4-yl-[1.3.4]oxadiazol-2-yl)-butan-1-ol (3.5 g).

Step 3

2(S)-Boc-amino-1-(5-pyridin-4-yl-[1.3.4]oxadiazol-2-yl)-butan-1-ol (334 mg, 1 mmol) and $MeCl_2$ (5 mL) were mixed and TFA (0.5 mL) was added at room temperature. After stirring for 1 h, the solvent and excess TFA were removed under vacuum to produce 350 mg of 2(S)-amino-1-(5-pyridin-4-yl-[1.3.4]oxadiazol-2-yl)-butan-1-ol TFA salt.

Reference U

Synthesis of 2(S)-amino-1-(5-pyridin-3-yl-[1.3.4]oxadiazol-2-yl)-butan-1-ol

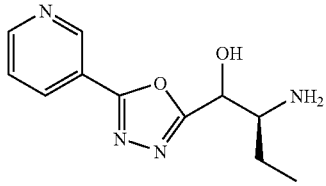

Step 1

To a stirred solution of the 3-[1.3.4]oxadiazol-2-yl-pyridine (5 g, 34 mmol) in THF (100 mL) was added HMPA (5 mL) and n-BuLi (1.6 M solution in hexane, 21.25 mL) drop wise under $N_2$ at −78° C. After 1 h, MgBr.$Et_2$O (8.77 g, 34 mmol) was added and the reaction mixture was allowed to warm to −45° C. for 1 h before being treated with 2(S)-Boc-aminobutyraldehyde (4.22 g, 22.1 mmol) in THF (20 mL). The reaction mixture was stirred for 1 h, quenched with saturated $NH_4Cl$, and extracted with ethyl acetate. The organic layer was washed with brine, dried with $MgSO_4$ and concentrated. The residue was purified with silica gel column chromatography to yield 2(S)-Boc-amino-1-(5-pyridin-3-yl-[1.3.4]oxadiazol-2-yl)-butan-1-ol (1.5 g).

Step 2

2(S)-Boc-Amino-1-(5-pyridin-3-yl-[1.3.4]oxadiazol-2-yl)-butan-1-ol (167 mg, 0.5 mmol) and $MeCl_2$ (5 mL) were mixed and TFA (0.5 mL) was added at room temperature. After stirring for 1 h, the solvent and excess TFA were removed under vacuum to produce 180 mg of 2(S)-amino-1-(5-pyridin-3-yl-[1.3.4]oxadiazol-2-yl)-butan-1-ol TFA salt.

Reference V

Synthesis of 2(S)-amino-1-benzoxazol-2-ylbutan-1-ol hydrochloride

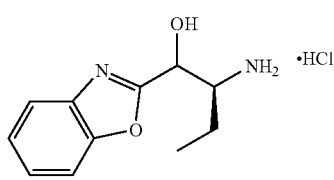

Step 1

To a solution of benzoxazole (28.6 g, 240 mmol) in toluene (150 mL) was added during ca 20 min., at about −4° C. a 2 M solution of isopropyl-magnesium chloride in THF (120 mL, 240 mmol). The red-brown mixture was stored at ca −4° C. and used as needed.

Step 2

To a solution of 2(S)-Boc-aminobutanol (50 g; 264 mmol) in dichloromethane (500 mL) and water (350 mL) were added at 20° C. TEMPO (0.01 eq), sodium bromide (1 eq) and sodium hydrogencarbonate (3 eq). The reaction mixture was stirred at 0° C. and diluted bleach (1.3 eq, 450 mL) was added over 40 min. The reaction mixture was stirred for 30 min. at 0° C. and then quenched with aq. thiosulfate. After decantation and extractions (dichloromethane), the organic phase was washed with brine, dried and concentrated in vacuo to dryness, giving 2(S)-(tert-butoxycarbonyl)aminobutyraldehyde as a low-melting solid (38.1 g; yield: 77%).

Step 3

A solution of 2(S)-(tert-butoxycarbonyl)aminobutyraldehyde (30 g, 160 mmol) in toluene (150 mL) was added over 30 min. at −5° C. to a solution of Grignard reagent of benzoxazole (prepared as described in Step 1 above). The reaction mixture was stirred for 0.5 h at 0° C., then 2.5 h at RT. Quenching with 5% aq. acetic acid, washings with 5% aq. sodium carbonate, then brine and concentration to dryness gave crude 2(S)-(tert-butoxycarbonyl)-amino-1-benzoxazol-2-yl-propan-1-ol. The residue was diluted with toluene, and silica gel was added. The slurry was filtered. Elution by toluene removed the non-polar impurities. Then an 8/2 mixture of toluene and ethyl acetate desorbed the 2(S)-(tert-butoxycarbonyl)-amino-1-benzoxazol-2-ylpropan-1-ol.

Step 4

To a solution of 2(S)-(tert-butoxycarbonyl)amino-1-benzoxazol-2-ylpropan-1-ol (26.3 g, 86 mmol) in isopropanol (118 mL) at 20-25° C. was added trimethylchlorosilane (1.4 eq). The solution was stirred for 5 h at 50° C. Concentration of the reaction mixture to 52 mL followed by addition of isopropyl ether (210 mL), filtration and drying under vacuum afforded 2(S)-amino-1-benzoxazol-2-yl-butan-1-ol hydrochloride salt as a grey solid (16.4 g; yield=79%; mixture of diastereomers.

Reference W

Synthesis of 4-amino-4-cyano-1-ethylpiperidine

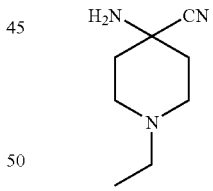

A mixture of 1-ethyl-4-piperidone (13.2 ml, 100 mmol), ammonium chloride (21.4 g, 400 mmol), sodium cyanide (19.6 g, 400 (mmol) and water (550 ml) was stirred at room temperature for 48 h. The pH of the reaction mixture was adjusted to 10.1 and the product was extracted with ethyl acetate. The organic extracts were washed with brine and dried over magnesium sulfate. Rotary evaporation of the solvent gave a mixture of 4-amino-4-cyano-1-ethyl piperazine and 4-hydroxy-4-cyano-1-ethyl piperazine (7.67 g). This mixture of products was treated with 7 M ammonia in methanol (20 ml) and allowed to stand at room temperature for 24 h. The methanol and excess ammonia were removed in vacuo and the residue was cooled to give 4-amino-4-cyano-1-ethylpiperidine as a crystalline solid (7.762 g).

Example 1

Synthesis of N-cyanomethyl-2S-[(benzenesulfonyliminomethyl)amino]-3-cyclohexylpropionamide (tabe 2, cpd 1)

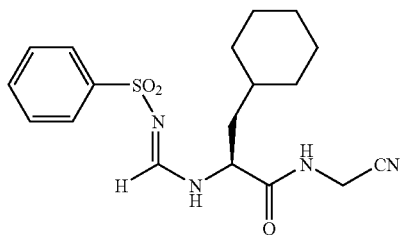

Step 1

A mixture of cyclohexyl alanine methyl ester hydrochloride (1.06 g, 5 mmol) in acetonitrile (25 mL) was cooled to 0° C. and N-methylmorpholine (0.55 mL) was added. A solution of ethyl benzenesulfonyl formimidate (1.06 g, 5 mmol) (prepared as described in Stetter, H. and Theisen, D. *Chem Ber.*, 1969, 102, 1641-42; and Ortiz, J. A. *Arzneim.-Forsch./Drug Res*, 1997, 47, 431-434) in acetonitrile (1.5 mL) was added to the reaction mixture. After stirring for 20 h at room temperature the acetonitrile was removed by rotary evaporation at reduced pressure and the resulting residue was then chromatographed on flash silica gel (250 mL), eluting with methanoymethylene chloride to give 2-[(benzenesulfonyliminomethyl)amino]-3-cyclohexyl-propionic acid methyl ester (1.227 g, 70%).

Step 2

A solution of 2-[(benzenesulfonyliminomethyl)amino]-3-cyclohexyl-propionic acid methyl ester in methanol (100 mL) was cooled in an ice bath and then treated with aqueous potassium hydroxide (0.989 M, 3.5 mL) over 35 min. The reaction mixture was stirred 75 min at 0° C. and then the methanol was removed by rotary evaporation at room temperature. Water (20 mL) was added to the residue, the pH was adjusted to 5.4 and the product was extracted with ethyl acetate to give after drying 2-[(benzenesulfonylimino-methyl)amino]-3-cyclohexyl-propionic acid (0.862 g, 73%).

Step 3

A mixture of ethyl dimethylaminopropylcarbodiimide hydrochloride (0.270 g, 1.14 mmol), hydroybenzotriazole (0.184 g, 1.2 mmol) and aminoacetonitrile hydrochloride (0.130 g, 1.4 mmol) in methylene chloride (2.5 mL) was cooled in an ice bath and then treated with 2-[(benzenesulfonylimino-methyl)amino]-3-cyclohexyl-propionic acid (0.386 g, 1.14 mmol) in methylene chloride (3 mL). N-methylmorpholine (0.155 g, 1.55 mmol) was added to the reaction mixture was then stirred at room temperature for 2 h. The reaction mixture was diluted with ice water and the product extracted with ethyl acetate. The extracts were washed with aqueous sodium bicarbonate, then brine, then dried over magnesium sulfate and evaporated. The resulting oil was crystallized from methylene chloride to give N-cyanomethyl-2S-[(benzenesulfonyliminomethyl)-amino]-3-cyclohexyl-propionamide (0.218 g, 51%).

$^1$H NMR (DMSO-$d_6$): δ 9.24 (dd, J=7 Hz, 5 Hz, 1H), 8.97 (t, J=5 Hz, 1H), 8.15 (d, J=5 Hz, 1H), 7.73 (m, 2H), 7.56 (m, 3H), 4.5 (m, 1H), 4.14 (d, J=5 Hz, 2H), 1.53 (m, 7H), 1.1 (m, 3H), 0.94 (m, 3H): Exact mass 376.16. Found: M+H=376.8, M+Na=399.2, M–H=375.0.

Following the procedure in Example 1 above, utilizing the appropriate starting materials the following compounds of this invention were prepared:

N-cyanomethyl-2S-[(1-benzenesulfonyliminoethyl)amino]-3-cyclohexylpropionamide. MS: 391.3 MH$^+$. (tabe 2, cpd 2)

N-(1-cyanocyclopropyl)-2S-(1-benzenesulfonyliminoethylamino)-3-cyclohexylpropionamide. MS: 417.3 MH$^+$. (tabe 2, cpd 3)

N-(4-cyanotetrahydrothiopyran-4-yl)-2S-(1-benzenesulfonyliminoethylamino)-3-cyclohexylpropionamide. MS: 477.2 M$^+$. (tabe 2, cpd 8)

N-(4-cyano-1,1-dioxohexahydro-1-$\lambda^6$-thiopyran-4-yl)-2S-(1-benzenesulfonyliminoethylamino)-3-cyclohexylpropionamide. MS: 509.2 MH$^+$. (tabe 2, cpd 9)

N-cyanomethyl-2R-(1-benzenesulfonyliminoethylamino)-3-(2-difluoromethoxyphenylmethanesulfanyl)propionamide. MS: 497.2 MH$^+$. (tabe 2, cpd 10)

N-cyanomethyl-2R-(1-benzenesulfonyliminoethylamino)-3-(2-difluoromethoxyphenylmethanesulfonyl)propionamide. MS: 529.4 MH$^+$. (tabe 2, cpd 11)

N-(4-cyano-1,1-dioxohexahydro-1-$\lambda^6$-thiopyran-4-yl)-2R-(1-benzenesulfonyliminoethylamino)-3-(difluoromethoxyphenylmethanesulfonyl)propionamide. $^1$H NMR (400 MHz, CDCl$_3$): 7.86-7.20 (m, 8H), 6.61(t, 1H), 4.42(AB q, 2H), 3.58 (dd, 1H), 3.44 (dd, 1H), 3.80 (m, 4H), 2.75-2.40 (m, 4H), 2.38 (s, 3H). MS: 647.3(MH$^+$). (table 2, cpd 13)

N-cyanomethyl-2R-(1-benzenesulfonyliminoethylamino)-3-phenylmethanesulfanylpropionamide. MS: 431.1 MH$^+$. (tabe 2, cpd 15)

N-cyanomethyl-2R-(1-benzenesulfonyliminoethylamino)-3-phenylmethanesulfonylpropionamide. MS: 463.1 MH$^+$. (tabe 2, cpd 16)

2S-(1-benzenesulfonyliminoethylamino)-N-{1S-(benzoxazol-2-ylcarbonyl)propyl}-3-(thiazol-2-yl)propionamide. MS: 391.3 MH$^+$. (tabe 1, cpd 6)

2R-(1-benzenesulfonyliminoethylamino)-N-{1S-(5-ethyl-[1.3.4]-oxadiazol-2-ylcarbonyl)propyl}-3-(2-difluoromethoxyphenylmethanesulfonyl)propionamide. $^1$H NMR (400 MHz, CDCl$_3$): 7.90-6.95 (m, 10H), 6.57 (t, 1H), 5.15 (m, 1H), 4.95 (m, 1H), 4.76 (d, 1H), 4.18 (d, 1H), 3.79 (dd, 1H), 3.46 (dd, 1H) 3.01 (q, 2H), 2.58 (s, 3H), 4.41 (q,), 2.15 (m, 1H), 1.92 (m, 1H), 1.45 (s, 3H), 1.01 (s, 3H). MS: 656.1 (MH$^+$). (table 1, cpd 9)

2RS-(1-benzenesulfonyliminoethylamino)-N-{1RS-(3-phenyl-[1.2.4]-oxadiazol-5-ylcarbonyl)propyl}-3-(2-difluoromethoxyphenylmethanesulfonyl)propionamide. MS: 704.4(MH$^+$). (table 1, cpd 10)

Example 2

Synthesis of N-(1-cyanocyclopropyl)-2S-(1-benzenesulfonyliminoethylamino)-3-(1-methyl-cyclohexyl)propionamide (table 2, cpd 19)

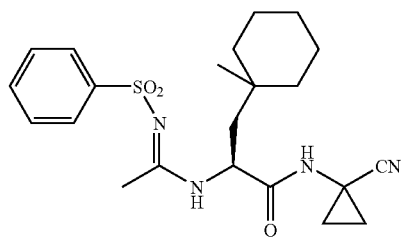

Step 1

To a stirred solution of 2S-tert-butoxycarbonylamino-3-(1-methylcyclohexyl)propionic acid (283 mg, 1.0 mmol) (prepared as described in Reference H except utilizing 1-methylcyclohexanol intead of 1-methylcyclopentanol) and 1-aminocyclopropanecarbonitrile HCl salt (178 mg, 1.5 mmol) in DMF (5 mL) at room temperature was added HATU (418 mg, 1.1 mmol), followed by diisopropyl ethylamine (0.87 mL, 5 mmol). After being stirred at room temperature overnight, the reaction mixture was concentrated under reduced pressure and then partitioned between ethyl acetate and brine. The combined organic extracts were dried ($MgSO^4$), concentrated under reduced pressure, and the residue was purified by flash chromatography on silica gel (eluted with 1:2 EtOAc/hexanes) to yield [1-(1-cyanocyclopropylcarbamoyl)-2S-(1-methylcyclohexyl)ethyl]-carbamic acid tert-butyl ester (315 mg, 90%).

Step 2

To a stirred solution of [1-(1-cyanocyclopropylcarbamoyl)-2S-(1-methylcyclohexyl)ethyl]-carbamic acid tert-butyl ester (300 mg, 0.86 mmol) in dry THF (2 mL) at room temperature was added slowly methanesulfonic acid (248 mg, 2.58 mmol). After 3 h, the reaction mixture was diluted with ethyl acetate and then neutralized with saturated sodium bicarbonate solution to pH=8-9. The aqueous layer was separated and extracted with ethyl acetate. The combined organic extracts were dried ($MgSO_4$), concentrated under reduced pressure to give 2S-amino-N-(1-cyano-cyclopropyl)-3-(1-methylcyclohexyl)propionamide which was used without purification for the next step.

Step 3

N-(1-Ethoxyethylidene)benzenesulfonamide (183 mg, 0.86 mmol) and 2S-amino-N-(1-cyanocyclopropyl)-3-(1-methylcyclohexyl)propionamide (214 mg, 0.86 mmol) were dissolved in dry DMF(3 mL). Cesium carbonate (839 mg, 2.58 mmol) was added at room temperature and the reaction mixture was stirred at room temperature for 2 h. After removal of the solvent under reduced pressure, the residue obtained was partitioned between ethyl acetate and brine. The combined organic extracts were dried ($MgSO_4$), concentrated under reduced pressure. The crude was purified by flash chromatography on silica gel (eluted with 2:1 EtOAc/hexanes) to yield the title compound (205 mg, 55%). $^1$H NMR (400 MHz, $CDCl_3$): δ 7.45 (m, 6H), 4.55 (m,1H), 2.12 (s, 3H), 1.95-1.05 (m, 16H), 0.92 (s, 3H). MS: 431.2($MH^+$).

Following the same procedure described in Example 2 above but substituting 2S-tert-butoxycarbonylamino-3-(1-methylcyclohexyl)-propionic acid with 2S-tert-butoxycarbonylamino-3-(1-methylpentyl)-propionic acid gave N-(1-cyanomethyl)-2S-(1-benzenesulfonyl-iminoethylamino)-3-(1-methylcyclopentyl)propionamide. (table 2, cpd. 14)

$^1$H NMR (400 MHz, $CDCl_3$): 8.50(br t, 1H), 7.9-7.40(m, 5H), 4.58 (m, 1H), 4.00 (m, 4H), 2.17 (s, 3H), 1.90-1.20 (m, 10H), 0.87 (s, 3M). MS: 391.0 ($MH^+$).

Following the same procedure described above, but substituting 1-aminocyclopropane-carbonitrile with 4-aminotetrahydrothiopyran-4-ylcarbonitrile and 2(S)-benzyloxycarbonylamino-3-(1-methylcyclohexyl)-propionic acid with 2(S)-benzyloxycarbonylamino-3-(1-methylcyclopentyl)-propionic acid gave N-(4-cyanotetrahydrothiopyran-4-yl)-2S-(1-benzenesulfonyliminoethylamino)-3-(1-methylcyclopentyl)propionamide. (table 2, cpd 17)

$^1$H NMR (400 MHz, $CDCl_3$): 7.79-7.40 (m, 6H), 7.20 (d, 1H), 4.60 (m, 1H), 2.95 (m, 2H), 2.70-2.30 (m, 4H), 2.15 (s, 3H), 2.10-1.15 (m, 12H), 0.95 (s, 3H). MS: 477.1 ($MH^+$).

2S-(1-benzenesulfonyliminoethylamino)-N-{1S-(benzoxazol-2-ylcarbonyl)propyl}-3-(1-methylcyclopentyl)propionamide. MS: 539.2 Mt. (tabe 1, cpd 7)

Example 3

Synthesis of N-(4-cyano-1,1-dioxohexahydro-X-thiopyran-4-yl)-2S-(1-benzenesulfonyliminoethylamino)-3-(1-methylcyclopentyl)-propionamide (table 2, cpd 18)

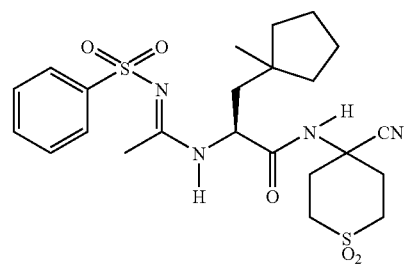

A solution of Oxone® (290 mg, 0.47 mmol) in water (1.5 mL) was added to a solution of the 2-(1-benzenesulfonyliminoethylamino)-N-(4-cyanotetrahydrothiopyran-4-yl)-3-(1-methylcyclopentyl)propionamide (172 mg, 0.36 mmol) in methanol(3 mL). The reaction mixture was stirred at room temperature for 4 h and then removed the solvent under reduced pressure. The residue obtained was partitioned between ethyl acetate and brine. The combined organic extracts were dried ($MgSO_4$) and concentrated under reduced pressure. The crude was purified by passing through a short pad of a celite to give the title compound (165 mg, 90% yield).
$^1$H NMR (400 MHz, $CDCl_3$): 7.90 (s, 1H), 7.79-7.40 (m, 6H), 6.78(d, 1H), 4.55 (m, 1H), 3.20-2.95 (m, 4H), 2.70-2.20 (m, 4H), 2.12 (s, 3H), 1.98-1.15 (m, 10H), 0.85 (s, 3H). MS: 509.2 ($MH^+$).

Example 4

Synthesis of 2R-(benzenesulfonyliminomethylamino)-N-[1S-(benzoxazol-2-ylcarbonyl)propyl]-3-(2-difluoromethoxyphenylmethanesulfonyl)propionamide (table 1, cpd 4)

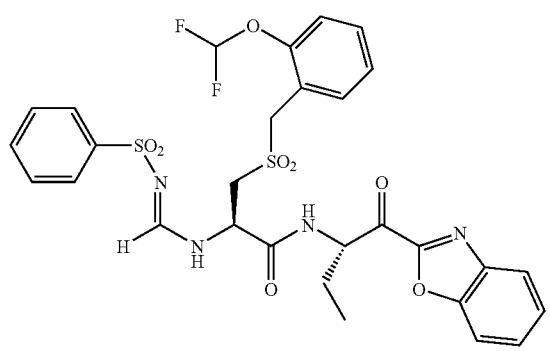

Step 1

A mixture of ethyl benzenesulfonyl formimidate (100 mg, 0.47 mmol), 2R-amino-N-[1S-(benzoxazol-2-ylhydroxymethyl)propyl]-3-(2-difluoromethoxyphenylmethanesulfanyl)-propionamide (136 mg, 0.29 mmol), 1,8-diazabicyclo[4.5.0]undec-7-ene (58 mg, 0.58 mmol) and acetonitrile (1 mL) was stirred at room temperature for 4 h. The reaction mixture was diluted with ice water and pH of the mixture was adjusted to 6.3 with 1N HCl. The product was extracted with ethyl acetate. The extracts were washed with saturated sodium bicarbonate, dried and the solvent was removed by rotary evaporation to give following purification by flash chromatography 2R-(1-benzenesulfonyliminomethylamino)-N-[f S-(benzoxazol-2-ylhydroxymethyl)propyl]-3-(2-difluoromethoxyphenylmethanesulfanyl)propionamide (53 mg).

Step 2

2R-(1-Benzenesulfonyliminomethylamino)-N-[1S-(benzoxazol-2-ylhydroxymethyl)-propyl]-3-(2-difluoromethoxyphenylmethanesulfanyl)propionamide (53 mg, 0.0837 mmol) in methanol (5 mL) was cooled on ice and treated with a solution of Oxone® (77 mg in 2 mL water). After 45 min., another 21 mg of Oxone® was added and after 45 min., methanol was removed under vacuum and reaction mixture was diluted with water and the product extracted with ethyl acetate. Following drying and evaporation of the solvent 2R-(1-benzenesulfonyliminomethylamino)-N-[1S-(benzoxazol-2-ylhydroxymethyl)propyl]-3-(2-difluoromethoxyphenylmethanesulfonyl)-propionamide (37 mg) was obtained.

Step 3

2R-(1-Benzenesulfonyliminomethylamino)-N-[1S-(benzoxazol-2-ylhydroxymethyl)propyl]-3-(2-difluoromethoxyphenylmethanesulfanyl)propionamide (37 mg, 0.0585 mmol) in methylene chloride (2 mL) was treated with Dess-Martin periodinane (35 mg, 0.082 mmol). After 50 min., another 11 mg of Dess-Martin periodinane was added. The reaction was quenched with sodium thiosulfate after another 25 min., and the product extracted methylene chloride. Purification by flash chromatography then gave the title compound (16 mg). Exact Mass 662.13. Found: M+H=663.5, M+Na=685.3, M−H=661.5. NMR (CDCl₃): 8.405 (d, J=4.4 Hz), u 7.94 (d, J=7.6 Hz), 7.88 (d, J=8 Hz). 7.80 (d, J=7.8 Hz), 7.688 (d, J=8 Hz), 7.6-7.44 (m), 7.33-7.4 (m), 6.673 (d, J=71.6 Hz), 6.49 (d, J=71.6 Hz), 5.46 (m), 5.0 (m), 4.395 (d, J=14 Hz), 3.69 (dd, J=2.8, 15.2 Hz), 3.60 (dd, J=7.3 Hz, 15.2 Hz), 2.25-2.14 (m), 1.95-1.85 (m), 1.00 (t, J=8 Hz) PPM.

Proceeding as described in Example 4 above, the following compounds were prepared.

2R-(1-benzenesulfonyliminoethylamino)-N-[1S-(benzoxazol-2-ylcarbonyl)propyl]-3-(2-difluoromethoxyphenylmethanesulfonyl)propionamide. MS: 677.3 MH⁺. (table 1, cpd 5)

2S-(benzenesulfonyliminomethylamino)-N-[1S-(benzoxazol-2-ylcarbonyl)propyl]-3-(cyclohexyl)propionamide. Exact Mass 524.21. Found: M+H=525.4, M+Na=547.5, M−H=523.4. (table 1, cpd 1)

Example 5

Synthesis of N-cyanomethyl-2R-[(benzenesulfonyliminomethyl)amino]-3-(2-difluoromethoxyphenylmethanesulfonyl)-propionamide (table 2, cpd 7)

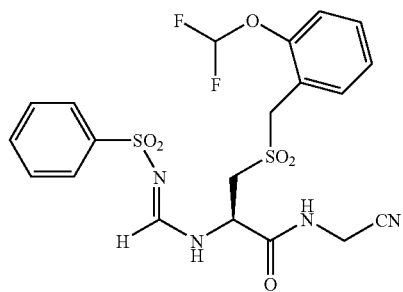

Step 1

A mixture of ethyl benzenesulfonyl formimidate (0.852 g, 4.00 mmol), R-(2-difluoromethoxybenzyl)cysteine (1.108 g, 4.00 mmol), 4-methylmorpholine (1.32 mL, 12 mmol) and acetonitrile (20 mL) was stirred at room temperature for 4 h. The 4-methyl morpholine and solvent were removed by rotary evaporation to give 2R-[(benzenesulfonyliminomethyl)amino]-3-(2-difluoromethoxyphenylmethanesulfanyl)-propionic acid.

Step 2

2R-[(Benzenesulfonyliminomethyl)amino]-3-(2-difluoromethoxyphenylmethanesulfanyl)-propionic acid (0.888 g, 2 mmol) in methylene chloride (10 mL) was cooled on ice and treated with HOBT (0.306 g, 2 mmol), EDCI (0.392 g, 2.5 mmol), and aminoacetonitrile hydrochloride (0.275 g, 3.00 mmol). 4-Methylmorpholine (2.73 mL, 5.00 mmol) was added to the reaction mixture which was then stirred overnight at room temperature. After diluting the reaction mixture with ice water and HCl the product was extracted with ethyl acetate. The extracts were dried and then purified by flash chromatography on silica gel eluting with ethyl acetate/hexane mixtures to give 2R-[(benzenesulfonyliminomethyl) amino]-N-cyanomethyl-3-(2-difluoromethoxy-phenylmethanesulfanyl)-propionamide)propyl]propionamide (0.340 g).

Step 3

A solution of 2R-[(benzenesulfonyliminomethyl)amino]-N-cyanomethyl-3-(2-difluoromethoxy-phenylmethanesulfanyl)-propionamide)propyl]-propionamide (0.241 g, 0.5 mmol) in methanol (15 mL) was cooled on ice and treated with Oxone® (0.430 g, 0.72 mmol) in water (5 mL). After 10 min., the cooling bath was removed and the reaction mixture was stirred at room temperature for 2 h. The methanol was removed on a rotary evaporator and the reaction mixture was diluted with water and then extracted with ethyl acetate. The extracts were dried and concentrated to give the title compound (0.316 g). Exact Mass 514.08 Found: M+H=515.1, M+Na=537.1, M−H=513.2.

Proceeding as described in Example 5 above, the following compounds were prepared.

N-cyanomethyl-2R-[(benzenesulfonyliminomethyl) amino]-3-(phenylmethanesulfonyl)-propionamide. Exact Mass 448.09. Found: M+H=449.3, M+Na=471.2, M−H=447.2. (table 2, cpd 12)

N-(1-cyanocyclopropyl-2RS-[(benzenesulfonyliminomethyl)amino]-3-(cyclohexyl)-propionamide. Exact Mass 402.17. Found: M+H=403.3, M+Na=425.3, M–H=401.0. (table 2, cpd 4)

N-cyanomethyl-2R-[(benzenesulfonyliminomethyl)amino]-3-(2-difluoromethoxyphenylmethanesulfanyl)propionamide. Exact Mass 482.09. Found: M+H=483.0, M+Na=505.1, M–H=481.0. (table 2, cpd 6)

Example 6

Synthesis of 2S-[(benzenesulfonyliminomorpholin-4-ylmethyl)amino]-N-[1S-(benzoxazol-2-yl-carbonyl)propyl]-3-cyclohexylpropionamide (table 1, cpd 8)

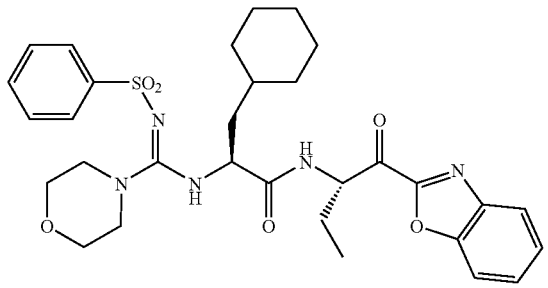

Step 1

A mixture of N-(bis-methylsulfanylmethylene)benzenesulfonamide (261 mg), cyclohexylalanine hydrochloride (171 mg), 1,8-diazabicyclo[5.4.0]undec-7-ene (0.45 mL) and acetonitrile (3 mL) was heated in a microwave apparatus at 110° C. for 15 min. The reaction mixture was cooled to room temperature and the pH was raised to 10 using 1N sodium hydroxide. This mixture was washed with ether and the aqueous layer was acidified to pH 4 with 1N hydrochloric acid. The product was then isolated by extraction with ethyl acetate. This sequence was repeated twice and the combined products were purified by flash chromatography (ethyl acetate methanol) to give 2S-[(benzenesulfonyliminomethylthiomethyl)amino]-3-cyclohexylpropionic acid (386 mg).

Step 2

A mixture of 2S-[(benzenesulfonyliminomethylthiomethyl)amino]-3-cyclohexylpropionic acid (100 mg), 2S-amino-1-benzoxazol-2-ylbutan-1-ol hydrochloride (54 mg), HATU (119 mg), diisopropylethyl amine (0.09 mL) and DMF (3 mL) was heated in a microwave apparatus for 10 min at 50° C. Aqueous ethyl acetate work up and purification by flash chromatography (ethyl acetate/hexane) gave 2S-[(benzenesulfonyliminomethylsulfanylmethyl)amino]-N-[1S-(benzoxazol-2-ylhydroxymethyl)propyl]-3-cyclohexylpropionamide (190 mg).

Step 3

A solution of 2S-[(benzenesulfonyliminomethylsulfanylmethyl)amino]-N-[1S-(benzoxazol-2-ylhydroxymethyl)propyl]-3-cyclohexylpropionamide (190 mg) and morpholine (0.29 mL) was heated in a microwave apparatus for 60 minutes at 90-100° C. The reaction mixture was washed with hydrochloric acid to remove excess morpholine. Flash chromatography then gave 2S-[(benzenesulfonyliminomorpholin-4-ylmethyl)amino]-N-[1S-(benzoxazol-2-ylhydroxymethyl)-propyl]-3-cyclohexylpropionamide (22 mg).

Step 4

2S-[(Benzenesulfonyliminomorpholin-4-ylmethyl)amino]-N-[1S-(benzoxazol-2-ylhydroxymethyl)propyl]-3-cyclohexylpropionamide (22 mg) in methylene chloride was treated with Dess-Martin periodinane (19 mg) for 25 min The reaction was quenched with aqueous sodium bicarbonate/sodium thiosulfate. Extraction followed by flash chromatography then gave the title compound (20 mg).

Biological Examples

Example 1

Cathepsin B Assay

Solutions of test compounds in varying concentrations were prepared in 10 μL of dimethyl sulfoxide (DMSO) and then diluted into assay buffer (40 μL, comprising: N,N-bis(2-hydroxyethyl)-2-aminoethanesulfonic acid (BES), 50 mM (pH 6); polyoxyethylenesorbitan monolaurate, 0.05%; and dithiothreitol (DOT), 2.5 mM). Human cathepsin B (0.025 pMoles in 25 μL of assay buffer) was added to the dilutions. The assay solutions were mixed for 5-10 seconds on a shaker plate, covered and incubated for 30 min at room temperature. Z-FR-AMC (20 nMoles in 25 μL of assay buffer) was added to the assay solutions and hydrolysis was followed spectrophotometrically at (λ 460 nm) for 5 min. Apparent inhibition constants ($K_i$) were calculated from the enzyme progress curves using standard mathematical models.

Compounds of the invention were tested by the above-described assay and observed to exhibit cathepsin B inhibitory activity.

Example 2

Cathepsin K Assay

Solutions of test compounds in varying concentrations were prepared in 10 μL of dimethyl sulfoxide (DMSO) and then diluted into assay buffer (40 μL, comprising: MES, 50 mM (pH 5.5); EDTA, 2.5 mM; and DTT, 2.5 mM. Human cathepsin K (0.0906 pMoles in 25 μL of assay buffer) was added to the dilutions. The assay solutions were mixed for 5-10 seconds on a shaker plate, covered and incubated for 30 min at room temperature. Z-Phe-Arg-AMC (4 nMoles in 25 μL of assay buffer) was added to the assay solutions and hydrolysis was followed spectrophotometrically at (λ 460 nm) for 5 min. Apparent inhibition constants ($K_i$) were calculated from the enzyme progress curves using standard mathematical models.

Compounds of the invention were tested by the above-described assay and observed to exhibit cathepsin K inhibitory activity.

Example 3

Cathepsin L Assay

Solutions of test compounds in varying concentrations were prepared in 10 μL of dimethyl sulfoxide (DMSO) and then diluted into assay buffer (40 μL, comprising: MES, 50 mM (pH 5.5); EDTA, 2.5 mM; and DTT, 2.5 mM. Human cathepsin L (0.05 pMoles in 25 μL of assay buffer) was added to the dilutions. The assay solutions were mixed for 5-10 seconds on a shaker plate, covered and incubated for 30 min at room temperature. Z-Phe-Arg-AMC (1 nMoles in 25 μL of assay buffer) was added to the assay solutions and hydrolysis was followed spectrophotometrically at (λ 460 nm) for 5 min. Apparent inhibition constants ($K_i$) were calculated from the enzyme progress curves using standard mathematical models.

Compounds of the invention were tested by the above-described assay and observed to exhibit cathepsin L inhibitory activity.

Example 4

Cathepsin S Assay

Solutions of test compounds in varying concentrations were prepared in 10 μL of dimethyl sulfoxide (DMSO) and then diluted into assay buffer (40 μL, comprising: MES, 50 mM (pH 6.5); EDTA, 2.5 mM; and NaCl, 100 mM); β-mercaptoethanol, 2.5 mM; and BSA, 0.00%. Human cathepsin S (0.05 pMoles in 25 μL of assay buffer) was added to the dilutions. The assay solutions were mixed for 5-10 seconds on a shaker plate, covered and incubated for 30 min at room temperature. Z-Val-Val-Arg-AMC (4 nMoles in 25 μL of assay buffer containing 10% DMSO) was added to the assay solutions and hydrolysis was followed spectrophotometrically (at λ 460 nm) for 5 min. Apparent inhibition constants ($K_i$) were calculated from the enzyme progress curves using standard mathematical models.

Compounds of the invention were tested by the above-described assay and observed to exhibit cathepsin S inhibitory activity.

Example 5

Cathepsin F Assay

Solutions of test compounds in varying concentrations were prepared in 10 μL of dimethyl sulfoxide (DMSO) and then diluted into assay buffer (40 μL, comprising: MES, 50 mM (pH 6.5); EDTA, 2.5 mM; and NaCl, 100 mM); DTT, 2.5 mM; and BSA, 0.01%. Human cathepsin F (0.1 pMoles in 25 μL of assay buffer) was added to the dilutions. The assay solutions were mixed for 5-10 seconds on a shaker plate, covered and incubated for 30 min at room temperature. Z-Phe-Arg-AMC (2 pMoles in 25 μL of assay buffer containing 10% DMSO) was added to the assay solutions and hydrolysis was followed spectrophotometrically (at λ 460 nm) for 5 min. Apparent inhibition constants ($K_i$) were calculated from the enzyme progress curves using standard mathematical models.

Compounds of the invention were tested by the above-described assay and observed to exhibit cathepsin F inhibitory activity.

Example 1

Representative pharmaceutical formulations Containing a Compound of Formula (Ia) or (Ib)

| ORAL FORMULATION | |
|---|---|
| Compound of Formula (Ia) or (Ib) | 10-100 mg |
| Citric Acid Monohydrate | 105 mg |
| Sodium Hydroxide | 18 mg |
| Flavoring | |
| Water | q.s. to 100 mL |

| -continued | |
|---|---|
| INTRAVENOUS FORMULATION | |
| Compound of Formula (Ia) or (Ib) | 0.1-10 mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |
| TABLET FORMULATION | |
| Compound of Formula (Ia) or (Ib) | 1% |
| Microcrystalline Cellulose | 73% |
| Stearic Acid | 25% |
| Colloidal Silica | 1%. |

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

We claim:

1. A compound of Formula (Ia) or (Ib):

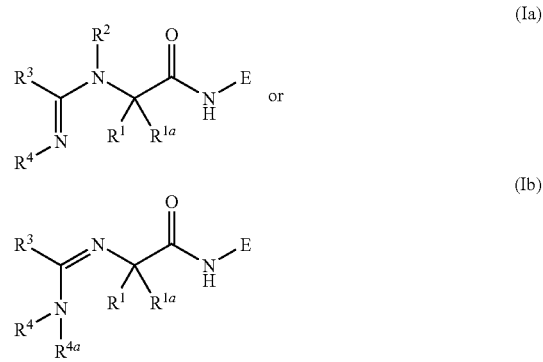

wherein:
E is
—C($R^{5a}$)($R^{6a}$)CN;
where:
$R^{5a}$ is hydrogen or alkyl; and
$R^{6a}$ is selected from the group consisting of hydrogen, alkyl, haloalkyl, carboxyalkyl, alkoxycarbonylalkyl, cycloalkyl, cycloalkylalkyl, aryl, aralkyl, heteroaryl, heteroaralkyl, heterocyclyl, heterocyclylalkyl, cyano, -alkylene-X—$R^{12}$ (where X is —O—, —$NR^{13}$—, —$CONR^{13}$—, —S(O)$_{n1}$—, —NHCO—, —CO—, or —C(O)O— where n1 is 0-2, and $R^{12}$ and $R^{13}$ are independently hydrogen, alkyl, haloalkyl, cycloalkyl, cycloalkylalkyl, aryl, aralkyl, heteroaryl, or heteroaralkyl) wherein the aromatic or alicyclic ring in $R^6$ and $R^{6a}$ is optionally substituted with one, two, or three $R^a$ independently selected from alkyl, haloalkyl, alkoxy, hydroxy, haloalkoxy, halo, carboxy, alkoxycarbonyl, amino, monsubstituted amino, disubstituted amino, nitro, aryloxy, benzyloxy, acyl, or arylsulfonyl where the aromatic or alicyclic ring in $R^a$ is optionally substituted with one or two substituents independently selected from alkyl, halo, alkoxy, haloalkyl, haloalkoxy, hydroxy, amino, alkylamino, dialkylamino, carboxy, or alkoxycarbonyl; or $R^{5a}$ and $R^{6a}$ taken together with the carbon atom to which both $R^{5a}$ and $R^{6a}$ are attached form (i) cycloalkylene optionally substituted with one or two $R^b$ independently selected from alkyl, halo, alkylamino, dialkylamino, aryl, aralkyl, cycloalkyl, cycloalkylalkyl, heteroaryl, heteroaralkyl, alkoxycarbonyl, or aryloxycarbonyl, or (ii) heterocycloalkylene optionally substituted with one to four $R^c$ which are independently selected from alkyl, haloalkyl, hydroxy, hydroxyalkyl, alkoxyalkyl, alkoxyalkyloxyalkyl, aryloxyalkyl, heteroaryloxyalkyl, aminoalkyl, acyl, aryl, aralkyl, heteroaryl, heteroaralkyl, heterocyclyl, heterocyclylalkyl, cycloalkyl, cycloalkylalkyl, $—S(O)_{n2}R^{14}$, -alkylene-$S(O)_{n2}—R^{15}$, $—COOR^{16}$, -alkylene-$COOR^{17}$, $—CONHR^{18}R^{19}$, or -alkylene-$CONHR^{20}R^{21}$ (where n2 is 0-2 and $R^{14}$-$R^{17}$, $R^{18}$ and $R^{20}$ are independently hydrogen, alkyl, haloalkyl, aryl, aralkyl, heteroaryl, heteroaralkyl, cycloalkyl, cycloalkylalkyl, or heterocyclyl and $R^{19}$ and $R^{21}$ are independently hydrogen or alkyl) wherein the aromatic or alicyclic ring in the groups attached to cycloalkylene or heterocycloalkylene is optionally substituted with one, two, or three substituents independently selected from alkyl, haloalkyl, alkoxy, hydroxy, haloalkoxy, halo, carboxy, alkoxycarbonyl, amino, monsubstituted amino, disubstituted amino, or acyl;

$R^1$ is hydrogen or alkyl;

$R^{1a}$ is hydrogen, alkyl, haloalkyl, cycloalkyl, cycloalkylalkyl, aryl, aralkyl, heteroaryl, heteroaralkyl, heterocyclylalkyl, or -alkylene-X—$R^{32}$ [wherein X is —$NR^{33}$—, —O—, —$S(O)_{n4}$—, —CO—, —COO—, —OCO—, —$NR^{33}CO$—, —$CONR^{33}$—, —$NR^{33}SO_2$—, —$SO_2NR^{33}$—, —$NR^{33}COO$—, —$OCONR^{33}$—, —$NR^{33}CONR^{34}$, or —$NR^{33}SO_2NR^{34}$— (where $R^{33}$ and $R^{34}$ are independently hydrogen, alkyl, or acyl and n4 is 0-2) and $R^{32}$ is hydrogen, alkyl, haloalkyl, cycloalkyl, cycloalkylalkyl, heterocyclyl, aryl, aralkyl, heteroaryl, heteroaralkyl, heterocyclyl, or heterocyclylalkyl] wherein said alkylene chain is optionally substituted with one to six halo wherein the aromatic or alicyclic ring in $R^{1a}$ is optionally substituted with one, two, or three $R^e$ independently selected from alkyl, haloalkyl, alkoxy, hydroxy, haloalkoxy, halo, nitro, cyano, carboxy, alkoxycarbonyl, aryl, heteroaryl, cycloalkyl, cycloalkylalkyl, aralkyl, heteroaralkyl, amino, monsubstituted amino, disubstituted amino, or acyl; or $R^2$ is hydrogen or alkyl;

$R^3$ is hydrogen, alkyl, haloalkyl, cycloalkyl, aryl, aralkyl, heteroaryl, heteroaralkyl, heterocyclyl, heterocyclylalkyl, amino, mono or disubstituted amino, or -alkylene-$X^3$—$R^{35}$ wherein $X^3$ is —$NR^{36}$—, —O—, —$S(O)_{n5}$—, —CO—, —COO—, —OCO—, —$NR^{36}CO$—, —$CONR^{36}$—, —$NR^{36}SO_2$—, —$SO_2NR^{36}$—, —$NR^{36}COO$—, —$OCONR^{36}$—, —$NR^{36}CONR^{37}$—, or —$NR^{36}SO_2NR^{37}$— (where $R^{36}$ and $R^{37}$ are independently hydrogen, alkyl, or acyl and n5 is 0-2) and $R^{35}$ is hydrogen, alkyl, haloalkyl, cycloalkyl, cycloalkylalkyl, aryl, aralkyl, heteroaryl, or heteroaralkyl wherein the aromatic or alicyclic rings in $R^3$ are optionally substituted by one, two, or three $R^g$ independently selected from alkyl, halo, hydroxy, alkoxy, haloalkyl, haloalkoxy, oxo, cyano, nitro, acyl, acyloxy, aryl, heteroaryl, aralkyl, heterocyclyl, aryloxy, benzyloxy, carboxy, alkoxycarbonyl, aryloxycarbonyl, carbamoyl, alkylthio, alkylsulfinyl, alkylsulfonyl, arylthio, arylsulfonyl, arylsulfinyl, alkoxycarbonylamino, aryloxycarbonylamino, alkylcarbamoyloxy, arylcarbamoyloxy, alkylsulfonylamino, arylsulfonylamino, aminosulfonyl, alkylaminosulfonyl, dialkylaminosulfonyl, arylaminosulfonyl, amino, monosubsituted or disubstituted amino, and further wherein the aromatic and alicyclic rings in $R^g$ are optionally substituted with one, two, or three $R^h$ wherein $R^h$ is independently selected from alkyl, halo, haloalkyl, haloalkoxy, hydroxy, nitro, cyano, hydroxyalkyl, alkoxy, alkoxyalkyl, aminoalkyl, alkylthio, alkylsulfonyl, amino, alkylamino, dialkylamino, aryl, heteroaryl, cycloalkyl, carboxy, carboxamido, or alkoxycarbonyl;

$R^4$ is —$S(O)_2R^{38}$ where $R^{38}$ is phenyl or naphthyl optionally substituted with one, two, or three $R^i$ independently selected from alkyl, alkoxy, halo, haloalkyl, haloalkoxy, hydroxy, alkylthio, alkylsulfonyl, arylsulfonyl, aminosulfonyl, acyl, amino, monosubstituted amino, disubstituted amino, carboxy, alkoxycarbonyl, hydroxyalkyl, alkoxyalkyl, aminoalkyl, aryl, heteroaryl, heterocyclyl, aryloxycarbonyl, heteroaryloxycarbonyl, aryloxy, heteroaryloxy, —$NHSO_2R^j$ where $R^j$ is alkyl, aryl, or heteroaryl, —$SO_2NR^kR^1$ where $R^k$ is hydrogen or alkyl and $R^1$ is alkyl, aryl, heteroaryl, hydroxyalkyl, alkoxyalkyl, or aminoalkyl, —$NHCOOR^m$ where $R^m$ is alkyl, aryl, or heteroaryl, or —$NHCONR^nR^o$ where $R^n$ and $R^o$ are independently hydrogen, alkyl, aryl, aralkyl, heteroaryl, or heteroaralkyl; where the aromatic or alicyclic ring in $R^i$ is optionally substituted with one or two substituents independently selected from alkyl, halo, alkoxy, haloalkyl, haloalkoxy, hydroxy, amino, alkylamino, dialkylamino, carboxy, or alkoxycarbonyl;

$R^{4a}$ is hydrogen, alkyl, halo, haloalkyl, haloalkyl, hydroxyalkyl, alkoxyalkyl, alkoxy, hydroxy, aryl, aralkyl, aroyl, heteroaryl, heteraralkyl, heteroaroyl, —$C(O)OR^{40}$ where ($R^{40}$ is hydrogen, alkyl, haloalkyl, cycloalkyl, cycloalkylalkyl, heteroaryl, heteroarylalkyl, aryl, or aralkyl), alkylsulfonyl, arylsulfonyl, heteroarylsulfonyl, alkylaminosulfonyl, arylaminosulfonyl, or cycloalkyl wherein the aromatic rings in $R^{4a}$ are optionally substituted with one, two or three halogen, hydroxy, alkyl, alkoxy, haloalkyl, haloalkoxy, carboxy, nitrile, nitro, or —$CONH_2$;

or a pharmaceutically acceptable salts thereof.

2. The compound of claim 1 wherein $R^4$ is —$S(O)_2R^{38}$ where $R^{38}$ is phenyl or naphthyl optionally substituted with one, two, or three $R^i$ independently selected from alkyl, alkoxy, halo, haloalkyl, haloalkoxy, hydroxy, alkylthio, alkylsulfonyl, arylsulfonyl, aminosulfonyl, acyl, amino, monosubstituted amino, disubstituted amino, carboxy, alkoxycarbonyl, hydroxyalkyl, alkoxyalkyl, aminoalkyl, aryl, heteroaryl, or heterocyclyl where the aromatic or alicyclic ring in $R^i$ is optionally substituted with one or two substituents independently selected from alkyl, halo, alkoxy, haloalkyl, haloalkoxy, hydroxy, amino, alkylamino, dialkylamino, carboxy, or alkoxycarbonyl.

3. The compound of claim 1 wherein E is —$CR^{5a}R^{6a}CN$ where $R^{5a}$ and $R^{6a}$ together with the carbon atom to which they are attached form cycloalkylene optionally substituted with one or two $R^b$ independently selected from alkyl, halo, dialkylamino, aryl, aralkyl, cycloalkyl, cycloalkylalkyl, heteroaryl, heteroaralkyl, alkoxycarbonyl, or aryloxycarbonyl.

4. The compound of claim 1 wherein E is —$CR^{5a}R^{6a}CN$ where $R^{5a}$ and $R^{6a}$ together with the carbon atom to which they are attached form cyclopropylene, cyclobutylene, cyclopentylene, or cyclohexylene optionally substituted with with one or two $R^b$ independently selected from alkyl, halo, dialkylamino, aryl, aralkyl, cycloalkyl, cycloalkylalkyl, heteroaryl, heteroaralkyl, alkoxycarbonyl, or aryloxycarbonyl.

5. The compound of claim 1 wherein E is —CR$^{5a}$R$^{6a}$CN where R$^{5a}$ and R$^{6a}$ together with the carbon atom to which they are attached form heterocycloalkylene optionally substituted with one to two R$^c$ which are independently selected from alkyl, haloalkyl, hydroxyalkyl, alkoxyalkyl, aryloxyalkyl, heteroaryloxyalkyl, aminoalkyl, acyl, aryl, aralkyl, heteroaryl, heteroaralkyl, cycloalkyl, cycloalkylalkyl, —S(O)$_{n2}$R$^4$, -alkylene-S(O)$_{n2}$—R$^{15}$, —COOR$^{16}$, -alkylene-COOR$^{17}$; —CONHR$^{18}$R$^{19}$, or -alkylene-CONHR$^2$OR$^{21}$ (where n2 is 0-2 and R$^{14}$-R$^{17}$, R$^{18}$ and R$^{20}$ are independently hydrogen, alkyl, haloalkyl, aryl, aralkyl, heteroaryl, heteroaralkyl, cycloalkyl, cycloalkylalkyl, or heterocyclyl and R$^{19}$ and R$^{21}$ are independently hydrogen or alkyl) wherein the aromatic or alicyclic ring in the groups attached to heterocycloalkylene is optionally substituted with one, two, or three substituents independently selected from alkyl, haloalkyl, alkoxy, hydroxy, haloalkoxy, halo, carboxy, alkoxycarbonyl, amino, monsubstituted amino, disubstituted amino, or acyl.

6. The compound of any of the claims 1-5 wherein:
R$^1$ is hydrogen; and
R$^{1a}$ is alkyl, cycloalkyl, aralkyl, heteroaralkyl, cycloalkylalkyl, heterocyclylalkyl, or -alkylene-X—R$^{32}$ [wherein X is —NR$^{33}$—, —O—, —S(O)$_{n4}$—, —CO—, —COO—, —OCO—, —NR$^{33}$CO—, —CONR$^{33}$—, —NR$^{33}$SO$_2$—, —SO$_2$NR$^{33}$—, —NR$^{33}$COO—, —OCONR$^{33}$—, —NR$^{33}$CONR$^{34}$, or —NR$^{33}$SO$_2$NR$^{34}$— (where R$^{33}$ and R$^{34}$ are independently hydrogen, alkyl, or acyl and n4 is 0-2) and R$^{32}$ is hydrogen, alkyl, haloalkyl, cycloalkyl, cycloalkylalkyl, heterocyclyl, aryl, aralkyl, heteroaryl, heteroaralkyl, heterocyclyl, or heterocyclylalkyl] wherein said alkylene chain is optionally substituted with one to six halo and wherein the aromatic or alicyclic ring in R$^{1a}$ is optionally substituted with one, two, or three R$^e$ independently selected from alkyl, haloalkyl, alkoxy, hydroxy, haloalkoxy, halo, nitro, cyano, carboxy, alkoxycarbonyl, aryl, heteroaryl, cycloalkyl, cycloalkylalkyl, aralkyl, heteroaralkyl, amino, monsubstituted amino, disubstituted amino, or acyl.

7. The compound of any of the claims 1-5 wherein:
R$^{1a}$ is 2-methylpropyl, 2,2-dimethylpropyl, 4,4-dimethylcyclohexylmethyl, 4-ethyl-4-methylcyclohexylmethyl, 4,4-diethylcyclohexylmethyl, 3,3-dimethylcyclohexylmethyl, 3,5-dimethylcyclohexylmethyl, 1-ethoxycarbonylpiperidin-4-ylmethyl, 1-methylpiperidin-4-ylmethyl, cycloheptylmethyl, cyclooctylmethyl, 3,3-dimethylbutyl, 3-methylbutyl, 2-cyclohexylethyl, 2,2,3-trimethylbutyl, 2-cyclohexyl-2-methylpropyl, 3,3-dimethylpentyl, 3-ethyl-3-methylpentyl, 2-(1-methylcyclohexyl)ethyl, tetrahydronaphthylmethyl, 2-tetrahydropyran-4-ylethyl, 2-(1-methylcyclopropyl)ethyl, 2-(1-methylcyclopropyl)-2-methylpropyl, 2-cyclopentylethyl, 2-cyclopentyl-2-methylpropyl, 4-isopropyl-4-methylcyclohexylmethyl, phenylmethanethiomethyl, phenylmethanesulfinylmethyl, dimethylaminomethyl, pyrrolidin-1-ylmethyl, piperidin-1-ylmethyl, morpholin-4-ylmethyl, thiomorpholin-4-ylmethyl, 1-oxo-thiomorpholin-4-ylmethyl, 1,1-dioxothiomorpholin-4-ylmethyl, tetrahydrothiopyran-4-ylmethyl, 1-oxotetrahydrothiopyran-4-ylmethyl, 1,1-dioxotetrahydrothiopyran-4-ylmethyl, 1-methylpiperazin-4-ylmethyl, benzyloxymethyl, n-butyl, ethoxymethyl, ethylthiomethyl, ethylsulfinylmethyl, ethylsulfonylmethyl, isopropylthiomethyl, isopropyloxymethyl, 2-dimethylaminoethyl, 2-piperidin-1-ylethyl, 2-pyrrolidin-1-ylethyl, 2-methylthioethyl, 2-methylsulfinylethyl, 2-methysulfonylethyl, tert-butylthiomethyl, tert-butyloxymethyl, benzyl, 4-methoxybenzyl, imidazol-4-ylmethyl, 4-dimethylaminobutyl, indol-3-ylmethyl, 2-dimethylaminocarbonylethyl, 2-pyrrolidin-1-ylcarbonylethyl, dimethylaminocarbonylmethyl, pyrrolidin-1-ylcarbonylmethyl, methoxycarbonylmethyl, 2-fluorophenylmethanesulfonylmethyl, 2-chlorophenylmethanesulfonylmethyl, 2-nitrophenylmethanesulfonylmethyl, 2-cyanophenylmethanesulfonylmethyl, pyridin-3-ylmethanesulfonylmethyl, pyridin-2-ylmethanesulfonylmethyl, pyridin-4-ylmethanesulfonylmethyl, 2-fluorophenylmethanethiomethyl, 2-chlorophenylmethanethiomethyl, 2-cyanophenylmethanethiomethyl, 2-nitrophenylmethanethiomethyl, cyclohexylmethanethiomethyl, cyclohexylsulfinylthiomethyl, cyclohexylmethanesulfonylmethyl, 3,4-dichlorobenzyl, 2-chlorobenzyl, 4-ethoxybenzyl, 4-nitrobenzyl, biphen-4-ylmethyl, naphth-1-ylmethyl, 2-methylbutyl, 1-methylpropyl, naphth-2-ylmethyl, 4-chlorobenzyl, 3-chlorobenzyl, 4-fluorobenzyl, indol-2-ylmethyl, 1-benzylimidazol-4-ylmethyl, 2-phenethyl, 4-hydroxybenzyl, 2-(4-hydroxyphenyl)ethyl, 4-ethyl-4-methylpiperidin-1-ylmethyl, 2-methylcyclohexylmethyl, 4-methoxycyclohexylmethyl, indol-1-ylmethyl, 1-methylpiperidin-2-ylmethyl, 2-bicylo[2.2.1]hep-3-tylethyl, 8-methyl-8-aza-bicyclo[3.2.1]oct-3-ylmethyl, bicyclo[3.2.1]oct-3-ylmethyl, bicyclo[3.1.1]hept-3-ylmethyl, 6,6-dimethylbicyclo[3.1.1]hept-3-ylmethyl, 6,6-dimethylbicyclo[3.1.1]hept-4-ylmethyl, 2-bicyclo[2.2.1]hept-1-ylethyl, bicyclo[2.2.1]hept-2-ylethyl, thiophene-2-sulfonylmethyl, 3-chloro-2-fluorophenylmethane-sulfonylmethyl, benzenesulfonylmethyl, phenylmethanesulfonylmethyl, 2-benzenesulfonylethyl, 2-(pyridin-2-ylsulfonyl)ethyl, 2-(pyridin-4-ylsulfonyl)ethyl, 2-phenylmethanesulfonyl-ethyl, oxypyridin-2-ylmethanesulfonylmethyl, 4-methoxyphenyl-methanesulfonylmethyl, p-tolylmethanesulfonylmethyl, 4-chlorophenylmethanesulfonylmethyl, o-tolylmethanesulfonylmethyl, 3,5-dimethylphenylmethanesulfonylmethyl, 4-trifluoromethylphenylmethanesulfonylmethyl, 4-trifluoromethoxyphenylmethanesulfonylmethyl, 2-bromophenylmethanesulfonylmethyl, naphth-2-ylmethanesulfonylmethyl, 3-methylphenylmethanesulfonylmethyl, 3-trifluoromethylphenylmethanesulfonylmethyl, 3-trifluoromethoxyphenylmethane-sulfonylmethyl, 4-fluoro-2-trifluoromethoxyphenylmethanesulfonylmethyl, 2-fluoro-6-trifluoromethylphenylmethane-sulfonylmethyl, 2,6-difluorobenzyl, 1-methylcyclopentylmethyl, cyclohexyl, pyridin-4-ylmethyl, 3-chlorophenylmethanesulfonylmethyl, 2-trifluoromethylphenylmethanesulfonylmethyl, 4-tert-butylphenylmethanesulfonylmethyl, 2-fluoro-3-methylphenylmethanesulfonyl-methyl, 3-fluorophenylmethanesulfonylmethyl, 4-fluorophenylmethanesulfonylmethyl, 2,5-difluorophenylmethanesulfonylmethyl, 2,6-difluorophenylmethanesulfonylmethyl, 2,5-dichlorophenylmethanesulfonylmethyl, 3,4-dichlorophenylmethanesulfonylmethyl, 2-(1,1-difluoromethoxy)phenylmethanesulfonylmethyl, 3-cyanophenylmethane-sulfonylmethyl, 2-trifluoromethoxyphenylmethanesulfonylmethyl, 3-trifluoromethoxyphenylmethanesulfonylmethyl, 2,3-difluorophenylmethane-sulfonylmethyl, 2,5- difluorophenylmethanesulfonylmethyl, biphenyl-2-ylmethane-sulfonylmethyl, cyclohexylmethyl, 3-fluorophenyl-methanesulfonylmethyl, 2-pyridin-2-ylsulfonylethyl, 2-phenylsulfonylethyl, 2,2-difluoro-3-phenylpropyl, 2,2-dichloro-3-phenylpropyl, 2,2,2-trichloroethyl, 2,2-dichloroethyl, 1,4-dimethylcyclopentylmethyl, 3,4-difluorophenylmethanesulfonylmethyl, 2,4-difluorophenylmethanesulfonylmethyl, 2,4,6-trifluorophenylmethanesulfonylmethyl, 2,4,5-trifluorophenylmethanesulfonylmethyl, 2,3,4-trifluorophenylmethanesulfonylmethyl, 2,3,5-trifluorophenylmethanesulfonylmethyl, 2,5,6-trifluorophenylmethanesulfonyl-methyl, 2-chloro-5-trifluoromethylphenylmethanesulfonylmethyl, 2-methylpropane-1-sulfonylmethyl, 2-fluoro-3-trifluoromethyl phenylmethanesulfonylmethyl, 2-fluoro-4-trifluoromethylphenylmethanesulfonylmethyl, 2-fluoro-5-trifluoromethyl-phenylmethanesulfonylmethyl, 4-fluoro-3-trifluoromethylphenylmethane-sulfonylmethyl, 2-methoxyphenylmethanesulfonyl-methyl, 3,5-bis-trifluoromethylphenyl-methanesulfonylmethyl, 4-difluoromethoxyphenylmethanesulfonylmethyl, 3-difluoromethoxyphenylmethanesulfonylmethyl, 2,6-dichlorophenylmethanesulfonylmethyl, biphenyl-4-ylmethanesulfonylmethyl, 3,5-dimethylisoxazol-4-ylmethanesulfonylmethyl, 5-chlorothien-2-ylmethanesulfonylmethyl, 2-[4-(1,1-difluoromethoxy)benzenesulfonyl]ethyl, 2-[2-(1,1-difluoromethoxy)benzenesulfonyl]ethyl, 2-[3-(1,1-difluoromethoxy)benzenesulfonyl]ethyl, 2-(4-trifluoromethoxybenzenesulfonyl)ethyl, 2-(3-trifluoromethoxybenzenesulfonyl)-ethyl, 2-(2-trifluoromethoxybenzenesulfonyl)-ethyl, (cyanomethylmethylcarbamoyl)methyl, biphenyl-3-ylmethyl, 2-oxo-2-pyrrolidin-1-ylethyl, 2-benzenesulfonylethyl, isobutylsulfanylmethyl, 2-phenylsulfanylethyl, cyclohexylmethanesulfonylmethyl, 2-cyclohexylethanesulfonyl, benzyl, naphth-2-yl, phenylmethanesulfanylmethyl, 2-trifluoromethylphenyl-metahnesulfanylmethyl, phenylsulfanylethyl, cyclopropylmethanesulfonylmethyl, 2-methylpropylsulfonylmethyl, 5-bromothien-2-ylmethyl, 3-phenylpropyl, 2,2-difluoro-3-phenylpropyl, 3,4,5-trimethoxy-phenylmethanesulfonyl-methyl, 2,2-difluoro-3-thien-2-ylpropyl, cyclohexylethyl, cyclohexylmethyl, cyclopentylmethyl, tert-butylmethyl, 1-methylcyclohexylmethyl, 1-methylcyclopentylmethyl, 2,2-difluoro-3-phenylpropyl, 2,2-dimethyl-3-phenylpropyl, 1-benzylcyclopropylmethyl, or benzyloxymethyl; and $R^1$ is hydrogen.

8. The compound of any of the claims 1-5 wherein:

$R^3$ is hydrogen, alkyl, cycloalkyl, phenyl, benzyl, naphthyl, alkylSO$_2$alkyl, cycloalkylSO$_2$alkyl, arylSO$_2$alkyl, pyrrolidinyl, piperidinyl, morpholinyl, thiomorpholinyl, piperazinyl, indolinyl, pyranyl, thiopyranyl, furanyl, thienyl, pyrrolyl, oxazolyl, thiazolyl, imidazolyl, pyridinyl, isoxazolyl, pyrimidinyl, pyrazinyl, pyridazinyl, indolyl, quinolinyl, benzofuranyl, benzthienyl, benzimidazolyl, benzthiazolyl, benzoisoxazolyl, benzoxazolyl or amino; wherein the aromatic or alicyclic ring in $R^3$ is optionally substituted by one, two, or three $R^g$;

each $R^g$ is independently alkyl, halo, hydroxy, oxo, carboxy, cyano, nitro, carboxamide, cycloalkyl, phenyl, naphthyl, pyrrolidinyl, piperidinyl, morpholinyl, thiomorpholinyl, piperazinyl, furanyl, thienyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, benzoxazolyl, quinolinyl, isoquinolinyl, quinazolinyl, quinoxalinyl, alkoxy, —COR (where R is alkyl), —OC(O)R (where R is alkoxy or aryl), aryloxy, benzyloxy, alkoxycarbonyl, aryloxycarbonyl, carbamoyl wherein the nitrogen atom may be independently mono or di-substituted by alkyl, aryl, pyrrolidinyl, piperidinyl, morpholinyl, thiomorpholinyl, piperazinyl, furanyl, thienyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, —NHCOR (where R is alkyl or aryl), alkylthio, arylthio, alkylsulfinyl, alkylsulfonyl, arylsulfinyl, arylsulfonyl, alkoxycarbonylamino, aryloxycarbonylamino, alkylcarbamoyloxy, arylcarbamoyloxy, alkylsulfonylamino, arylsulfonylamino, alkylaminosulfonyl, arylaminosulfonyl, amino wherein the nitrogen atom may be independently mono or di-substituted by alkyl, aryl, pyrrolidinyl, piperidinyl, morpholinyl, thiomorpholinyl, piperazinyl, furanyl, thienyl, oxazolyl, thiazolyl, imidazolyl, triazolyl, tetrazolyl, pyridinyl, pyrimidinyl, pyrazinyl, indolyl, benzofuranyl, benzothienyl, benzimidazolyl, benzthiazolyl, quinolinyl, isoquinolinyl, quinazolinyl or quinoxalinyl, where the aromatic or alicyclic rings in $R^g$ may be further optionally substituted by one, two or three $R^h$ independently selected from alkyl, aryl, cycloalkyl, alkoxy, haloalkyl, haloalkoxy, halo, hydroxy, carboxy, carboxamido, cyano, or nitro;

$R^2$ is hydrogen or methyl; and $R^{4a}$ is hydrogen, alkyl, cycloalkyl, aryl, alkoxy, or hydroxy.

9. The compound of any of the claims 1-5 wherein:

$R^3$ is hydrogen, methyl, ethyl, isopropyl, cyclopropyl, cyclopentyl, cyclohexyl, phenyl, benzyl, naphthyl, pyrrolidinyl, piperidinyl, morpholinyl, thiomorpholinyl, piperazinyl, furanyl, thienyl, thiazolyl, imidazolyl, pyridinyl, pyrazinyl, or amino where the nitrogen atom is mono or disubstituted with alkyl and wherein the aromatic or alicylic rings in $R^3$ are optionally substituted with one, two, or three $R^g$ independently selected from methyl ethyl, fluoro, chloro, bromo, iodo, hydroxy, oxo, carboxy, cyano, nitro, carboxamide, cyclopropyl, phenyl, pyrrolidinyl, piperidinyl, morpholinyl, thiomorpholinyl, piperazinyl, thienyl imidazolyl, methoxy, acetyl, acetoxy, phenoxy, benzyloxy, methoxycarbonyl, phenoxycarbonyl, benzoyloxy, carbamoyl wherein the nitrogen atom is mono or disubstituted independently with methyl, ethyl or phenyl, acetylamino, benzoylamino, methylthio, phenylthio, phenylsulfonyl, methylsulfonyl, methoxycarbonylamino, phenoxycarbonylamino, methylcarbamoyloxy, phenylcarbamoyloxy, methylsulfonylamino, phenylsulfonylamino, methylaminosulfonyl, phenylaminosulfonyl, amino wherein the nitrogen atom is mono or disubstituted independently with methyl or phenyl; wherein the aromatic or alicyclic rings in $R^g$ are further optionally substituted with one, two, or three $R^h$ independently selected from methyl, cyclopropyl, phenyl, methoxy, fluoro, chloro, hydroxy, carboxy or carboxamido.

10. The compound of any of the claims 1-5 wherein:

$R^3$ is hydrogen, methyl, carboxy, ethyl isopropyl, cyclopropyl, cyclohexyl, phenyl, benzyl, naphthyl, pyrrolidinyl, piperidinyl, morpholinyl, thiomorpholinyl, furanyl, thientyl, thiazolyl, imidazoly, pyridinyl, pyrazinyl or amino where the nitrogen atom is optionally substituted with allyl and wherein the aromatic or alicyclic rings in $R^3$ are optionally substituted with one, two, or three $R^g$ independently selected from methyl, chloro, fluoro, phenyl, thienyl, methoxy, acetyl, acetoxy, phenoxy, benzyloxy, methoxycarbonyl, carbamoy wherein the nitrogen atom is mono or disubstitued independently with methyl or phenyl, acetylamino, methylthio, phenylthio, phenylsulfonyl, methylsulfonyl, methoxycarbonylamino, methylcarbamoyloxy, phenylcarbamoyloxy, methylsulfonylamino, phenylsulfonylamino, amino wherein the nitrogen atom is mono or disubstituted independently with methyl or phenyl;

$R^{4a}$ is hydrogen, alkyl or alkoxy; and $R^4$ is —$S(O)_2R^{38}$ where $R^{38}$ is phenyl or naphthyl optionally substituted with one, two, or three $R^1$ independently selected from alkyl, alkoxy, halo, haloalkyl, haloalkoxy, hydroxy, alkylthio, alkylsulfonyl, aminosulfonyl, acyl, amino, monosubstituted amino, disubstituted amino, hydroxyalkyl, alkoxyalkyl, aminoalkyl, aryl, heteroaryl, or heterocyclyl where the aromatic or alicyclic ring in $R^i$ is optionally substituted with one or two substituents independently selected from alkyl, halo, alkoxy, haloalkyl, haloalkoxy, hydroxy, amino, alkylamino, dialkylamino, carboxy, or alkoxycarbonyl.

11. The compound of any of the claims 1-5 where $R^4$ is —$S(O)_2R^{38}$ where $R^{38}$ is phenyl optionally substituted with one, two, or three $R^i$ independently selected from alkyl, alkoxy, halo, haloalkyl, haloalkoxy, hydroxy, alkylthio, alkylsulfonyl, aminosulfonyl, acyl, amino, monosubstituted amino, disubstituted amino, hydroxyalkyl, alkoxyalkyl, aminoalkyl, aryl, heteroaryl, or heterocyclyl where the aromatic or alicyclic ring in $R^i$ is optionally substituted with one or two substituents independently selected from alkyl, halo, alkoxy, haloalkyl, haloalkoxy, hydroxy, amino, alkylamino, dialkylamino, carboxy, or alkoxycarbonyl.

12. A compound of formula:

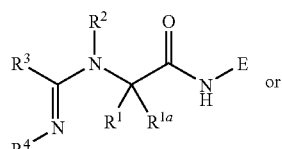

(Ia)

or

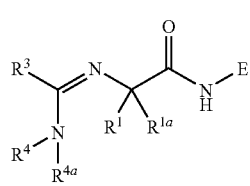

(Ib)

wherein:

$R^1$, $R^2$, and $R^{4a}$ are hydrogen;

$R^{1a}$ is cycloalkylalkyl wherein the alicyclic ring is optionally substituted with alkyl, heteroaralkyl, or -alkylene-$S(O)_{n4}$—$R^{32}$ where n4 is 0 to 2 and $R^{32}$ is aralkyl where the aromatic ring is optionally substituted with haloalkoxy;

$R^3$ is hydrogen, alkyl, heterocyclyl, or alkylthio;

$R^4$ is phenylsulfonyl;

E is —$CHR^6COR^{10}$ where $R^6$ is alkyl and $R^{10}$ is heteroaryl optionally substituted with alkyl or aryl, —$CH_2CN$, or —$CR^{5a}R^{6a}$ CN where $R^{5a}$ and $R^{6a}$ together with the carbon atom to which they are attached form cycloalkylene or heterocycloalkylene; or a pharmaceutically acceptable salt thereof.

13. A pharmaceutical composition comprising a compound of any of the claims 1-5 or 12 in admixture with one or more suitable excipients.

14. A method for treating psoriasis in an animal which method comprises administering to the animal a therapeutically effective amount of a compound of any of the claims 1-5 or 12.

\* \* \* \* \*

UNITED STATES PATENT AND TRADEMARK OFFICE
CERTIFICATE OF CORRECTION

PATENT NO. : 7,662,849 B2  Page 1 of 1
APPLICATION NO. : 10/559405
DATED : February 16, 2010
INVENTOR(S) : John W. Patterson et al.

It is certified that error appears in the above-identified patent and that said Letters Patent is hereby corrected as shown below:

On the front page of the Letters Patent after Prior Publication Data, please insert:

Item (60)
-- Related U.S. Application Data
Provisional Application No. 60/475,612, filed on June 4, 2003. --

Claim 1, Column 58, line 22:

"eroaryloxy, —$NHSO_2R^j$ where $R^1$ is alkyl, aryl, or het-"
should read:
-- eroaryloxy, —$NHSO_2R^j$ where $R^j$ is alkyl, aryl, or het- --

Claim 1, Column 58, lines 23 and 24:

"eroaryl, —$SO_2NR^kR^1$ where $R^k$ is hydrogen or alkyl and $R^1$ is alkyl, aryl, heteroaryl, hydroxyalkyl, alkoxyalkyl,"
should read:
-- eroaryl, —$SO_2NR^kR^l$ where $R^k$ is hydrogen or alkyl and $R^l$ is alkyl, aryl, heteroaryl, hydroxyalkyl, alkoxyalkyl, --

Signed and Sealed this

Eighteenth Day of May, 2010

David J. Kappos
*Director of the United States Patent and Trademark Office*

UNITED STATES PATENT AND TRADEMARK OFFICE
CERTIFICATE OF CORRECTION

PATENT NO. : 7,662,849 B2  Page 1 of 1
APPLICATION NO. : 10/559405
DATED : February 16, 2010
INVENTOR(S) : John W. Patterson et al.

It is certified that error appears in the above-identified patent and that said Letters Patent is hereby corrected as shown below:

Title page, item (*) Notice: should read as follows: Subject to any disclaimer, the term of this patent is extended or adjusted under 35 U.S.C. 154(b) by 579 days.

Signed and Sealed this

Twenty-second Day of June, 2010

David J. Kappos
*Director of the United States Patent and Trademark Office*

UNITED STATES PATENT AND TRADEMARK OFFICE
CERTIFICATE OF CORRECTION

PATENT NO. : 7,662,849 B2
APPLICATION NO. : 10/559405
DATED : February 16, 2010
INVENTOR(S) : John W. Patterson et al.

It is certified that error appears in the above-identified patent and that said Letters Patent is hereby corrected as shown below:

On the front page of the Letters Patent after Prior Publication Data, please insert:

Item (60)
-- Related U.S. Application Data
Provisional Application No. 60/475,612, filed on June 4, 2003. --

Claim 1, Column 58, line 22:

"eroaryloxy, —$NHSO_2R^j$ where $R^1$ is alkyl, aryl, or het-"
should read:
-- eroaryloxy, —$NHSO_2R^j$ where $R^j$ is alkyl, aryl, or het- --

Claim 1, Column 58, lines 23 and 24:

"eroaryl, —$SO_2NR^kR^1$ where $R^k$ is hydrogen or alkyl and $R^1$ is alkyl, aryl, heteroaryl, hydroxyalkyl, alkoxyalkyl,"
should read:
-- eroaryl, —$SO_2NR^kR^l$ where $R^k$ is hydrogen or alkyl and $R^l$ is alkyl, aryl, heteroaryl, hydroxyalkyl, alkoxyalkyl, --

Claim 5, Column 59, line 11:

"$COOR^{17}$; —$CONHR^{18}R^{19}$, or –alkylene-$CONHR^2OR^{21}$"
should read:
-- $COOR^{17}$, —$CONHR^{18}R^{19}$, or –alkylene-$CONHR^{20}R^{21}$ --

Claim 10, Column 63, line 2:
"with allyl and wherein the aromatic or alicyclic rings in"
should read:
-- with alkyl and wherein the aromatic or alicyclic rings in --

This certificate supersedes the Certificate of Correction issued May 18, 2010.

Signed and Sealed this

Twentieth Day of July, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,662,849 B2 | Page 1 of 1 |
| APPLICATION NO. | : 10/559405 | |
| DATED | : February 16, 2010 | |
| INVENTOR(S) | : Patterson et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 800 days.

Signed and Sealed this
Twenty-ninth Day of March, 2011

David J. Kappos
*Director of the United States Patent and Trademark Office*